(12) United States Patent
Miyake et al.

(10) Patent No.: US 8,362,289 B2
(45) Date of Patent: Jan. 29, 2013

(54) MIXTURE FOR RECOVERY UTILIZATION OR TRANSFER OF CARBON DIOXIDE

(75) Inventors: Nobuhisa Miyake, Tokyo (JP); Kazuhiro Onishi, Tokyo (JP); Kazuo Tomoyasu, Tokyo (JP); Budianto Bijanto, Tokyo (JP)

(73) Assignee: Asahi Kasei Chemicals Corporation, Tokyo (JP)

(*) Notice: Subject to any disclaimer, the term of this patent is extended or adjusted under 35 U.S.C. 154(b) by 0 days.

(21) Appl. No.: 12/225,176

(22) PCT Filed: Mar. 28, 2007

(86) PCT No.: PCT/JP2007/056553
§ 371 (c)(1),
(2), (4) Date: Sep. 16, 2008

(87) PCT Pub. No.: WO2007/114130
PCT Pub. Date: Oct. 11, 2007

(65) Prior Publication Data
US 2009/0169461 A1  Jul. 2, 2009

(30) Foreign Application Priority Data
Mar. 30, 2006 (JP) .................................. 2006-093337

(51) Int. Cl.
*C07F 7/22* (2006.01)
*C01B 31/24* (2006.01)
*C01B 31/20* (2006.01)
*C09K 3/00* (2006.01)

(52) U.S. Cl. ............... 556/88; 556/81; 556/83; 556/87; 556/89; 556/90; 556/105; 423/419.1; 423/438; 252/184

(58) Field of Classification Search ............... 423/419.1, 423/438, 594.9; 252/184; 556/81, 83, 87–90, 556/105
See application file for complete search history.

(56) References Cited

U.S. PATENT DOCUMENTS

| 5,545,600 A | 8/1996 | Knudsen et al. |
| 2008/0275262 A1* | 11/2008 | Miyake et al. ................ 556/89 |

FOREIGN PATENT DOCUMENTS

| EP | 1460056 | 9/2004 |
| EP | 1640357 | 3/2006 |
| JP | 05-184864 A | 7/1993 |
| JP | 2809368 | 7/1998 |
| JP | 2001-247519 | 9/2001 |
| JP | 2002-085966 | 3/2002 |

(Continued)

OTHER PUBLICATIONS

Choi et al., "Reaction of Dialkyltin Methoxide with Carbon Dioxide Relevant to the Mechanism of Catalytic Carbonate Synthesis." (Supplemental data/info. sheets) J. Am. Chem. Soc. 1999, 121, 3793-3794.*

(Continued)

*Primary Examiner* — Daniel C McCracken
*Assistant Examiner* — Daniel Berns
(74) *Attorney, Agent, or Firm* — Morgan, Lewis & Bockius LLP

(57) ABSTRACT

It is an object of the present invention to provide a mixture for recovery utilization or transfer of carbon dioxide gas. According to the present invention, disclosed is a mixture containing carbon dioxide and an alkyltin alkoxide composition containing carbon dioxide complex of an alkyltin alkoxide, the mixture having a composition with a specified ratio.

23 Claims, 15 Drawing Sheets

FOREIGN PATENT DOCUMENTS

| | | |
|---|---|---|
| JP | 2002-126439 | 5/2002 |
| JP | 3385359 | 1/2003 |
| JP | 2003-192643 | 7/2003 |
| JP | 2003-261315 | 9/2003 |
| JP | 2004-344703 | 12/2004 |
| WO | WO 03/055840 A1 | 7/2003 |
| WO | WO 2004/014840 A1 | 2/2004 |
| WO | WO 2005/000783 A1 | 1/2005 |
| WO | WO 2005/111049 A1 | 11/2005 |

OTHER PUBLICATIONS

Bloodworth et al., "Organometallic Reactions. Part VII. Further Addition Reactions of Tributyltin Methoxide and of Bistributyltin Oxide." J. Chem. Soc. (C) (1967), pp. 1309-1313.*

Davies et al., "Organometallic Reactions. Part VIII. Addition Reactions of Dibutyltin Dimethoxide and Related Compounds." J. Chem. Soc. (C) (1967), pp. 1313-1317.*

Sigma-Aldrich online catalog, "Tributyltin methoxide."© 2010. Viewed Aug. 6, 2010 at http://www.sigmaaldrich.com/catalog/ProductDetail.do?D7=0&N5=SEARCH_CONCAT_PNO%7CBRAND_KEY&N4=229245%7CALDRICH&N25=0&QS=on&F=SPEC.*

Chemical Book, "Dibutyldimethoxytin." (2007) Viewed Aug. 6, 2010 at http://www.chemicalbook.com/ChemicalProductProperty_EN_CB8779780.htm.*

Esp@cenet patent family table for WIPO Pub. No. WO 2005/111049 (patent family table viewed on Dec. 28, 2010).*

Jun-Chul Choi, et al. "Reaction of Dialkyltin Methoxide with Carbon Dioxide Relevant to the Mechanism of Catalytic Carbonate Synthesis" J. Am. Chem. Soc., vol. 121, No. 15, 1999 pp. 3793-3794.

Danielle Ballivet-Tkatchenko, et al. "The role of distannoxanes in the synthesis of dimethyl carbonate from carbon dioxide" Applied Catalysis A: General 255 (2003) 93-99.

Supplementary European Search Report for European Application No. 07739991 dated Mar. 16, 2011.

* cited by examiner

MIXTURE FOR RECOVERY UTILIZATION OR TRANSFER OF CARBON DIOXIDE

TECHNICAL FIELD

The present invention relates to a mixture for recovery utilization and/or transfer of carbon dioxide using an alkyltin alkoxide-containing composition. More specifically, the present invention relates to a process for effectively recycling carbon dioxide-containing gas discharged from a carbonate production step, and producing a carbonate efficiently and continuously.

BACKGROUND ART

Several methods for absorbing carbon dioxide gas have been reported. Specifically, chemical adsorption methods such as a method using a monoethanolamine aqueous solution (see, for example, Patent Document 1: Japanese Patent No. 2809368), a method using a tertiary amine (see, for example, Patent Document 2: Japanese Patent Application Laid-open No. 2003-261315), and a method using a porous powder having calcium hydroxide as a main component thereof (see, for example, Patent Document 3: Japanese Patent Application Laid-open No. 5-184864), and a solid adsorption method using a zeolite or the like (see, for example, Patent Document 4: Japanese Patent Application Laid-open No. 2004-344703) have been reported.

In the method for recovering carbon dioxide using a monoethanolamine aqueous solution or a tertiary amine, it is known that after the recovery, in a step of subjecting the absorbed carbon dioxide to decarbonation, the amine compound is entrained in the carbon dioxide; there has been reported a method in which, to remove this amine compound, the amine compound is removed by washing the carbon dioxide obtained through the decarbonation with washing water (see, for example, Patent Document 5: Japanese Patent Application Laid-open No. 2002-126439). However, in the case of using such an amine compound as a carbon dioxide absorbent, in most cases, the absorbent is used as an aqueous solution, and hence it is known that the carbon dioxide obtained through the decarbonation step contains water (see for example, Patent Document 5: Japanese Patent Application Laid-open No. 2002-126439), and furthermore in the case that an aqueous washing step for removing amine compound present as an impurity is added, the water content of the carbon dioxide is yet further increased.

On the other hand, in the case of using a solid absorbent such as calcium hydroxide or a zeolite as the absorbent, the absorbent must be made into a fine powder so as to increase the contact area, but there has been a problem that such a fine powder is difficult to handle. Methods in which this problem is resolved have been reported, for example a method using a lithiated oxide is known (see for example, Patent Document 6: Japanese Patent Application Laid-open No. 2002-85966). However, with this method, each of the carbon dioxide gas absorption and elimination must be carried out at a temperature of several hundred degrees, and hence there has been a problem that much energy must be inputted for the carbon dioxide recovery. That is, many methods have been known hitherto, but many problems remain with such processes in which carbon dioxide gas is absorbed and recovered, and then eliminated to obtain carbon dioxide gas.

A case in which carbon dioxide is inserted into a tin-methoxide linkage of dimethyltin dimethoxide has been reported (see, for example, Non-Patent Document 1: J. Am. Chem. Soc., 121 (1999), 3793-3794). In this case, it is stated that the matter in which the carbon dioxide is inserted into the dimethyltin dimethoxide is present in supercritical carbon dioxide, and that carbon dioxide is produced in an excess (in this case, 4 equivalents) based on the tin atoms contained in the dimethyltin dimethoxide. Furthermore, it is stated that there is production even with a 4° C. saturated carbon dioxide solution, but it is stated that at the same time the product is unstable at room temperature with carbon dioxide being discharged, and hence carbon dioxide recovery and reuse has not been accomplished.

Furthermore, a case in which carbon dioxide is inserted into a tin-methoxide linkage of 1,3-dimethoxytetrabutylstannoxane has been reported (see, for example, Non-Patent Document 2: Applied Catalysis A: General, 255 (2003), 93-99). In this case, the 1,3-dimethoxytetrabutylstannoxane is reacted with carbon dioxide at room temperature and atmospheric pressure so as to obtain solid 1-methoxy-3-methylcarbonatetetrabutylstannoxane. However, this solid is produced only in structural identification, and a method in which the solid is utilized has not been accomplished. As an example in which the reaction product between 1,3-dimethoxytetrabutylstannoxane and carbon dioxide is utilized, there is a method previously disclosed by the present applicants (see, for example, Patent Document 9: WO 03-055840), but this is merely the method in which the 1,3-dimethoxytetrabutylstannoxane is put into a high pressure vessel and reacted with carbon dioxide, so as to produce a carbonate in the high pressure vessel. The present invention is a result of further assiduous studies with an objective of realizing a composition for recovery utilization and/or transfer by making a specified tin compound contain carbon dioxide in a specified ratio, and is completely different to the above art.

Related to the above, in recent years there have been disclosed carbonate production processes in which carbon dioxide is used as a starting material (see, for example, Patent Document 8: Japanese Patent No. 3385359, Patent Document 9: WO 03-055840). In such a carbonate production processes in which carbon dioxide is used as a starting material, the reaction equilibrium is biased to the reactant system side, and hence in general high-pressure carbon dioxide is used, and in many cases supercritical carbon dioxide is used (see, for example, the examples in Patent Document 8: Japanese Patent No. 3385359); the amount of carbon dioxide used in the reaction is very low, unused carbon dioxide being discharged. Moreover, the present inventors have disclosed a method in which the carbon dioxide is not made to be supercritical but rather carbon dioxide at a relatively low pressure is used (see, for example, Patent Document 9: WO 03-055840), but it is merely stated that if the carbon dioxide is subjected to reaction at high pressure then the carbon dioxide goes to waste upon returning to normal pressure, and there are no cases in which recovery and reuse of the unreacted carbon dioxide is described.

The carbon dioxide discharged from such a carbonate production process in which carbon dioxide is used as a starting material is at normal pressure; as a process for reusing such carbon dioxide discharged at normal pressure, an example is a method in which the carbon dioxide is used after having been re-pressurized using a compressor or the like as used in a supercritical carbon dioxide extraction system. With this method, the carbon dioxide at approximately normal pressure must be pressurized to at least several MPa. As compared to the carbon dioxide used in the reaction, there is much more unreacted carbon dioxide that is discharged and must be re-pressurized (in many cases at least several tens of times as much), and hence a very large compressor is required, and moreover much electrical energy must be inputted to drive the compressor and to use a cooler to remove heat produced when compressing the carbon dioxide. This equipment and input of electrical energy causes a worsening of the cost competitiveness of the carbonate production, so that the carbonate production is not worth implementing industrially, and hence the above has not been implemented as a carbonate production process. Moreover, in the case that the reaction system contains a low-boiling alcohol (e.g. methanol) or a low-boiling carbonate (e.g. dimethyl carbonate), the carbon dioxide discharged from the high pressure state contains much of this low-boiling alcohol or low-boiling carbonate, and hence this low-boiling matter (low-boiling alcohol or low-boiling carbonate) may partially liquefy when the discharged carbon dioxide is re-pressurized, and to maintain the compressor performance, it may be necessary to control withdrawal of the liquefied low-boiling matter, so that the apparatus for maintaining the compressor performance becomes very difficult.

Patent Document 1: Japanese Patent No. 2809368
Patent Document 2: Japanese Patent Application Laid-open No. 2003-261315
Patent Document 3: Japanese Patent Application Laid-open No. 5-184864
Patent Document 4: Japanese Patent Application Laid-open No. 2004-344703
Patent Document 5: Japanese Patent Application Laid-open No. 2002-126439
Patent Document 6: Japanese Patent Application Laid-open No. 2002-85966
Patent Document 7: Japanese Patent Application Laid-open No. 2003-192643
Patent Document 8: Japanese Patent No. 3385359
Patent Document 9: WO 03-055840
Non-Patent Document 1: J. Am. Chem. Soc., 121 (1999), 3793-3794
Non-Patent Document 2: Applied Catalysis A: General, 255 (2003), 93-99

DISCLOSURE OF INVENTION

Problems to be Solved by the Invention

It is an object of the present invention to provide a mixture in which gaseous carbon dioxide is fixed that enables the carbon dioxide to be recovered and utilized, and further provide such a mixture that can be transferred as a liquid component. It is another object of the present invention to provide a process in which such a mixture is used, so as to effectively recycle carbon dioxide-containing gas discharged from a carbonate production step, and produce a carbonate efficiently and continuously. It is a further object to use the present invention to enable carbon dioxide-containing gas that has conventionally often been discharged into the atmosphere to be recovered and reused, so as to improve the carbon dioxide utilization efficiency.

Means for Solving the Problems

The present inventors carried out assiduous studies to attain the above objects, and as a result accomplished the present invention upon discovering that a mixture comprising a specified tin compound and carbon dioxide in a specified ratio is very useful for this.

The present invention provides:

[1] a mixture for transferring carbon dioxide, comprising:
an alkyltin alkoxide composition containing an alkyltin alkoxide and a carbon dioxide complex of the alkyltin alkoxide; and
carbon dioxide;
wherein taking the number of mols of tin atoms in the alkyltin alkoxide and/or the carbon dioxide complex of the alkyltin alkoxide contained in the mixture to be Z,
taking carbon dioxide incorporated in the carbon dioxide complex of the alkyltin alkoxide, and carbon dioxide contained in the mixture to be $(CO_2)$,
and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide,
in a relationship $Z:(CO_2)_x:(OR)_y$, a molar proportion represented by x is in a range of from 0.1 to 2, and a molar proportion represented by y is in a range of from 0.5 to 2,
[2] the mixture according to item [1], wherein the mixture is obtained by absorbing gaseous carbon dioxide into the alkyltin alkoxide composition, and bringing about chemical reaction,
[3] the mixture according to item [1] or [2], wherein each of the R groups is an aliphatic group,
[4] the mixture according to any one of items [1] to [3], wherein each of the R groups is an alkyl group having from 1 to 6 carbon atoms,
[5] the mixture according to any one of items [1] to [4], wherein each of the R groups is an alkyl group having from 4 to 6 carbon atoms,
[6] the mixture according to item [2], wherein the chemical reaction is brought about at a pressure in a range of from normal pressure to 1 MPa,
[7] the mixture according to item [2], wherein the chemical reaction is brought about at a temperature in a range of from −40 to 80° C.,
[8] the mixture according to item [2], wherein the alkyltin alkoxide composition is in a liquid state when the gaseous carbon dioxide is absorbed therein,
[9] the mixture according to any one of items [1] to [8], wherein the mixture is transferred at a temperature in a range of from −40 to 80° C.,
[10] the mixture according to any one of items [1] to [9], wherein the alkyltin alkoxide composition contains a tetraalkyldialkoxydistannoxane and/or a dialkyltin dialkoxide,
[11] the mixture according to item [10], wherein a molar ratio between the tetraalkyldialkoxydistannoxane and the dialkyltin dialkoxide contained in the alkyltin alkoxide composition is in a range of from 0:100 to 80:20,
[12] the mixture according to item [10] or [11], wherein the mixture further contains a carbonate, the content of the carbonate being less than 20 mol % based on the number of mols of the tetraalkyldialkoxydistannoxane in the alkyltin alkoxide composition,
[13] the mixture according to any one of items [10] to [12], wherein the tetraalkyldialkoxydistannoxane is a tetraalkyldialkoxydistannoxane represented by following general formula (1):

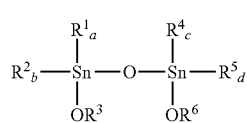

(1)

wherein $R^1$, $R^2$, $R^4$, and $R^5$ independently represent an aliphatic group or an aralkyl group, $R^3$ and $R^6$ independently represent an aliphatic group or an aralkyl group, a and b are integers from 0 to 2 with a+b=2, and c and d are integers from 0 to 2 with c+d=2,

[14] the mixture according to any one of items [10] to [12], wherein the dialkyltin dialkoxide is a dialkyltin dialkoxide represented by following general formula (2)

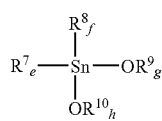

(2)

wherein $R^7$ and $R^8$ independently represent an aliphatic group or an aralkyl group, $R^9$ and $R^{10}$ independently represents an aliphatic group or an aralkyl group, e and f are integers from 0 to 2 with e+f=2, and g and h are integers from 0 to 2 with g+h=2,

[15] the mixture according to any one of items [1] to [14], wherein the alkyltin alkoxide composition is an alkyltin alkoxide composition containing a monomer, aggregate, or polymeric component of at least one dialkyltin alkoxide,

[16] a carbonate production process, comprising reacting the mixture according to item [1] with carbon dioxide,

[17] the carbonate production process according to item [16], comprising the steps of:

step 1: obtaining a mixture comprising carbon dioxide and an alkyltin alkoxide composition containing a carbon dioxide complex of an alkyltin alkoxide obtained by reacting the alkyltin alkoxide with gaseous carbon dioxide, wherein taking the number of mols of tin atoms in the alkyltin alkoxide and/or the carbon dioxide complex of the alkyltin alkoxide contained in the mixture to be Z, taking carbon dioxide incorporated in the carbon dioxide complex of the alkyltin alkoxide, and carbon dioxide contained in the mixture to be ($CO_2$), and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide, in the relationship $Z:(CO_2)_x:(OR)_y$, a molar proportion represented by x is in a range of from 0.1 to 2, and a molar proportion represented by y is in a range of from 0.5 to 2;

step 2: transferring the mixture in a liquid state into a carbonate synthesis step;

step 3: obtaining a reaction liquid containing a carbonate from the mixture under a presence of carbon dioxide; and step 4: separating out carbon dioxide as a gaseous component from the reaction liquid,

[18] the carbonate production process according to item [17], further comprising: after step 4:

step 5: recycling the separated out gaseous carbon dioxide into step 1,

[19] the carbonate production process according to item [18], further comprising: after step 5:

step 6: separating out the carbonate from the reaction liquid from which the carbon dioxide has been separated out in step 4, so as to obtain a residual liquid;

step 7: reacting the residual liquid with an alcohol, so as to obtain the alkyltin alkoxide composition; and step 8: recycling the alkyltin alkoxide composition into step 1,

[20] the carbonate production process according to item [19], wherein the alcohol is an alcohol represented by following formula (3):

$$R^{11}OH \qquad (3)$$

wherein $R^{11}$ has the same definition as R in the OR groups in the mixture in step 1,

[21] a carbon dioxide recovery utilization method comprising:

heating and/or subjecting to reduced pressure the mixture according to item [1] so as to eliminate carbon dioxide, and utilizing the eliminated carbon dioxide, [22] a process for producing a dry gaseous carbon dioxide, comprising obtaining as a liquid phase component the mixture according to item [1], the mixture being a mixture obtained by continuously supplying gaseous carbon dioxide into a reactor and bringing about chemical reaction, and simultaneously continuously withdrawing a gas phase portion from the reactor, so as to obtain dry gaseous carbon dioxide having a lower water content than the continuously supplied gaseous carbon dioxide, [23] a method for transferring carbon dioxide, comprising transferring the mixture according to item [1] in a liquid state, [24] the method for transferring according to item [23], wherein the mixture is transferred at a temperature in a range of from −40 to 80° C.

Advantageous Effects of the Invention

By using the mixture according to the present invention, carbon dioxide can be transferred as a liquid mixture, and furthermore carbon dioxide obtained from the mixture contains substantially no water. Moreover, the mixture according to the present invention can easily be obtained by reacting carbon dioxide gas and an alkyltin alkoxide composition together, and hence can be used as a carbon dioxide recovery utilization mixture with good efficiency. The present invention is thus very useful industrially.

Figure 1:
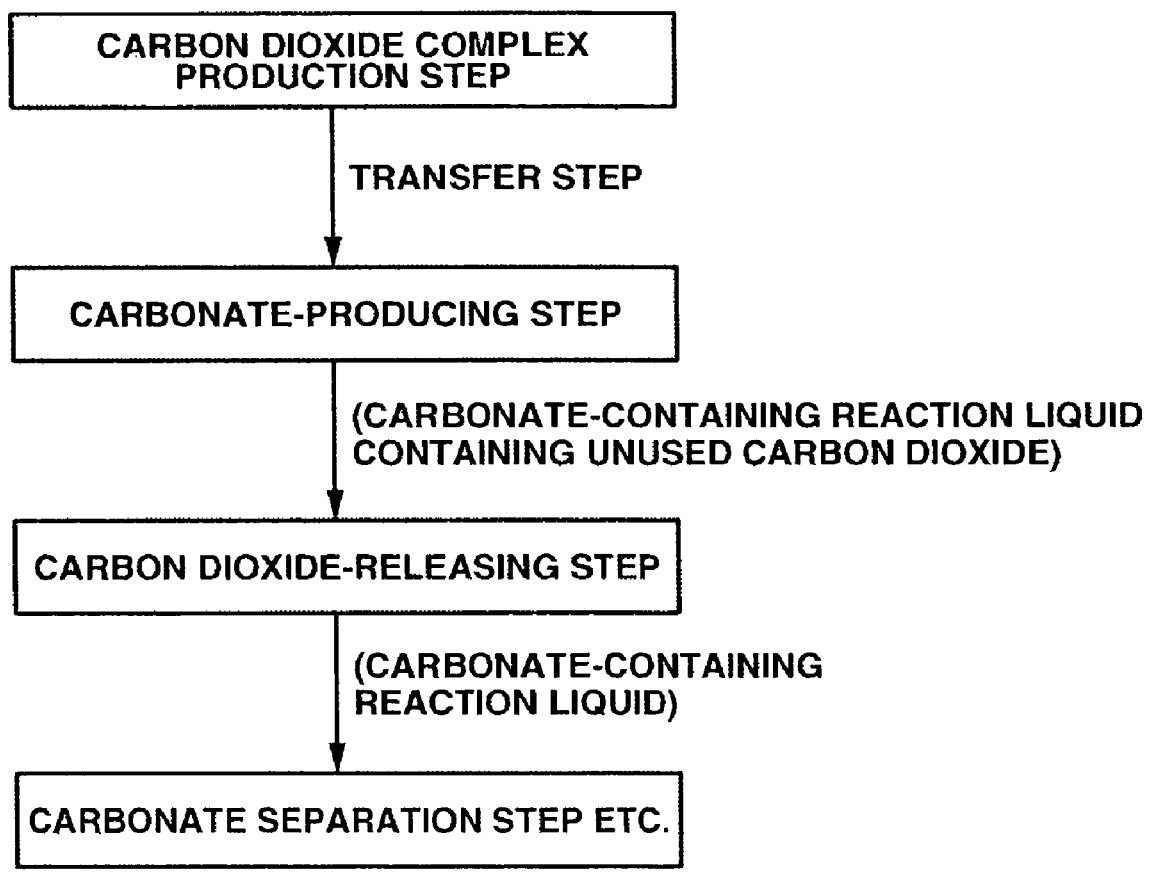
FIG. 1 illustrates a flow diagram of carbonate production using a mixture of the present invention.

DESCRIPTION OF REFERENCE NUMERALS 110, 180: distillation column; 120, 240, 340, 440: column reactor; 130, 160, 170: thin film evaporator; 140: carbon dioxide complex production apparatus; 150, 540: autoclave; 111, 121, 181: reboiler; 112, 132, 172, 182: condenser; 131, 162, 341, 442: cooler; 141: booster pump; 163, 166: compressor; 220, 164, 165: tank reactor; 1, 13, 14, 22, 26, 28: supply line; 2, 4, 5, 6, 7, 8, 9, 10, 11, 15, 16, 17, 18, 19, 23, 24, 25, 27, 30: transfer line; 3, 20, 29: recovery line; 12, 21: vent line.

BEST MODE FOR CARRYING OUT THE INVENTION

Embodiments of the present invention will now be described with reference to the drawings. The following embodiments are merely illustrative for explaining the present invention, the present invention not being intended to be limited to only these embodiments. So long as the gist of the present invention is not deviated from, the present invention may be implemented in any of various modes.

A mixture according to the present invention is a mixture for recovery utilization and/or transfer of carbon dioxide comprising a specific tin compound and carbon dioxide in a specific ratio. The mixture according to the present invention can be easily obtained from gaseous carbon dioxide and an alkyltin alkoxide composition. Specifically, the mixture according to the present invention is a mixture for transfer or carbon dioxide comprising:

an alkyltin alkoxide composition containing an alkyltin alkoxide and a carbon dioxide complex of the alkyltin alkoxide; and carbon dioxide;

wherein taking the number of mols of tin atoms in the alkyltin alkoxide and/or the carbon dioxide complex of the alkyltin alkoxide contained in the mixture to be Z, taking carbon dioxide incorporated in the carbon dioxide complex of the alkyltin alkoxide, and carbon dioxide contained in the mixture to be $(CO_2)$, and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide, in a relationship $Z:(CO_2)_x:(OR)_y$, a molar proportion represented by x is in a range of from 0.1 to 2, and a molar proportion represented by y is in a range of from 0.5 to 2.

The mixture according to the present invention will now be described in more detail.

The mixture according to the present invention is a mixture containing a carbon dioxide complex of an alkyltin alkoxide composition, and is preferably a mixture containing the carbon dioxide complex of the alkyltin alkoxide composition containing an alkyltin alkoxide represented by formula (1) and/or formula (2) described below.

The term "alkyltin alkoxide" used in the present invention refers to a specific alkyltin alkoxide. Specifically, each such specific alkyltin alkoxide contains at least one tetravalent tin atom in the molecule thereof, the valency being accounted for by tin-alkyl bonds and tin-oxygen bonds (including tin-alkoxy bonds), with there being at least one of each of these bonds in the molecule as the bonds to each tin atom. Note, however, that there may be coordination of other molecules to a tin atom from outside the molecule so long as the object of the present invention is not affected. Examples of such coordination from outside the molecule includes association through donor coordination with an alcohol or between alkyltin alkoxides, and coordination of carbon dioxide, although there is no limitation thereto.

The alkyl group forming each of the above tin-alkyl bonds refers to an aliphatic or aralkyl group. Examples thereof include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. In the case that there are a plurality of alkyl groups bonded to a tin atom, the alkyl groups may be the same as one another, or in some cases may be different. Of the above alkyl groups, one selected from an n-butyl group and an n-octyl group is preferable.

An alkyl group forming an alkoxy group (a group comprising an oxygen-alkyl linkage) forming each of the tin-alkoxy bonds among the above tin-oxygen bonds refers to an aliphatic or aralkyl group. Examples thereof are straight chain or branched aliphatic groups having from 1 to 12 carbon atoms, cycloalkyl groups having from 5 to 12 carbon atoms, straight chain or branched alkenyl groups having from 2 to 12 carbon atoms, and aralkyl groups having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or the alkyl group may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. An alkyl group having from 1 to 6 carbon atoms is particularly preferable. In the case that the number of carbon atoms is low, the stability and the fluidity for transfer may worsen, and in the case of having a substituent on the carbon atom adjacent to the oxygen (O) of the alkoxy group, the compound may not be liquid, and hence it is most preferable for this adjacent carbon atom to form a methylene ($CH_2$) structure, most preferable examples of the alkyl group forming the alkoxy group being alkyl groups having from 4 to 6 carbon atoms and in which the carbon atom adjacent to the oxygen forms a methylene structure. In the case that there are a plurality of alkoxy groups bonded to a tin atom, the alkoxy groups may be the same as one another, or in some cases may be different.

Tin-oxygen bonds other than the tin-alkoxy bonds may be any bonds so long as these are bonds that do not affect the object of the present invention. Preferable such bonds are tin-oxygen bonds forming a tin-oxygen-tin linkage.

The term "alkyltin alkoxide composition" used in the present invention refers to a composition that contains an alkyltin alkoxide as described above. A preferable alkyltin alkoxide composition is an alkyltin alkoxide composition that contains a tetraalkyldialkoxydistannoxane represented by formula (1) and/or a dialkyltin dialkoxide represented by formula (2).

Following is a more detailed description of each alkyltin alkoxide used in the present invention, giving examples.

The term "tetraalkyldialkoxydistannoxane" used in the present invention refers to a tetraalkyldialkoxydistannoxane represented by following formula (1); a representative structural formula is shown in following formula (1), but the tetraalkyldialkoxydistannoxane may be a monomer, an aggregate, a multimer, or a polymer:

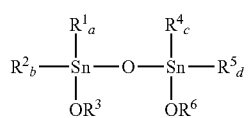
(1)

wherein $R^1$, $R^2$, $R^4$, and $R^5$ independently represent an aliphatic group or an aralkyl group, $R^3$ and $R^6$ independently represent an aliphatic group or an aralkyl group, a and b are integers from 0 to 2 with a+b=2, and c and d are integers from 0 to 2 with c+d=2.

Examples of each of $R^1$, $R^2$, $R^4$, and $R^5$ in the tetraalkyldialkoxydistannoxane of formula (1) include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. A straight chain or branched alkyl group having from 1 to 8 carbon atoms is particularly preferable. A group having more carbon atoms than above may be used, but the fluidity may worsen, or the productivity may be impaired. $R^1$, $R^2$, $R^4$, and $R^5$ in formula (1) may be the same as one another, or in some cases may be different.

Each of $R^3$ and $R^6$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. $R^3$ and $R^6$ in formula (1) may be the same as one another, or in some cases may be different.

Examples of the tetraalkyldialkoxydistannoxane represented by formula (1) include tetraalkyldialkoxydistannoxanes and tetraalkyldiaralkyloxydistannoxanes such as 1,1,3,3-tetrabutyl-1,3-dimethoxy-distannoxane, 1,1,3,3-tetrabutyl-1,3-diethoxy-distannoxane, 1,1,3,3-tetrabutyl-1,3-dipropoxy-distannoxane (isomers), 1,1,3,3-tetrabutyl-1,3-dibutoxy-distannoxane (isomers), 1,1,3,3-tetrabutyl-1,3-dipentyloxy-distannoxane (isomers), 1,1,3,3-tetrabutyl-1,3-dihexyloxy-distannoxane (isomers), 1,1,3,3-tetrabutyl-1,3-diheptyloxy-distannoxane, 1,1,3,3-tetrabutyl-1,3-dibenzyloxy-distannoxane, 1,1,3,3-tetraoctyl-1,3-dimethoxy-distannoxane, 1,1,3,3-tetraoctyl-1,3-diethoxy-distannoxane, 1,1,3,3-tetraoctyl-1,3-dipropoxy-distannoxane (isomers), 1,1,3,3-tetraoctyl-1,3-dibutoxy-distannoxane (isomers), 1,1,3,3-tetraoctyl-1,3-dipentyloxy-distannoxane (isomers), 1,1,3,3-tetraoctyl-1,3-dihexyloxy-distannoxane (isomers), 1,1,3,3-tetraoctyl-1,3-diheptyloxy-distannoxane (isomers), and 1,1,3,3-tetraoctyl-1,3-dibenzyloxy-distannoxane. One may be selected from the above group, or a mixture selected from the above group may be used.

Of the tetraalkyldialkoxydistannoxanes represented by formula (1), one in which each of the groups $R^1$, $R^2$, $R^4$, and $R^5$ is selected from an n-butyl group and an n-octyl group is preferable, particularly preferable examples being ones in which each of the groups $R^3$ and $R^6$ is an alkyl group having from 1 to 6 carbon atoms. In the case that the number of carbon atoms in the $R^3$ group or the $R^6$ group is low, the stability and the fluidity for transfer may worsen, and in the case of having a substituent on the carbon atom adjacent to the oxygen (O) of the $OR^3$ or $OR^6$ group formed from the $R^3$ or $R^6$ group, the compound may not be liquid, and hence it is most preferable for this adjacent carbon atom to form a methylene ($CH_2$) structure, most preferable examples being ones in which each of the groups $R^3$ and $R^6$ is an alkyl group having from 4 to 6 carbon atoms and in which the carbon atom adjacent to the oxygen forms a methylene structure. Most preferable such examples include 1,1,3,3-tetra-(n-butyl)-1,3-di-(n-butoxy)-distannoxane, 1,1,3,3-tetra-(n-butyl)-1,3-di-(n-pentyloxy)-distannoxane, 1,1,3,3-tetra-(n-butyl)-1,3-bis-(3-methylbutoxy)-distannoxane, 1,1,3,3-tetra-(n-butyl)-1,3-di-(n-hexyloxy)-distannoxane, 1,1,3,3-tetra-(n-butyl)-1,3-bis-(2-ethylbutoxy)-distannoxane, 1,1,3,3-tetra-(n-octyl)-1,3-di-(n-butoxy)-distannoxane, 1,1,3,3-tetra-(n-octyl)-1,3-di-(n-pentyloxy)-distannoxane, 1,1,3,3-tetra-(n-octyl)-1,3-bis-(3-methylbutoxy)-distannoxane, 1,1,3,3-tetra-(n-octyl)-1,3-di-(n-hexyloxy)-distannoxane, and 1,1,3,3-tetra-(n-octyl)-1,3-bis-(2-ethylbutoxy)-distannoxane.

The term "dialkyltin dialkoxide" used in the present invention refers to a dialkyltin dialkoxide represented by following formula (2); a representative structural formula is shown in following formula (2), but the dialkyltin dialkoxide may be a monomer, an aggregate, a multimer, or a polymer:

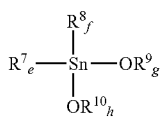

(2)

wherein $R^7$ and $R^8$ independently represent an aliphatic group or an aralkyl group, $R^9$ and $R^{10}$ independently represent an aliphatic group or an aralkyl group, e and f are integers from 0 to 2 with e+f=2, and g and h are integers from 0 to 2 with g+h=2.

Examples of each of $R^7$ and $R^8$ in the dialkyltin dialkoxide of formula (2) include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. A straight chain or branched alkyl group having from 1 to 8 carbon atoms is particularly preferable. A group having more carbon atoms than above may be used, but the fluidity may worsen, or the productivity may be impaired. $R^7$ and $R^8$ in formula (2) may be the same as one another, or in some cases may be different.

Each of $R^9$ and $R^{10}$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. $R^9$ and $R^{10}$ in formula (2) may be the same as one another, or in some cases may be different.

Examples of such a dialkyltin dialkoxide include dialkyl-dialkoxy-tin compounds and dialkyl-diaralkyloxy-tin compounds such as dibutyl-dimethoxy-tin, dibutyl-diethoxy-tin, dibutyl-dipropoxy-tin (isomers), dibutyl-dibutoxy-tin (isomers), dibutyl-dipentyloxy-tin (isomers), dibutyl-dihexyloxy-tin (isomers), di butyl-diheptyloxy-tin, di butyl-dibenzyloxy-tin, dioctyl-dimethoxy-tin, dioctyl-diethoxy-tin, dioctyl-dipropoxy-tin (isomers), dioctyl-dibutoxy-tin (isomers), dioctyl-dipentyloxy-tin (isomers), dioctyl-dihexyloxy-tin (isomers), dioctyl-diheptyloxy-tin (isomers), and dioctyl-dibenzyloxy-tin. One may be selected from the above group, or a mixture selected from the above group may be used.

Of the dialkyltin dialkoxides represented by formula (2), one in which each of the groups $R^7$ and $R^8$ is selected from an n-butyl group and an n-octyl group is preferable, particularly preferable examples being ones in which each of the groups $R^9$ and $R^{10}$ is an alkyl group having from 1 to 6 carbon atoms. In the case that the number of carbon atoms in the $R^9$ group or the $R^{10}$ group is low, the stability and the fluidity for transfer may worsen, and furthermore in the case of having a substituent on the carbon atom adjacent to the oxygen (O) of the $OR^9$ or $OR^{10}$ group formed from the $R^9$ or $R^{10}$ group, the compound may not be liquid, and hence it is most preferable for this adjacent carbon atom to form a methylene ($CH_2$) structure, most preferable examples being ones in which each of the groups $R^9$ and $R^{10}$ is an alkyl group having from 4 to 6 carbon atoms and in which the carbon atom adjacent to the oxygen forms a methylene structure. Most preferable such examples include di-(n-butyl)-di-(n-butoxy)-tin, di-(n-butyl)-di-(n-pentyloxy)-tin, di-(n-butyl)-bis-(3-methylbutoxy)-tin, di-(n-butyl)-di-(n-hexyloxy)-tin, di-(n-butyl)-bis-(2-ethylbutoxy)-tin, di-(n-octyl)-di-(n-butoxy)-tin, di-(n-octyl)-di-(n-pentyloxy)-tin, di-(n-octyl)-di-(n-hexyloxy)-tin, di-(n-octyl)-bis-(3-methylbutoxy)-tin, and di-(n-octyl)-bis-(2-ethylbutoxy)-tin.

As an alkyltin alkoxide, a trialkyltin alkoxide as represented by following formula (4) can also be used in the present invention:

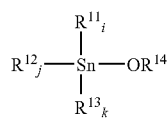

(4)

(wherein $R^{11}$, $R^{12}$, and $R^{13}$ independently represent an aliphatic group or an aralkyl group, $R^{14}$ represents an aliphatic group or an aralkyl group, and i, j, and k are integers from 0 to 3 with i+j+k=3.

Examples of each of $R^{11}$, $R^{12}$, and $R^{13}$ in the trialkyltin alkoxide of formula (4) include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. A straight chain or branched alkyl group having from 1 to 8 carbon atoms is particularly preferable. A group having more carbon atoms than above may be used, but the fluidity may worsen, or the productivity may be impaired. $R^{11}$, $R^{12}$, and $R^{13}$ in formula (4) may be the same as one another, or in some cases may be different.

$R^{14}$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable.

Examples of such a trialkyltin alkoxide include trialkyl-alkoxy-tin compounds and trialkyl-aralkyloxy-tin compounds such as tributyl-methoxy-tin, tributyl-ethoxy-tin, tributyl-propoxy-tin (isomers), tributyl-butoxy-tin (isomers), tributyl-pentyloxy-tin (isomers), tributyl-hexyloxy-tin (isomers), tributyl-heptyloxy-tin, tributyl-benzyloxy-tin, trioctyl-methoxy-tin, trioctyl-ethoxy-tin, trioctyl-propoxy-tin (isomers), trioctyl-butoxy-tin (isomers), trioctyl-pentyloxy-tin (isomers), trioctyl-hexyloxy-tin (isomers), trioctyl-heptyloxy-tin (isomers), and trioctyl-benzyloxy-tin. One may be selected from the above group, or a mixture selected from the above group may be used.

Of the trialkyltin alkoxides represented by formula (4), one in which each of the groups $R^{11}$, $R^{12}$, and $R^{13}$ is selected from an n-butyl group and an n-octyl group is preferable, particularly preferable examples being ones in which the $R^{14}$ group is an alkyl group having from 1 to 6 carbon atoms. In the case that the number of carbon atoms in the $R^{14}$ group is low, the stability and the fluidity for transfer may worsen, and furthermore in the case of having a substituent on the carbon atom adjacent to the oxygen (O) of the $OR^{14}$ group formed from the $R^{14}$ group, the compound may not be liquid, and hence it is most preferable for this adjacent carbon atom to form a methylene ($CH_2$) structure, most preferable examples being ones in which the $R^{14}$ group is an alkyl group having from 4 to 6 carbon atoms and in which the carbon atom adjacent to the oxygen forms a methylene structure. Most preferable such examples include tri-(n-butyl)-(n-butoxy)-tin, tri-(n-butyl)-(n-pentyloxy)-tin, tri-(n-butyl)-(3-methylbutoxy)-tin, tri-(n-butyl)-(n-hexyloxy)-tin, tri-(n-butyl)-(2-ethylbutoxy)-tin, tri-(n-octyl)-(n-butoxy)-tin, tri-(n-octyl)-(n-pentyloxy)-tin, tri-(n-octyl)-(n-hexyloxy)-tin, tri-(n-octyl)-(3-methylbutoxy)-tin, and tri-(n-octyl)-(2-ethylbutoxy)-tin.

As an alkyltin alkoxide, a monoalkyltin alkoxide can also be used in the present invention. It is difficult to identify the structure of such a monoalkyltin alkoxide, but the monoalkyltin alkoxide may be represented by following formula (5) and/or formula (6);

(5)

(6)

wherein $R^{15}$ and $R^{19}$ independently represent an aliphatic group or an aralkyl group, $R^{16}$, $R^{17}$, $R^{18}$, and $R^{20}$ independently represent an aliphatic group or an aralkyl group, and m, n, and p are integers from 0 to 3 with m+n+p=3.

Examples of $R^{15}$ in the monoalkyltin alkoxide represented by formula (5) include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. A straight chain or branched alkyl group having from 1 to 8 carbon atoms is particularly preferable. A group having more carbon atoms than above may be used, but the fluidity may worsen, or the productivity may be impaired.

Each of $R^{16}$, $R^{17}$, and $R^{18}$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable.

Examples of such a monoalkyltin alkoxide include alkyl-tri-alkoxy-tin compounds and alkyl-tri-aralkyloxy-tin compounds such as butyl-trimethoxy-tin, butyl-tri-ethoxy-tin, butyl-tripropoxy-tin (isomers), butyl-tri-butoxy-tin (isomers), butyl-tri-pentyloxy-tin (isomers), butyl-tri-hexyloxy-tin (isomers), butyl-tri-heptyloxy-tin (isomers), butyl-tri-benzyloxy-tin, octyl-tri-methoxy-tin, octyl-tri-ethoxy-tin, octyl-tri-propoxy-tin (isomers), octyl-tri-butoxy-tin (isomers), octyl-tri-pentyloxy-tin (isomers), octyl-tri-hexyloxy-tin (isomers), octyl-tri-heptyloxy-tin (isomers), and octyl-tri-benzyloxy-tin. One may be selected from the above group, or a mixture selected from the above group may be used.

Of the monoalkyltin alkoxides represented by formula (5), one in which the $R^{15}$ group is selected from an n-butyl group and an n-octyl group is preferable, particularly preferable examples being ones in which each of the groups $R^{16}$, $R^{17}$, and $R^{18}$ is an alkyl group having from 1 to 6 carbon atoms. In the case that the number of carbon atoms in the $R^{16}$ group, the $R^{17}$ group, or the $R^{18}$ group is low, the stability and the fluidity for transfer may worsen, and furthermore in the case of having a substituent on the carbon atom adjacent to the oxygen (O) of the $OR^{16}$, $OR^{17}$, or $OR^{10}$ group formed from the $R^{16}$, $R^{17}$, or $R^{18}$ group, the compound may not be liquid, and hence it is most preferable for this adjacent carbon atom to form a methylene ($CH_2$) structure, most preferable examples being ones in which each of the groups $R^{16}$, $R^{17}$, and $R^{18}$ is an alkyl group having from 4 to 6 carbon atoms and in which the carbon atom adjacent to the oxygen forms a methylene structure. Most preferable such examples include (n-butyl)-tri-(n-butoxy)-tin, (n-butyl)-tri-(n-pentyloxy)-tin, (n-butyl)-tris-(3-methyl butoxy)-tin, (n-butyl)-tri-(n-hexyloxy)-tin, (n-butyl)-tris-(2-ethylbutoxy)-tin, (n-octyl)-tri-(n-butoxy)-tin, (n-octyl)-tri-(n-pentyloxy)-tin, (n-octyl)-tri-(n-hexyloxy)-tin, (n-octyl)-tris-(3-methylbutoxy)-tin, and (n-octyl)-tris-(2-ethylbutoxy)-tin.

Examples of $R^{19}$ in the monoalkyltin alkoxide represented by formula (6) include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. A straight chain or branched alkyl group having from 1 to 8 carbon atoms is particularly preferable. A group having more carbon atoms than above may be used, but the fluidity may worsen, or the productivity may be impaired.

$R^{20}$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable.

Examples of such a monoalkyltin alkoxide include alkyl-alkoxy-tin oxides and alkyl-aralkyloxy-tin oxides such as butyl-methoxy-tin oxide, butyl-ethoxy-tin oxide, butyl-propoxy-tin oxide (isomers), butyl-butoxy-tin oxide (isomers), butyl-pentyloxy-tin oxide (isomers), butyl-hexyloxy-tin oxide (isomers), butyl-heptyloxy-tin oxide (isomers), butyl-benzyloxy-tin oxide, octyl-methoxy-tin oxide, octyl-ethoxy-tin oxide, octyl-propoxy-tin oxide (isomers), octyl-butoxy-tin oxide (isomers), octyl-pentyloxy-tin oxide (isomers), octyl-hexyloxy-tin oxide (isomers), octyl-heptyloxy-tin oxide (isomers), and octyl-benzyloxy-tin oxide. One may be selected from the above group, or a mixture selected from the above group may be used.

Of the monoalkyltin alkoxides represented by formula (6), one in which the $R^{19}$ group is selected from an n-butyl group and an n-octyl group is preferable, particularly preferable examples being ones in which the $R^{20}$ group is an alkyl group having from 1 to 6 carbon atoms. In the case that the number of carbon atoms in the $R^{20}$ group is low, the stability and the fluidity for transfer may worsen, and furthermore in the case of having a substituent on the carbon atom adjacent to the oxygen (O) of the $OR^{20}$ group formed from the $R^{20}$ group, the compound may not be liquid, and hence it is most preferable for this adjacent carbon atom to form a methylene ($CH_2$) structure, most preferable examples being ones in which the $R^{20}$ group is an alkyl group having from 4 to 6 carbon atoms and in which the carbon atom adjacent to the oxygen forms a methylene structure. Most preferable such examples include (n-butyl)-(n-butoxy)-tin oxide, (n-butyl)(n-pentyloxy)-tin oxide, (n-butyl)-(3-methylbutoxy)-tin oxide, (n-butyl)-tin-(n-hexyloxy)-tin oxide, (n-butyl)-(2-ethylbutoxy)-tin oxide, (n-octyl)-(n-butoxy)-tin oxide, (n-octyl)-(n-pentyloxy)-tin oxide, (n-octyl)-(n-hexyloxy)-tin oxide, (n-octyl)-(3-methylbutoxy)-tin oxide, and (n-octyl)-(2-ethylbutoxy)-tin oxide.

As an alkyltin alkoxide, a trialkyl-trialkoxy-distannoxane as shown in following formula (7) can also be used in the present invention. The term "trialkyl-trialkoxy-distannoxane" used in the present invention refers to a trialkyl-trialkoxy-distannoxane represented by following formula (7); a representative structural formula is shown in following formula (7), but the trialkyl-trialkoxy-distannoxane may be a monomer, an aggregate, a multimer, or a polymer;

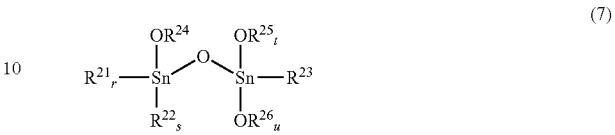

(7)

wherein $R^{21}$, $R^{22}$, and $R^{23}$ independently represent an aliphatic group or an aralkyl group, $R^{24}$, $R^{25}$, and $R^{26}$ independently represent an aliphatic group or an aralkyl group, r and s are integers from 0 to 2 with r+s=2, and t and u are integers from 0 to 2 with t+u=2.

Examples of each of $R^{21}$, $R^{22}$, and $R^{23}$ in the trialkyl-trialkoxy-distannoxane of formula (7) include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. A straight chain or branched alkyl group having from 1 to 8 carbon atoms is particularly preferable. A group having more carbon atoms than above may be used, but the fluidity may worsen, or the productivity may be impaired. $R^{21}$, $R^{22}$, and $R^{23}$ in formula (7) may be the same as one another, or in some cases may be different.

Each of $R^{24}$, $R^{25}$, and $R^{26}$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. $R^{24}$, $R^{25}$, and $R^{26}$ in formula (7) may be the same as one another, or in some cases may be different.

Examples of the trialkyl-trialkoxy-distannoxane represented by formula (7) include trialkyl-trialkoxy-distannoxanes and trialkyl-triaralkyloxy-distannoxanes such as 1,1,3-tributyl-1,3,3-trimethoxy-distannoxane, 1,1,3-tributyl-1,3,3-triethoxy-distannoxane, 1,1,3-tributyl-1,3,3-tripropoxy-distannoxane (isomers), 1,1,3-tributyl-1,3,3-tributoxy-distannoxane (isomers), 1,1,3-tributyl-1,3,3-tripentyloxy-distannoxane (isomers), 1,1,3-tributyl-1,3,3-trihexyloxy-distannoxane (isomers), 1,1,3-tributyl-1,3,3-triheptyloxydistannoxane, 1,1,3-tributyl-1,3,3-tribenzyloxy-distannoxane, 1,1,3-trioctyl-1,3,3-trimethoxy-distannoxane, 1,1,3-trioctyl-1,3,3-triethoxy-distannoxane, 1,1,3-trioctyl-1,3,3-tripropoxy-distannoxane (isomers), 1,1,3-trioctyl-1,3,3-tributoxy-distannoxane (isomers), 1,1,3-trioctyl-1,3,3-tripentyloxy-distannoxane (isomers), 1,1,3-trioctyl-1,3,3-trihexyloxy-distannoxane (isomers), 1,1,3-trioctyl-1,3,3-triheptyloxy-distannoxane (isomers), and 1,1,3-tributyl-1,3,3-tribenzyloxy-distannoxane. One may be selected from the above group, or a mixture selected from the above group may be used.

Of the trialkyl-trialkoxy-distannoxanes represented by formula (7), one in which each of the groups $R^{21}$, $R^{22}$, and $R^{23}$ is selected from an n-butyl group and an n-octyl group is preferable, particularly preferable examples being ones in which each of the groups $R^{24}$, $R^{25}$, and $R^{26}$ is an alkyl group having from 1 to 6 carbon atoms. In the case that the number of carbon atoms in the $R^{24}$ group, the $R^{25}$ group, or the $R^{26}$ group is low, the stability and the fluidity for transfer may worsen, and in the case of having a substituent on the carbon atom adjacent to the oxygen (O) of the $OR^{24}$, $OR^{25}$, or $OR^{26}$ group formed from the $R^{24}$, $R^{25}$, or $R^{26}$ group, the compound may not be liquid, and hence it is most preferable for this adjacent carbon atom to form a methylene ($CH_2$) structure, most preferable examples being ones in which each of the groups $R^{24}$, $R^{25}$, and $R^{26}$ is an alkyl group having from 4 to 6 carbon atoms and in which the carbon atom adjacent to the oxygen forms a methylene structure. Most preferable such examples include 1,1,3-tri-(n-butyl)-1,3,3-tri-(n-butoxy)-distannoxane, 1,1,3-tri-(n-butyl)-1,3,3-tri-(n-pentyloxy)-distannoxane, 1,1,3-tri-(n-butyl)-1,3,3-tris-(3-methylbutoxy)-distannoxane, 1,1,3-tri-(n-butyl)-1,3,3-tri-(n-hexyloxy)-distannoxane, 1,1,3-tri-(n-butyl)-1,3,3-tris-(2-ethylbutoxy)-distannoxane, 1,1,3-tri-(n-octyl)-1,3,3-tri-(n-butoxy)-distannoxane, 1,1,3-tri-(n-octyl)-1,3,3-tri-(n-pentyloxy)-distannoxane, 1,1,3-tri-(n-octyl)-1,3,3-tris-(3-methylbutoxy)-distannoxane, 1,1,3-tri-(n-octyl)-1,3,3-tri-(n-hexyloxy)-distannoxane, and 1,1,3-tri-(n-octyl)-1,3,3-tris-(2-ethylbutoxy)-distannoxane.

There may be a mixture of such alkyltin alkoxides, or one alone, and moreover such alkyltin alkoxides may be coordinated or aggregated together. Such alkyltin alkoxides readily exchange ligands, and there may be alkyltin alkoxides that have a structure that is difficult to identify, or that are coordinated or aggregated other than as described above. Note that alkyltin alkoxides that are based on the above stipulation of alkyl groups and alkoxy groups but merely cannot be identified by current analytical techniques may also be used in the present invention.

Next, the carbon dioxide complex of the alkyltin alkoxide used in the present invention will be described.

The term "carbon dioxide complex of alkyltin alkoxide" used in the present invention refers to a specific carbon dioxide complex of an alkyltin alkoxide. Characteristic features of this specific carbon dioxide complex of the alkyltin alkoxide are containing at least one tetravalent tin atom in the molecule thereof, wherein as the bonds to each tin atom the valency is accounted for by tin-alkyl bonds, tin-carbonate linkages, and tin-oxygen bonds (including tin-alkoxy bonds), with there being at least one tin-alkyl bond and at least one tin-carbonate linkage in the molecule. Note, however, that there may also be coordination of other molecules to a tin atom from outside the molecule so long as the object of the present invention is not affected. Examples of such coordination from outside the molecule include association through donor coordination with an alcohol or between alkyltin alkoxides or carbon dioxide complex of an alkyltin alkoxide, and coordination of carbon dioxide, although there is no limitation thereto.

The alkyl group forming each of the above tin-alkyl bonds indicates an aliphatic or aralkyl group. Examples thereof include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. In the case that there are a plurality of alkyl groups bonded to a tin atom, the alkyl groups may be the same as one another, or in some cases may be different. Of the above alkyl groups, one selected from an n-butyl group and an n-octyl group is preferable.

An alkyl group forming an alkoxy group (a group comprising an oxygen-alkyl linkage) forming each of the tin-alkoxy bonds among the above tin-oxygen bonds indicates an aliphatic or aralkyl group. Examples thereof include straight chain or branched aliphatic groups having from 1 to 12 carbon atoms, cycloalkyl groups having from 5 to 12 carbon atoms, straight chain or branched alkenyl groups having from 2 to 12 carbon atoms, and aralkyl groups having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or the alkyl group may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. An alkyl group having from 1 to 6 carbon atoms is particularly preferable. In the case that the number of carbon atoms is low, the stability and the fluidity for transfer may worsen, and in the case of having a substituent on the carbon atom adjacent to the oxygen (O) of the alkoxy group, the compound may not be liquid, and hence it is most preferable for this adjacent carbon atom to form a methylene ($CH_2$) structure, most preferable examples of the alkyl group forming the alkoxy group being alkyl groups having from 4 to 6 carbon atoms and in which the carbon atom adjacent to the oxygen forms a methylene structure. In the case that there are a plurality of alkoxy groups bonded to a tin atom, the alkoxy groups may be the same as one another, or in some cases may be different.

Tin-oxygen bonds other than the tin-alkoxy bonds may be any bonds so long as these are bonds that do not affect the object of the present invention. Preferable such bonds are tin-oxygen bonds forming a tin-oxygen-tin linkage.

A tin-carbonate linkage as described above is a bond that characterizes the carbon dioxide complex of the alkyltin alkoxide used in the present invention. Each such tin-carbonate linkage is a linkage in which a carbon dioxide molecule ($CO_2$) is inserted between the tin atom of a tin-alkoxy bond as described above (i.e. an Sn—OR bond) and the alkoxy group. That is, each tin-carbonate linkage is a linkage characterized as Sn—O—CO—OR. The existence of such a linkage can be confirmed by a combination of publicly known methods such as $^{119}$Sn-NMR, $^{13}$C-NMR, $^{1}$H-NMR, and X-ray structure analysis.

The mixture according to the present invention is a mixture characterized by containing such a carbon dioxide complex of an alkyltin alkoxide. Preferable carbon dioxide complex of the alkyltin alkoxide has a structure in which some or all of the alkoxy group portions of an alkyltin alkoxide that can be used in the present invention as described above are substituted with (or changed to) carbonate linkages as described above.

The carbon dioxide complex of the alkyltin alkoxide used in the present invention is described in more detail below, by giving examples. Preferable such a carbon dioxide complex of the alkyltin alkoxide has a structure in which some or all of the alkoxy group portions of an alkyltin alkoxide that can be used in the present invention as described above are substituted with (or changed to) carbonate linkages as described above. The carbon dioxide complex of the alkyltin alkoxide will thus be described through correspondence with the alkyltin alkoxides described above. Note that although the existence of linkages in the carbon dioxide complex can be confirmed through analysis methods as described above, the structure of the carbon dioxide complex is complicated, and in some cases cannot be identified by current analytical techniques; the carbon dioxide complex in the present invention is not limited to having a structure as in the following examples.

As examples of carbon dioxide complex corresponding to a tetraalkyldialkoxydistannoxane represented by above formula (1), representative structural formulae are shown in following formulae (8), (9), and (10), although the carbon dioxide complex may be a monomer, an aggregate, a multimer, or a polymer;

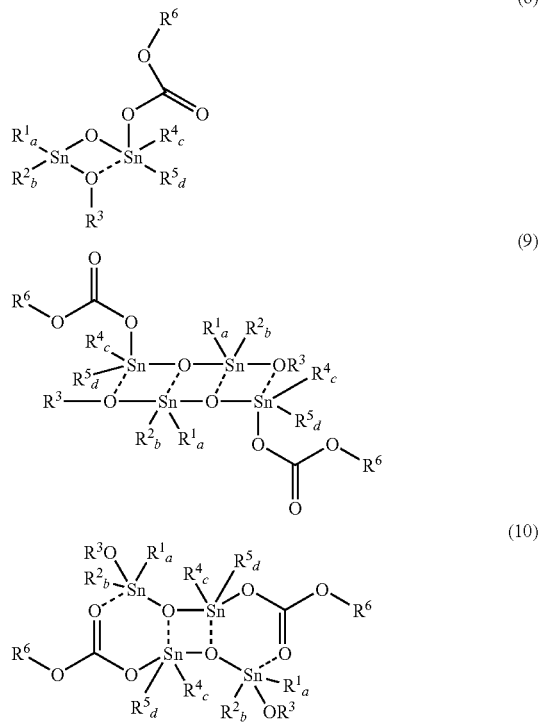

wherein $R^1$, $R^2$, $R^3$, $R^4$, $R^5$, and $R^6$ independently represent respectively $R^1$, $R^2$, $R^3$, $R^4$, $R^5$, and $R^6$ as defined in above formula (1), and a, b, c, and d represent respectively a, b, c, and d as defined in formula (1).

As examples of carbon dioxide complex corresponding to a dialkyltin dialkoxide represented by above formula (2), representative structural formulae are shown in following formulae (11), (12), and (13), although the carbon dioxide complex may be a monomer, an aggregate, a multimer, or a polymer;

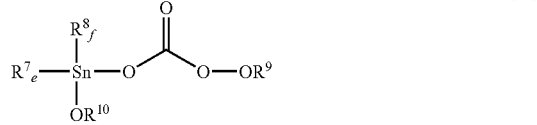

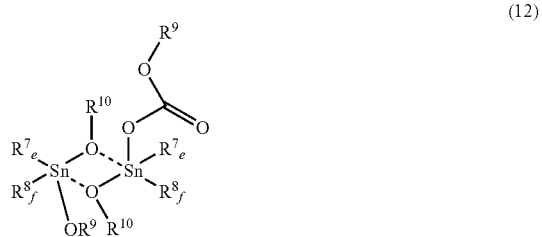

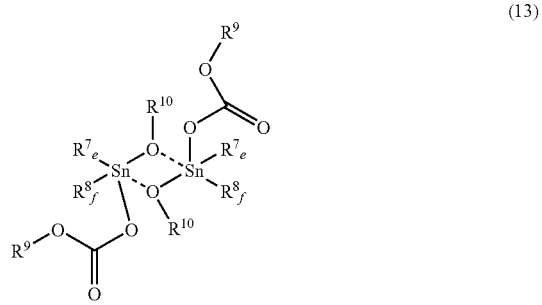

wherein $R^7$, $R^8$, $R^9$, and $R^{10}$ independently represent respectively $R^7$, $R^8$, $R^9$, and $R^{10}$ as defined in above formula (2), and e and f represent respectively e and f as defined in formula (2).

Examples of $R^1$, $R^2$, $R^3$, $R^4$, $R^5$, $R^6$, $R^7$, $R^8$, $R^9$, and $R^{10}$ in the bonded matter represented by above formulae (8) to (13) are as described earlier, examples of the carbon dioxide complex including alkoxy-alkylcarbonate-dialkyl-tin compounds and aralkyloxy-aralkylcarbonate-dialkyl-tin compounds such as methoxy-methylcarbonate-dibutyl-tin, ethoxy-ethylcarbonate-dibutyl-tin, propoxy-propylcarbonate-dibutyl-tin (isomers), butoxy-butylcarbonate-dibutyl-tin (isomers), pentyloxy-pentylcarbonate-dibutyl-tin (isomers), hexyloxy-hexylcarbonate-dibutyl-tin (isomers), heptyloxy-heptylcarbonate-dibutyl-tin (isomers), benzyloxy-benzylcarbonate-dibutyl-tin, methoxy-methylcarbonatedioctyl-tin, ethoxy-ethylcarbonate-dioctyl-tin, propoxy-propylcarbonate-dioctyl-tin (isomers), butoxy-butylcarbonate-dioctyl-tin (isomers), pentyloxy-pentylcarbonate-dioctyl-tin (isomers), hexyloxy-hexylcarbonate-dioctyl-tin (isomers), heptyloxy-heptylcarbonate-dioctyl-tin (isomers) and benzyloxy-benzylcarbonate-dioctyl-tin, and 1-alkoxy-3-alkylcarbonate-1,1,3,3-tetraalkyl-distannoxanes and 1-aralkyloxy-3-aralkylcarbonate-1,1,3,3-tetraalkyl-distannoxanes such as 1-methoxy-3-methylcarbonate-1,1,3,3-tetrabutyl-distannoxane, 1-ethoxy-3-ethylcarbonate-1,1,3,3-tetrabutyl-distannoxane, 1-propoxy-3-propylcarbonate-1,1,3,3-tetrabutyl-distannoxane (isomers), 1-butoxy-3-butylcarbonate-1,1,3,3-tetrabutyl-distannoxane (isomers), 1-pentyloxy-3-pentylcarbonate-1,1,3,3-tetrabutyl-distannoxane (isomers), 1-hexyloxy-3-hexylcarbonate-1,1,3,3-tetrabutyl-distannoxane (isomers), 1-heptyloxy-3-heptylcarbonate-1,1,3,3-tetrabutyl-distannoxane (isomers), 1-benzyloxy-3-benzylcarbonate-1,1,3,3-tetrabutyl-distannoxane, 1-methoxy-3-methylcarbonate-1,1,3,3-tetraoctyl-distannoxane, 1-ethoxy-3-ethylcarbonate-1,1,3,3-tetraoctyl-distannoxane, 1-propoxy-3-propylcarbonate-1,1,3,3-tetraoctyl-distannoxane (isomers), 1-butoxy-3-butylcarbonate-1,1,3,3-tetraoctyl-distannoxane (isomers), 1-pentyloxy-3-pentylcarbonate-1,1,3,3-tetraoctyl-distannoxane (isomers), 1-hexyloxy-3-hexylcarbonate-1,1,3,3-tetraoctyl-distannoxane (isomers), 1-heptyloxy-3-heptylcarbonate-1,1,3,3-tetraoctyl-distannoxane (isomers), and 1-benzyloxy-3-benzylcarbonate-1,1,3,3-tetraoctyl-distannoxane. One may be selected from the above group, or a mixture selected from the above group may be used.

Of carbon dioxide complex represented by formulae (8) to (13), matter in which each of the $R^1$ group, the $R^2$ group, the $R^4$ group, the $R^5$ group, the $R^7$ group, and the $R^8$ group is selected from an n-butyl group and an n-octyl group is preferable, particularly preferable examples being ones in which each of the $R^3$ group, the $R^6$ group, the $R^9$ group, and the $R^{10}$ group is an alkyl group having from 1 to 6 carbon atoms. In the case that the number of carbon atoms in the $R^3$ group, the $R^6$ group, the $R^9$ group, or the $R^{10}$ group is low, the stability and the fluidity for transfer may worsen, and in the case of having a substituent on the carbon atom adjacent to the oxygen (O) of the $OR^3$, $OR^6$, $OR^9$, or $OR^{10}$ group formed from the $R^3$, $R^6$, $R^9$, or $R^{10}$ group, the compound may not be liquid, and hence it is most preferable for this adjacent carbon atom to form a methylene ($CH_2$) structure, most preferable examples being ones in which each of the $R^3$ group, the $R^6$ group, the $R^9$ group, and the $R^{10}$ group is an alkyl group having from 4 to 6 carbon atoms and in which the carbon atom adjacent to the oxygen forms a methylene structure. Most preferable such examples include (n-butoxy)-(n-butylcarbonate)-di-n-butyl-tin, (3-methylbutoxy)-(3-methylbutylcarbonate)-di-n-butyl-tin, (n-pentyloxy)-(n-pentylcarbonate)-di-n-butyl-tin, (n-hexyloxy)-(n-hexylcarbonate)-di-n-butyl-tin, (2-ethylbutoxy)-(2-ethylbutylcarbonate)-di-n-butyl-tin, (n-heptyloxy)-(n-heptylcarbonate)-di-n-butyl-tin, (n-butoxy)-(n-butylcarbonate)-di-n-octyl-tin, (3-methoxybutoxy)-(3-methylbutylcarbonate)-di-n-octyl-tin, (n-pentyloxy)-(n-pentylcarbonate)-di-n-octyl-tin, (n-hexyloxy)-(n-hexylcarbonate)-di-n-octyl-tin, (2-ethylbutoxy)-(2-ethylbutylcarbonate)-di-n-octyl-tin, (n-heptyloxy)-(n-heptylcarbonate)-di-n-octyl-tin, 1-(n-butoxy)-3-(n-butylcarbonate)-1,1,3,3-tetra-n-butyl-distannoxane, 1-(3-methylbutoxy)-3-(3-methylbutylcarbonate)-1,1,3,3-tetra-n-butyl-distannoxane, 1-(n-pentyloxy)-3-(n-pentylcarbonate)-1,1,3,3-tetra-n-butyl-distannoxane, 1-(n-hexyloxy)-3-(n-hexylcarbonate)-1,1,3,3-tetra-n-butyl-distannoxane, 1-(2-ethylbutoxy)-3-(2-ethylbutylcarbonate)-1,1,3,3-tetra-n-butyl-distannoxane, 1-(n-butoxy)-3-(n-butylcarbonate)-1,1,3,3-tetra-n-octyl-distannoxane, 1-(3-methylbutoxy)-3-(3-methylbutylcarbonate)-1,1,3,3-tetra-n-octyl-distannoxane, 1-(n-pentyloxy)-3-(n-pentylcarbonate)-1,1,3,3-tetra-n-octyl-distannoxane, 1-(n-hexyloxy)-3-(n-hexylcarbonate)-1,1,3,3-tetra-n-octyl-distannoxane, and 1-(2-ethylbutoxy)-3-(2-ethylbutylcarbonate)-1,1,3,3-tetra-n-octyl-distannoxane. These may be in the form of a monomer or an aggregate.

Preferable examples of the carbon dioxide complex of the alkyltin alkoxide in the present invention are the carbon dioxide complex of a dialkyltin dialkoxide as described above and the carbon dioxide complex of a tetraalkyldialkoxydistannoxane as described above, although the carbon dioxide complex of an alkyltin alkoxide may also contain the carbon dioxide complex of the alkyltin alkoxide represented by any of above formulae (4) to (7).

An example of the carbon dioxide complex of the trialkyltin alkoxide represented by formula (4) is represented by following formula (14);

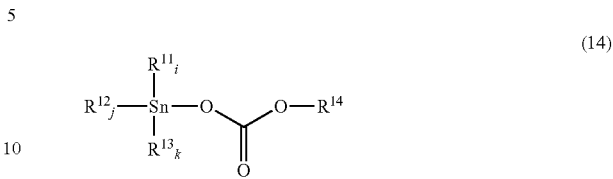

wherein $R^{11}$, $R^{12}$, $R^{13}$, and $R^{14}$ represent respectively $R^{11}$, $R^{12}$, $R^{13}$, and $R^{14}$ as defined in above formula (4), and i, j, and k represent respectively i, j, and k as defined in formula (4).

Examples of $R^{11}$, $R^{12}$, $R^{13}$, and $R^{14}$ in the bonded matter represented by above formula (14) are as described earlier, examples of the carbon dioxide complex including trialkyl-alkylcarbonate-tin compounds and trialkyl-aralkylcarbonate-tin compounds such as tributyl-methylcarbonate-tin, tributyl-ethylcarbonate-tin, tributyl-propylcarbonate-tin (isomers), tributyl-butylcarbonate-tin (isomers), tributyl-pentylcarbonate-tin (isomers), tributyl-hexylcarbonate-tin (isomers), tributyl-heptylcarbonate-tin, tributyl-benzylcarbonate-tin, trioctyl-methylcarbonate-tin, trioctyl-ethylcarbonate-tin, trioctyl-propylcarbonate-tin (isomers), trioctyl-butylcarbonate-tin (isomers), trioctyl-pentylcarbonate-tin (isomers), trioctyl-hexylcarbonate-tin (isomers), trioctyl-heptylcarbonate-tin (isomers), and trioctyl-benzylcarbonate-tin. One may be selected from the above group, or a mixture selected from the above group may be used.

Of the carbon dioxide complex of the trialkyltin alkoxide represented by formula (14), matter in which each of the $R^{11}$ group, the $R^{12}$ group, and the $R^{13}$ group is selected from an n-butyl group and an n-octyl group is preferable, particularly preferable examples being ones in which the $R^{14}$ group is an alkyl group having from 1 to 6 carbon atoms. In the case that the number of carbon atoms in the $R^{14}$ group is low, the stability and the fluidity for transfer may worsen, and in the case of having a substituent on the carbon atom adjacent to the oxygen (O) of the $OR^{14}$ group formed from the $R^{14}$ group, the compound may not be liquid, and hence it is most preferable for this adjacent carbon atom to form a methylene ($CH_2$) structure, most preferable examples being ones in which the $R^{14}$ group is an alkyl group having from 4 to 6 carbon atoms and in which the carbon atom adjacent to the oxygen forms a methylene structure. Most preferable such examples include tri-(n-butyl)-(n-butylcarbonate)-tin, tri-(n-butyl)-(n-pentylcarbonate)-tin, tri-(n-butyl)-(3-methylbutylcarbonate)-tin, tri-(n-butyl)-(n-hexylcarbonate)-tin, tri-(n-butyl)-(2-ethylbutylcarbonate)-tin, tri-(n-octyl)-(n-butylcarbonate)-tin, tri-(n-octyl)-(n-pentylcarbonate)-tin, tri-(n-octyl)-(n-hexylcarbonate)-tin, tri-(n-octyl)-(3-methylbutylcarbonate)-tin, and tri-(n-octyl)-(2-ethylbutylcarbonate)-tin.

Carbon dioxide complex of a monoalkyltin alkoxide represented by formula (5) and/or (6), or carbon dioxide complex of a trialkyl-trialkoxy-distannoxane represented by formula (7) may also be contained in the mixture of the present invention, examples of structures thereof being represented by following formulae (15), (16), and (17). Such a carbon dioxide complex of a compound represented by formula (5), (6), or (7) may take on any of various structures, there being no limitation to following formulae (15), (16), and (17);

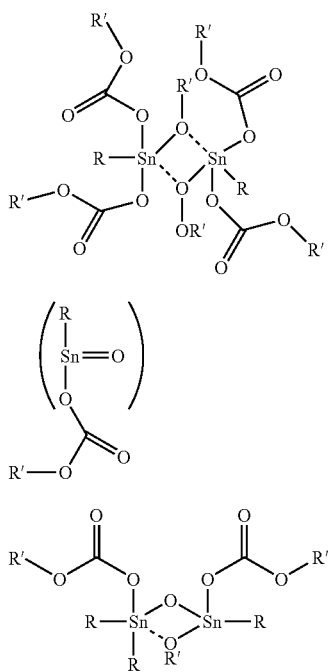

(15)

(16)

(17)

wherein R and R' in the above formulae independently represents an aliphatic group or an aralkyl group.

Examples of such a monoalkyltin alkoxide include alkyl-alkoxy-di-alkylcarbonate-tin compounds and alkyl-aralkyloxy-di-aralkylcarbonate-tin compounds such as butyl-methoxy-di-methylcarbonate-tin, butyl-ethoxy-di-ethylcarbonate-tin, butyl-propyloxy-di-propylcarbonate-tin (isomers), butyl-butoxy-di-butylcarbonate-tin (isomers), butyl-pentyloxy-di-pentylcarbonate-tin (isomers), butyl-hexyloxy-di-hexylcarbonate-tin (isomers), butyl-heptyloxy-di-heptylcarbonate-tin (isomers), butyl-benzyloxy-di-benzylcarbonate-tin, octyl-methoxy-di-methylcarbonate-tin, octyl-ethoxy-di-ethylcarbonate-tin, octyl-propoxy-di-propylcarbonate-tin (isomers), octyl-butoxy-di-butylcarbonate-tin (isomers), octyl-pentyloxy-di-pentylcarbonate-tin (isomers), octyl-hexyloxy-di-hexylcarbonate-tin (isomers), octyl-heptyloxy-di-heptylcarbonate-tin (isomers), and octyl-benzyloxy-di-benzylcarbonate-tin; alkyl-alkylcarbonate-tin oxides and alkyl-aralkylcarbonate-tin oxides such as butyl-methylcarbonate-tin oxide, butyl-ethylcarbonate-tin oxide, butyl-propylcarbonate-tin oxide (isomers), butyl-butylcarbonate-tin oxide (isomers), butyl-pentylcarbonate-tin oxide (isomers), butyl-hexylcarbonate-tin oxide (isomers), butyl-heptylcarbonate-tin oxide (isomers), butyl-benzylcarbonate-tin oxide, octyl-methylcarbonate-tin oxide, octyl-ethylcarbonate-tin oxide, octyl-propylcarbonate-tin oxide (isomers), octyl-butylcarbonate-tin oxide (isomers), octyl-pentylcarbonate-tin oxide (isomers), octyl-hexylcarbonate-tin oxide (isomers), octyl-heptylcarbonate-tin oxide (isomers), and octyl-benzylcarbonate-tin oxide; and trialkyl-di-alkylcarbonate-alkoxy-distannoxanes and trialkyl-diaralkylcarbonate-aralkyloxy-distannoxanes such as 1,1,3-tri butyl-1,3-di-methylcarbonate-3-methoxy-distannoxane, 1,1,3-tributyl-1,3-di-ethylcarbonate-3-ethoxy-distannoxane, 1,1,3-tributyl-1,3-di-propylcarbonate-3-propoxy-distannoxane (isomers), 1,1,3-tributyl-1,3-di-butylcarbonate-3-butoxy-distannoxane (isomers), 1,1,3-tributyl-1,3-di-pentylcarbonate-3-pentyloxy-distannoxane (isomers), 1,1,3-tributyl-1,3-di-hexylcarbonate-3-hexyloxy-distannoxane (isomers), 1,1,3-tributyl-1,3-di-heptylcarbonate-3-heptyloxy-distannoxane (isomers), 1,1,3-tri butyl-1,3-di-benzylcarbonate-3-benzyloxy-distannoxane, 1,1,3-trioctyl-1,3-di-methylcarbonate-3-methoxy-distannoxane, 1,1,3-trioctyl-1,3-di-ethylcarbonate-3-ethoxy-distannoxane, 1,1,3-trioctyl-1,3-di-propylcarbonate-3-propoxy-distannoxane (isomers), 1,1,3-trioctyl-1,3-di-butylcarbonate-3-butoxy-distannoxane (isomers), 1,1,3-trioctyl-1,3-di-pentylcarbonate-3-pentyloxy-distannoxane (isomers), 1,1,3-trioctyl-1,3-di-hexylcarbonate-3-hexyloxy-distannoxane (isomers), 1,1,3-trioctyl-1,3-di-heptylcarbonate-3-heptyloxy-distannoxane (isomers), and 1,1,3-trioctyl-1,3-di-benzylcarbonate-3-benzyloxy-distannoxane. One may be selected from the above group, or a mixture selected from the above group may be used.

Most preferable examples include (n-butyl)-di-(n-butylcarbonate)-(n-butoxy)-tin, (n-butyl)-di-(n-pentylcarbonate)-(n-pentyloxy)-tin, (n-butyl)-bis-(3-methylbutylcarbonate)-(3-methylbutoxy)-tin, (n-butyl)-di-(n-hexylcarbonate)-(n-hexyloxy)-tin, (n-butyl)-bis-(2-ethylbutylcarbonate)-(2-ethylbutoxy)-tin, (n-octyl)-di-(n-butylcarbonate)-(n-butoxy)-tin, (n-octyl)-di-(n-pentylcarbonate)-(n-pentyloxy)-tin, (n-octyl)-di-(n-hexylcarbonate)-(n-hexyloxy)-tin, (n-octyl)-bis-(3-methylbutylcarbonate)-(3-methylbutoxy)-tin, (n-octyl)-bis-(2-ethylbutylcarbonate)-(2-ethylbutoxy)-tin, (n-butyl)-(n-butylcarbonate)-tin oxide, (n-butyl)-(n-pentylcarbonate)-tin oxide, (n-butyl)-(3-methyl butylcarbonate)-tin oxide, (n-butyl)-(n-hexylcarbonate)-tin oxide, (n-butyl)-(2-ethylbutylcarbonate)-tin oxide, (n-octyl)-(n-butylcarbonate)-tin oxide, (n-octyl)-(n-pentylcarbonate)-tin oxide, (n-octyl)-(n-hexylcarbonate)-tin oxide, (n-octyl)-(3-methylbutylcarbonate)-tin oxide, (n-octyl)-(2-ethylbutylcarbonate)-tin oxide, 1,1,3-tri-(n-butyl)-1,3-di-(n-butylcarbonate)-3-(n-butoxy)-distannoxane, 1,1,3-tri-(n-butyl)-1,3-di-(n-pentylcarbonate)-3-(n-pentyloxy)-distannoxane, 1,1,3-tri-(n-butyl)-1,3-bis-(3-methylbutylcarbonate)-3-(3-methyl butoxy)-distannoxane, 1,1,3-tri-(n-butyl)-1,3-di-(n-hexylcarbonate)-3-(n-hexyloxy)-distannoxane, 1,1,3-tri-(n-butyl)-1,3,3-bis-(2-ethylbutylcarbonate)-3-(2-ethylbutoxy)-distannoxane, 1,1,3-tri-(n-octyl)-1,3-di-(n-butylcarbonate)-3-(n-butoxy)-distannoxane, 1,1,3-tri-(n-octyl)-1,3-di-(n-pentylcarbonate)-3-(n-pentyloxy)-distannoxane, 1,1,3-tri-(n-octyl)-1,3-bis-(3-methylbutylcarbonate)-3-(3-methylbutoxy)-distannoxane, 1,1,3-tri-(n-octyl)-1,3-di-(n-hexylcarbonate)-3-(n-hexyloxy)-distannoxane, and 1,1,3-tri-(n-octyl)-1,3-bis-(2-ethylbutylcarbonate)-3-(2-ethylbutoxy)-distannoxane.

There may be a mixture of such types of carbon dioxide complex of an alkyltin alkoxide, or one type alone, and moreover types of carbon dioxide complex of the alkyltin alkoxide may be coordinated or aggregated together. Such alkyltin alkoxides readily exchange ligands, and there may be alkyltin alkoxide carbon dioxide complex that has a structure that is difficult to identify, or that is coordinated or aggregated other than as described above. Note that the carbon dioxide complex of the alkyltin alkoxide based on the above stipulation of alkyl groups, alkoxy groups and carbonate linkages but merely cannot be identified by current analytical techniques may also be used in the present invention. Compounds as described above can be used as alkyltin alkoxides and the carbon dioxide complex of the alkyltin alkoxide contained in the mixture of the present invention; at least 20 mol %, more preferably at least 50 mol %, of the alkyltin alkoxides contained in the mixture are preferably alkyltin alkoxides represented by chemical formula (1) and/or formula (2). Moreover, in the mixture, of the carbon dioxide complex of the alkyltin alkoxide, the content of carbon dioxide complex selected from chemical formulae (8) to (13) is preferably at least 20 mol %, more preferably at least 50 mol %.

The mixture according to the present invention comprises:

a mixture for carbon dioxide transfer comprising an alkyltin alkoxide composition containing an alkyltin alkoxide and a carbon dioxide complex of an alkyltin alkoxide, and carbon dioxide;

wherein taking the number of mols of tin atoms in the alkyltin alkoxide and/or the carbon dioxide complex of the alkyltin alkoxide contained in the mixture to be Z, taking carbon dioxide incorporated in the carbon dioxide complex of the alkyltin alkoxide, and carbon dioxide contained in the mixture to be ($CO_2$), and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide, in a relationship $Z:(CO_2)_x:(OR)_y$, a molar proportion represented by x is in a range of from 0.1 to 2, and a molar proportion represented by y is in a range of from 0.5 to 2.

The existence of carbon dioxide complex of an alkyltin alkoxide has been known from hitherto, but because such matter is unstable at room temperature (see, for example, J. Am. Chem. Soc., 121 (1999), 3793-3794), transferring the carbon dioxide complex with the objective of using the carbon dioxide has not been considered. There is an example in which a reaction liquid containing dibutyltin oxide, dimethyl carbonate and carbon dioxide has been transferred using a transfer line (see, for example, Japanese Patent No. 3385359), but it was stated that the reaction liquid was transferred under the presence of a large excess of carbon dioxide (i.e. with x much greater than 2) so as to avoid hydrolysis or the like of the unstable alkyltin alkoxide (although not clearly stated, it is presumed that under the stated conditions the dibutyltin oxide is in the form of carbon dioxide complex), and that it is preferable to carry out the transfer under as high a pressure as possible. Furthermore, in the case of this example, the reaction liquid should be considered as being not so much transferred, but rather circulated through the reactor.

The present inventors carried out assiduous studies, and as a result accomplished the present invention upon discovering that for a mixture comprising carbon dioxide and an alkyltin alkoxide composition containing carbon dioxide complex of a specific alkyltin alkoxide, taking the number of mols of tin atoms in the alkyltin alkoxide and/or the carbon dioxide complex of the alkyltin alkoxide contained in the mixture to be Z, taking carbon dioxide incorporated in the carbon dioxide complex of the alkyltin alkoxide, and carbon dioxide contained in the mixture to be ($CO_2$), and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide, in the case that x and y in the relationship $Z:(CO_2)_x:(OR)_y$ are within specific ranges, then surprisingly the mixture is very stable and thus suitable for practical operation of transfer. Depending on the values of x and y, if x is less than 0.1, then the mixture exists stably, but when carbon dioxide gas is eliminated from the carbonate linkages contained in the mixture and used (the process of eliminating the carbon dioxide gas from the carbonate linkages will be described later), much energy may be required, whereas if x is greater than 2, then the mixture may become unstable and foaming may occur, and hence the mixture may be difficult to use for transfer. A preferable range for x is thus 0.1 to 2, and considering the stability for transfer, is more preferably 0.1 to 1.5, while considering also the objective of eliminating and reusing the carbon dioxide gas, is more preferably 0.5 to 1.5. The value of y depends on the value of x, but if the value of y is less than 0.5, then the amount of carbon dioxide that can be transferred using the mixture (i.e. the number of carbonate groups) inevitably decreases, and hence the amount of carbon dioxide that can be used relative to the energy for the transfer decreases, and thus the mixture is not suitable for transfer. Moreover, if the value of y is greater than 2, then the fluidity of the mixture becomes very poor, and hence transfer may not be possible. A preferable range for y is thus 0.5 to 2, and considering the fluidity for transfer, is more preferably 0.5 to 1.5.

The method of determining Z, x, and y for the mixture according to the present invention is described below. The determination of Z, x, and y is based on analysis methods that could be carried out at the time of accomplishment of the present invention, and may be carried out using another publicly known method, or using a more precise method.

For the mixture comprising carbon dioxide and an alkyltin alkoxide composition containing carbon dioxide complex of an alkyltin alkoxide, the number of mols Z of tin atoms in the alkyltin alkoxide and/or the carbon dioxide complex of the alkyltin alkoxide contained in the mixture can be determined by a method such as $^{119}$Sn-NMR. The alkyltin alkoxide analysis method is a publicly known alkyltin alkoxide analysis method (see, for example, U.S. Pat. No. 5,545,600). Note, however, that the $^{119}$Sn-NMR shift for a dialkyltin dialkoxide structure represented by formula (2) or the like varies greatly depending on the concentration of the dialkyltin dialkoxide represented by formula (2) in the sample and the presence of an alcohol or the like, and hence it is preferable to carry out the determination using the $^{119}$Sn-NMR together with $^1$H-NMR and $^{13}$C-NMR. As an example, $^{119}$Sn-NMR shift values for an alkyltin alkoxide structure represented by formula (2) synthesized using 2-ethyl-1-hexanol as a reactant and dibutyltin oxide as a starting material are shown in Table 1.

Table 1

TABLE 1

LIQUID CONCENTRATION AND $^{119}$Sn-NMR SHIFT OF ORGANOMETALLIC COMPOUND REPRESENTED BY FORMULA (16) HAVING 2-ETHYL-1-HEXYLOXY GROUP
$^{119}$Sn-NMR DATA

| wt % | δppm |
|---|---|
| 48.0 | −64.2 |
| 20.5 | −19.1 |
| 11.2 | −6.6 |
| 3.4 | 2.7 |

NOTES:
THE SHIFT (δ) IS THE VALUE BASED ON TETRAMETHYLTIN (SnMe$_4$).
THE CONCENTRATION IS THE WEIGHT CONCENTRATION (wt %) IN DEUTERATED CHLOROFORM (CDCl$_3$).

Similarly, other alkyltin alkoxides, and carbon dioxide complex of an alkyltin alkoxide can be analyzed using the method as described above. Z can be determined from the value determined by this method, and the molecular weight of the alkyltin alkoxide or the carbon dioxide complex of the alkyltin alkoxide. It should be apparent to a person skilled in the art that the value of y can also be determined at this time.

The value of x can be determined using any of various methods. This depends on the process for producing the mixture according to the present invention as described later, but, for example, in the case that the mixture according to the present invention is obtained by absorbing carbon dioxide into the dialkyltin alkoxide composition and bringing about chemical reaction, the total weight of carbon dioxide incorporated in the mixture in the form of carbonate linkages and carbon dioxide present dissolved in the mixture is determined from the difference between the weight before absorbing the gaseous carbon dioxide and the weight after the mixture has been obtained, and then x can be determined from the molecular weight of carbon dioxide. Alternatively, the determination can be carried out using another method. For example, some of the liquid mixture in the present invention (e.g. 100 mL) is removed and taken as a sample liquid (the value of Z for the sample liquid can be determined using the method for determining Z described above). The sample liquid is put into a pressure-tight sealed vessel (e.g. an autoclave) having a volume at least 10 times the volume of the sample liquid (e.g. 1 L), and the same volume as the sample liquid of water containing at least 4 molar equivalents of a Brønsted acid (e.g. acetic acid, sulfuric acid, etc.) based on Z for the sample liquid is put into the sealed vessel, so as to completely hydrolyze alkyltin alkoxides and carbon dioxide complex of an alkyltin alkoxide contained in the sample liquid. Carbon dioxide dissolved in the sample liquid and in the carbon dioxide complex of the alkyltin alkoxide contained in the sample liquid is taken into a gas phase portion as gaseous carbon dioxide. The pressure and the volume of the gas phase portion of the pressure-tight sealed vessel are measured, and the amount of carbon dioxide in the gas phase portion is measured using the publicly known method such as gas chromatography using a thermal conductivity detector or a gas analyzer, and then the number of mols x of carbon dioxide incorporated in the form of carbonate linkages contained in the sample liquid and carbon dioxide dissolved in the sample liquid can be determined from the measured pressure and volume. It should be apparent to a person skilled in the art that publicly known gas analysis methods and procedures can be used in this measurement, for example the analysis precision may be increased by passing through a dehydrating column. Alternatively, the pressure-tight sealed vessel is, for example, heated to approximately 200° C., and then the pressure in the pressure-tight sealed vessel is reduced using a vacuum pump or the like so as to remove produced gas, and an inert gas (e.g. nitrogen gas) is further blown into the pressure-tight sealed vessel so as to thoroughly remove the produced gas from the pressure-tight sealed vessel, and the gas removed using the vacuum pump or the like is captured, and then x for the sample liquid can be determined from the volume of the gas and using the publicly known carbon dioxide analysis method on the gas such as a gas analyzer as described above. Other publicly known methods may also be used in combination.

The mixture according to the present invention is a mixture for transfer. Conventionally, for transferring carbon dioxide so that the carbon dioxide can be used, there have been methods such as transferring gaseous carbon dioxide through piping from a cylinder or the like, moving a high-pressure carbon dioxide cylinder, and transporting solid carbon dioxide as a dry ice. In the case of transferring carbon dioxide having a very low water content, there have only been the method of moving a high-purity carbon dioxide cylinder, and the method of transferring through piping. Installing a high-pressure carbon dioxide cylinder can be dangerous, and may be subject to severe legal restrictions. However, according to the present invention, by transferring the mixture according to the present invention using a vessel or piping, rather than transferring or moving gaseous carbon dioxide using a cylinder that is difficult to handle due to such restrictions, carbon dioxide can be transferred or moved in the form of a liquid or as a solidified mixture that can be turned into a liquid. The mixture according to the present invention is a mixture for transfer whose objective is the effective utilization of carbon dioxide contained in the form of carbonate linkages or in a dissolved form. Because the mixture can be transferred in a liquid or liquefied form, it is very easy to carry out the transfer quantitatively using a liquid feeding pump or the like.

Following is the description of the method of transferring the mixture according to the present invention. The mixture according to the present invention is a mixture intended to be transferred as a liquid or in a liquefied form, although the mixture may be transferred in a solid state in some cases. The mixture is preferably transferred as a liquid or in a liquefied form. When transferring the liquid or liquefied mixture, to transfer the mixture stably, the transfer is preferably carried out at a temperature in a range of from −40 to 80° C. Moreover, considering the fluidity during the transfer, a range of from 0 to 80° C. is more preferable, the most preferable range being from room temperature (approximately 20° C.) to 80° C. Other components may be added to the mixture so long as the transfer of the mixture and the recovery and utilization of carbon dioxide are not affected. Examples of such non-affecting components include primary alkyl alcohols, other tin components (e.g. a tetraalkyltin, a tetraalkoxytin, or a monoalkyltin hydroxide, and so long as the transfer is not affected a dialkyltin oxide or tin oxide may also be contained), solvents (ether solvents, aromatic solvents, aliphatic solvents etc. that do not affect the transfer), and inert gases (e.g. nitrogen gas, argon gas, helium gas, methane gas, carbon dioxide gas etc.). Specific examples of solvents include methanol, ethanol, propanol (isomers), butanol (isomers) pentanol (isomers), hexanol (isomers), heptanol (isomers), tetrahydrofuran, dioxane, benzene, toluene, and xylene (isomers); in the case of using an alcohol, it is preferable in terms of the stability of the mixture to use an alcohol containing an alkyl group the same as the alkyl group in the alkoxy groups of an alkyltin alkoxide contained in the alkyltin alkoxide composition. The pressure during the transfer is preferably in a range of from normal pressure to 1 MPa, and so that the mixture according to the present invention obtained exists stably, a range of from normal pressure to 0.6 MPa is more preferable.

The mixture according to the present invention is a stable mixture, but is subject to hydrolysis as with an ordinary metal alkoxide, and hence during the transfer, it is preferable to pay heed to water to an extent that would be apparent to a person skilled in the art. In the case that the mixture contains a carbonate, the carbonate content is preferably not more than 20 mol % based on the number of mols of tetraalkyldialkoxydistannoxane in the alkyltin alkoxide composition in the mixture, and in the case that the composition contains a dialkyltin oxide, the carbonate content is preferably also not more than 20 mol % based on the dialkyltin oxide. This is because in the case that a carbonate is present, excess carbon dioxide may be produced, and hence the mixture may become unstable. Furthermore, in the case of transferring the mixture and using the mixture to produce a carbonate, from equilibrium constraints, it is undesirable for the mixture to contain a carbonate, since then the amount of carbonate newly produced may decrease.

When transferring the mixture according to the present invention, a vessel or piping made of the publicly known structural material can be used. Instrumentation such as a flow meter and a thermometer and the publicly known process equipment such as a reboiler, a pump, and a condenser may be added as required, and to keep the temperature constant, the publicly known method such as steam or a heater may be used for heating, while the publicly known method such as natural cooling, cooling water or brine may be used for cooling. The publicly known material can be used with there being no particular limitations thereon. Examples thereof include plastic, paper, stainless steel and the like.

Examples of processes for obtaining the mixture according to the present invention are described below, although there is no limitation to these. A preferable process is one in which an alkyltin alkoxide composition containing at least one alkyltin alkoxide as described above is obtained. A particularly preferable composition is an alkyltin alkoxide composition containing tetraalkyldialkoxydistannoxane represented by formula (1) and/or dialkyltin dialkoxide represented by formula (2). The proportion of tin atoms contained in the alkyltin alkoxides represented by formulae (1) and (2) based on the total number of mols of tin atoms contained in the alkyltin alkoxides in the composition is preferably not less than 30%, more preferably not less than 40%, yet more preferably not less than 50%.

The present inventors carried out assiduous studies, and as a result discovered that carbon dioxide complex of tetraalkyldialkoxydistannoxane has a high bonding strength to the carbon dioxide, and ascertained that in the case of the objective being recovery and utilization of carbon dioxide, it is preferable for the composition to have a high dialkyltin dialkoxide content. The most preferable composition is thus one in which the molar ratio between the tetraalkyldialkoxydistannoxane and the dialkyltin dialkoxide contained in the alkyltin alkoxide composition is in a range of from 0:100 to 80:20. In the case of improving the productivity, or fixing more carbon dioxide through the carbon dioxide complex, a more preferable range is from 10:90 to 70:30.

Following are examples of processes for obtaining the mixture according to the present invention.
1) Process of absorbing gaseous carbon dioxide into alkyltin alkoxide composition The mixture according to the present invention can be obtained by absorbing gaseous carbon dioxide into an alkyltin alkoxide composition as described above and bringing about chemical reaction.

As similar processes, there are known processes in which a carbonate is obtained from carbon dioxide and an alkyltin alkoxide. Examples are processes previously disclosed by the present inventors (e.g. WO 2003/055840, WO 2004/014840 etc.). Such a reaction in which a carbonate is produced from carbon dioxide and an alkyltin alkoxide uses a reaction represented by formula (18), and is an endothermic reaction that is carried out while supplying in heat from the outside, but the present invention greatly differs in that exothermic reactions as represented, for example, by formulae (19) to (21) are used:

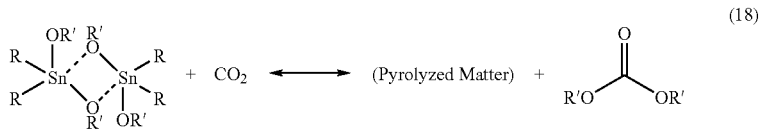

(18)

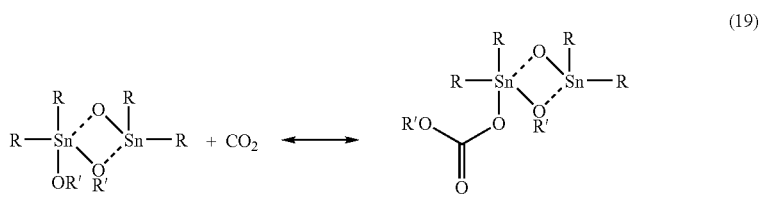

(19)

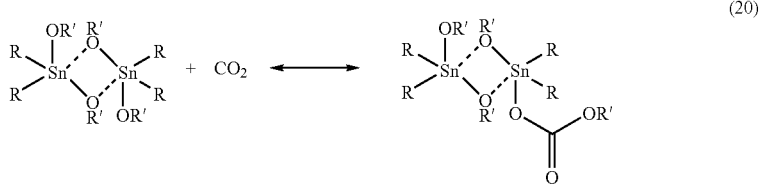

(20)

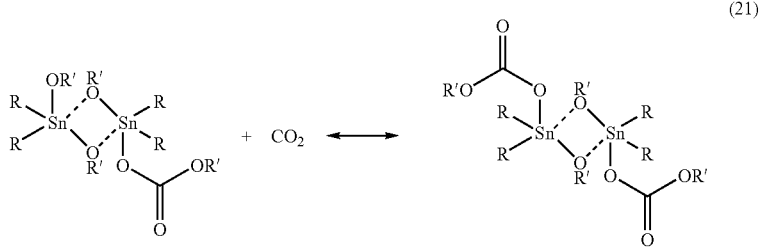

(21)

R and R' in the above formulae independently represent an aliphatic group or an aralkyl group.

The gaseous carbon dioxide may be any carbon dioxide gas, but in the case of using the mixture according to the present invention with the objective of transferring the mixture and extracting carbon dioxide gas having a lower water content than the carbon dioxide gas used in the process, for example carbon dioxide gas having a water content of up to 10000 ppm can be used. This is conjectured to be because water is consumed through the mixture according to the present invention undergoing partial hydrolysis, so that when the gaseous carbon dioxide is extracted from the mixture, the water that has been consumed in the hydrolysis is not contained; even so, it has been found that there is a previously unreported surprising unpredicted effect that carbon dioxide gas from which even a trace amount of water has been removed can be extracted. In the case of transferring the mixture according to the present invention and using the mixture in carbonate production or the like, a decrease in carbonate yield may arise due to the above hydrolysis reaction, and hence it is preferable to use carbon dioxide gas having the water content of not more than 1000 ppm, more preferably not more than 500 ppm. The most preferable example of the carbon dioxide is carbon dioxide-containing gas discharged from a step of producing carbonate by reacting carbon dioxide with an alkyltin alkoxide as a starting material, this being excess carbon dioxide gas not consumed as the carbonate.

The reaction pressure depends on the reaction temperature, but is preferably in a range of from normal pressure to 1 MPa, and so that the mixture according to the present invention obtained exists stably, a range of from normal pressure to 0.6 MPa is more preferable. The reaction temperature depends on the reaction pressure, but in the case of high temperature and high pressure a carbonate is readily produced so that the mixture of the present invention tends to no longer exist stably, and hence to obtain the mixture of the present invention, a range of from −40 to 80° C. is preferable; furthermore, the objective of the mixture according to the present invention is to transfer and use carbon dioxide, and hence considering the fluidity during the transfer, a range of from 0 to 80° C. is more preferable, the most preferable range being from room temperature (approximately 20° C.) to 80° C. The reaction is preferably carried out with a reaction time of from a few seconds to 100 hours, and considering productivity and so on, a range of from a few minutes to 10 hours is preferable. Furthermore, when carrying out the reaction, the alkyltin alkoxide composition is preferably liquid, a liquid or liquefied alkyltin alkoxide composition being used. In the case of a solid, the composition may be heated, or a solvent may be added. Examples of solvents are as above.

Furthermore, by using the above production process, the mixture, and carbon dioxide having a lower water content than the supplied carbon dioxide can be simultaneously obtained. Gaseous carbon dioxide is continuously supplied into the reactor and chemical reaction is carried out, and the mixture thus obtained is obtained as a liquid phase component, while a gas phase portion in the reactor is simultaneously continuously withdrawn, whereby dry gaseous carbon dioxide having a lower water content than the continuously supplied gaseous carbon dioxide can be obtained.

2) Process of reacting carbonate represented by following formula (22) with alkyltin alkoxide composition containing dialkyltin oxide represented by following formula (23) and/or tetraalkyldialkoxydistannoxane represented by chemical formula (1):

(22)

wherein $R^{27}$ and $R^{28}$ independently represent an aliphatic group or an aralkyl group.

Each of $R^{27}$ and $R^{28}$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. $R^{27}$ and $R^{28}$ in formula (22) may be the same as one another, or in some cases may be different.

Examples of such a carbonate include dialkyl carbonates such as dimethyl carbonate, diethyl carbonate, dipropyl carbonate (isomers), dibutyl carbonate (isomers), diphenyl carbonate (isomers), dihexyl carbonate (isomers), diheptyl carbonate, and dibenzyl carbonate. One may be selected from the above group, or a mixture selected from the above group may be used.

Of the carbonates represented by formula (22), in the case that the number of carbon atoms in the $R^{27}$ group or the $R^{28}$ group is low, the stability of the mixture obtained and the fluidity for transfer may worsen, and furthermore in the case of having a substituent on the carbon atom adjacent to the oxygen (O) of the $OR^{27}$ or $OR^{28}$ group formed from the $R^{27}$ or $R^{28}$ group, the mixture obtained may not be liquid, and hence it is most preferable for this adjacent carbon atom to form a methylene ($CH_2$) structure, most preferable examples being ones in which each of the groups $R^{27}$ and $R^{28}$ is an alkyl group having from 4 to 6 carbon atoms and in which the carbon atom adjacent to the oxygen forms a methylene structure. Most preferable such examples include di-(n-butyl)-carbonate, di-(n-pentyl)-carbonate, bis-(3-methylbutyl)-carbonate, di-(n-hexyl)-carbonate, and bis-(2-ethylbutyl)-carbonate.

(23)

wherein $R^{29}$ and $R^{30}$ independently represent an aliphatic group or an aralkyl group.

Examples of each of $R^{29}$ and $R^{30}$ in the dialkyltin oxide of formula (23) include alkyl groups being aliphatic hydrocarbon groups having from 1 to 12 carbon atoms and cycloalkyl groups being alicyclic hydrocarbon groups having from 5 to 12 carbon atoms such as methyl, ethyl, propyl, butyl (isomers), pentyl (isomers), hexyl (isomers), heptyl (isomers), octyl (isomers), nonyl (isomers), decyl (isomers), undecyl (isomers), dodecyl (isomers), 2-butenyl, cyclobutenyl, cyclobutyl, cyclopentyl, cyclohexyl, cyclopentyl, cyclopentadienyl and cyclohexenyl, and aralkyl groups having from 7 to 20 carbon atoms such as benzyl and phenylethyl. Moreover, the alkyl group may contain an ether linkage, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable. A straight chain or branched alkyl group having from 1 to 8 carbon atoms is particularly preferable. A group having more carbon atoms than above may be used, but the fluidity may worsen, or the productivity may be impaired. $R^{29}$ and $R^{30}$ in formula (23) may be the same as one another, or in some cases may be different.

Examples of such a dialkyltin oxide include dialkyltin oxides such as dibutyltin oxide and dioctyltin oxide. One may be selected from the above group, or a mixture selected from the above group may be used.

Of the dialkyltin oxides represented by formula (23), one in which each of the groups $R^{29}$ and $R^{30}$ is selected from an n-butyl group and an n-octyl group is preferable. The dialkyltin oxide is shown as a monomer structure in formula (23), but as it is publicly known to persons skilled in the art, such a dialkyltin oxide generally exists as a polymer with the tin-oxygen double bond not being formed, and hence there is no limitation to the structure of formula (23).

It is publicly known that dialkyltin dialkoxide can be obtained from a tetraalkyldialkoxydistannoxane and a carbonate (see, for example, U.S. Pat. No. 5,545,600). It is presumed that the dialkyltin dialkoxide is produced through following formula (24):

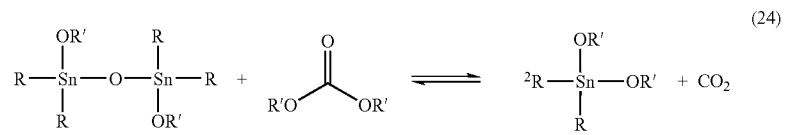

R and R' in the above formula independently represent an aliphatic group or an aralkyl group.

Similarly, tetraalkyldialkoxydistannoxane or dialkyltin dialkoxide can be produced from a dialkyltin oxide and a carbonate in accordance with reactions presumed to be as in following formulae (25) and (26):

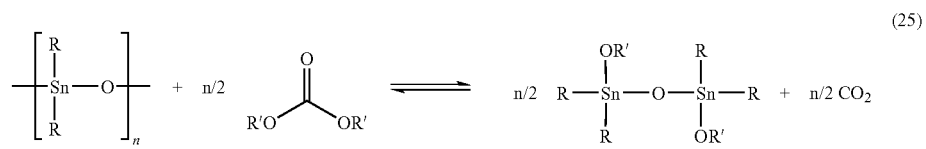

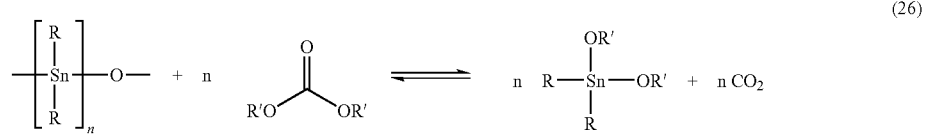

R and R' in the above formulae independently represent an aliphatic group or an aralkyl group.

The present inventors carried out assiduous studies, and as a result discovered that by controlling the above reactions, reactions represented by following formulae (27) to (29) can be made to take place in combination so as to obtain the mixture of the present invention:

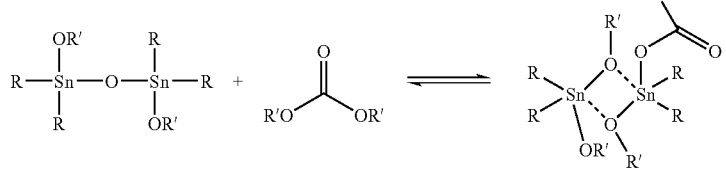

(27)

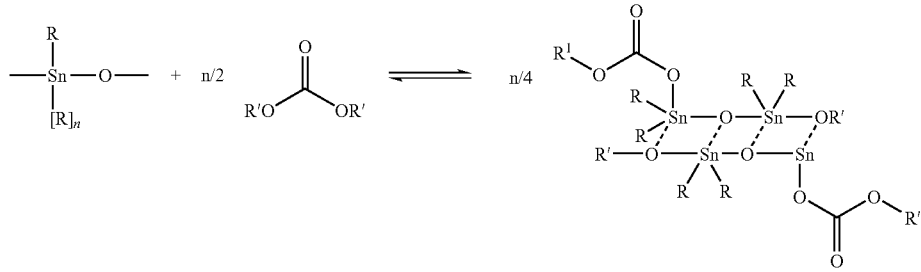

(28)

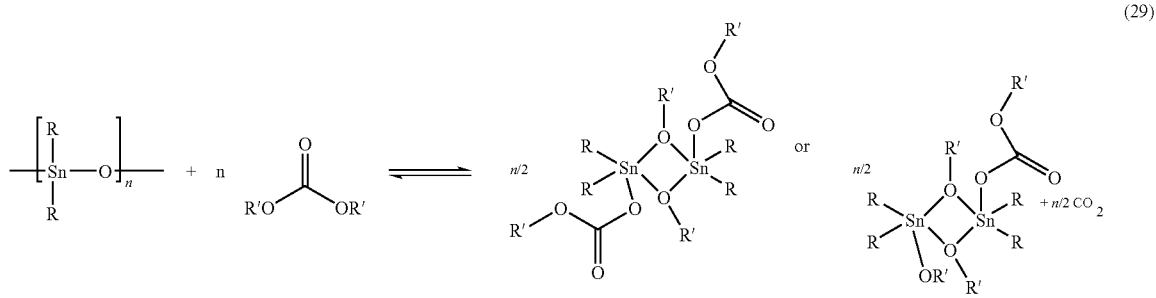

(29)

R and R' in the above formulae independently represent an aliphatic group or an aralkyl group.

In the case of using tetraalkyldialkoxydistannoxane, the carbonate is used in an amount of, for example, 0.1 to 1 molar equivalents based on the tetraalkyldialkoxydistannoxane, and in the case of using a dialkyltin oxide, the carbonate is used in an amount of, for example, 0.1 to 1 molar equivalents. The reaction temperature here is in a range of from 50 to 200° C., although in the case that the temperature is high, the above carbon dioxide-releasing reactions of formulae (24) to (26) are prone to take place, and hence a range of from 50 to 150° C. is preferable. The reaction is generally carried out at a pressure in a range of from normal pressure to 1 MPa, since the reactions represented by formulae (24) to (26) are prone to take place under reduced pressure. Whether carbon dioxide complex is obtained or whether the carbon dioxide-releasing reactions proceed so that gaseous carbon dioxide is released from the carbon dioxide complex is governed by equilibrium reactions. Moreover, the reaction of producing carbonate from the carbon dioxide complex is also governed by an equilibrium reaction, and hence although dependent on the reaction temperature, a more preferable range for the reaction pressure is from 0.1 MPa to 0.8 MPa. In some cases, the reaction may be carried out with the carbon dioxide being pressurized. The reaction is carried out with a reaction time in a range of from a few minutes to 100 hours, and considering productivity and so on, a range of from a few minutes to 10 hours is preferable. As a solvent, a solvent having no adverse effects as for the transfer described earlier can be used, examples including ether solvents, aromatic solvents, and aliphatic solvents. Specific examples of solvents include methanol, ethanol, propanol (isomers), butanol (isomers) pentanol (isomers), hexanol (isomers), heptanol (isomers), tetrahydrofuran, dioxane, benzene, toluene, and xylene (isomers). Moreover, an inert gas (e.g. nitrogen gas, argon gas etc.) may be present together with the solvent. As described above, there is a preferable range for the amount of carbonate contained in the mixture according to the present invention, and hence when producing the mixture according to the present invention through the above process, the amount of the carbonate used and the reaction conditions are selected such that the amount of residual carbonate is within this preferable range. In some cases, carbonate may be removed. In the above process of obtaining the mixture using carbonate, it is not the case that carbon dioxide is fixed directly, but rather carbonate linkages are obtained as in the case of using carbon dioxide gas, and hence the mixture obtained through this process is the mixture according to the present invention.

When producing the mixture through the production process described in 1) or 2) above or through another process, a publicly known reactor can be used. This may be a tank reactor, a column reactor, or a tube reactor. For example, a batch reactor, a semi-batch reactor, a continuous stirred tank reactor, or a flow reactor, or a combined reactor in which such reactors are connected together may be used. There are no particular limitations on the material of the reactor, it being possible to use the publicly known material. This may be selected in accordance with the reaction conditions from within the scope of common knowledge of persons skilled in the art. For example, a material such as stainless steel (SUS) or iron can be used, examples being martensitic stainless steel (SUS 410 etc.), ferritic stainless steel (SUS 430 etc.), and austenitic stainless steel (SUS 304, SUS 316 etc.). Of metallic materials, stainless steel is preferable. Instrumentation such as a flow meter and a thermometer and the publicly known process equipment such as a reboiler, a pump, and a condenser may be added as required, and a publicly known method such as steam or a heater may be used for heating, while the publicly known method such as natural cooling, cooling water or brine may be used for cooling.

Next, usage of the mixture according to the present invention will be described. Use as a mixture for transfer has already been described.

a) Using Carbon Dioxide Extracted from the Mixture According to the Present Invention It has already been explained that carbon dioxide having the low water content can be extracted from the mixture according to the present invention. There are no particular limitations on the usage of the carbon dioxide, it being possible use the carbon dioxide within the scope of the publicly known carbon dioxide usage examples. For example, the carbon dioxide can be used for beverages, for cleaning using carbon dioxide, for cultivation or storage of vegetables or the like, or for ripening fruit such as bananas. The carbon dioxide can also be used in storage and stabilization of chemical products. For example, a primary amine compound can be solidified and stored as carbamate by being reacted with the carbon dioxide. Because the water content of the carbon dioxide of the present invention is very low, there is no production of water of crystallization or the like, and hence high-quality storage is possible.

A method for extracting carbon dioxide gas from the mixture according to the present invention will now be described, although the method other than that described below may be used. For example, the mixture according to the present invention is heated, or subjected to reduced pressure, whereby carbon dioxide fixed as carbonate linkages in the carbon dioxide complex of the alkyltin alkoxide, and dissolved carbon dioxide can be extracted as gaseous carbon dioxide. The mixture according to the present invention can be used as a starting material in carbonate synthesis as is, or can be stored with the carbon dioxide being discharged as gaseous carbon dioxide when required. As the storage conditions, the storage is carried out at the temperature at which the reaction for recovery described earlier was carried out, or a temperature lower than this. This is because the liquid composition contains carbon dioxide complex of the alkyltin alkoxide and dissolved carbon dioxide, and the carbon dioxide adsorption/desorption equilibrium varies with temperature, the equilibrium moving toward the side of desorption at high temperature, and hence the temperature during storage is preferably lower than the temperature at which the recovery (insertion/adsorption/addition) was carried out. Discharging carbon dioxide gas from the liquid composition can thus easily be carried out by heating. As described above, the temperature for this is higher than the temperature at which the recovery (insertion/adsorption/addition) was carried out.

Moreover, carbon dioxide gas can also be extracted by subjecting to reduced pressure. The recovery (insertion/adsorption/addition) reaction is an equilibrium reaction, and hence depends on the carbon dioxide concentration (partial pressure) in the gas phase portion. Consequently, to discharge the carbon dioxide at the reaction temperature used in the recovery (insertion/adsorption/addition), the pressure should be reduced to below the pressure used in the recovery reaction. Preferably, the carbon dioxide gas can be extracted efficiently by heating and reducing the pressure. The heating temperature depends on the values of Z, x, and y for the mixture, and the pressure, but the carbon dioxide gas can be extracted at a temperature in a range of from room temperature to 200° C. In the case that the temperature is low, it may be necessary to reduce the pressure, or add an additive as described below. A preferable temperature range is from 60 to 200° C., but at high temperature the thermolysis of alkyltin alkoxides in the mixture may occur, and hence a range of from 60 to 150° C. is more preferable. The most preferable range is from 80 to 150° C. The pressure during the extraction depends on the values of Z, x, and y for the mixture, and the temperature, but the extraction can be carried out in the range of depressurized condition to pressurized condition. An example is a range from 10 Pa to 1 MPa, but the pressure is preferably low so as to carry out the extraction efficiently, and hence a preferable range is from 10 Pa to 0.1 MPa, more preferably from 10 Pa to normal pressure. The extraction can also be carried out by adding an additive to the mixture. Preferable additives include Brønsted acids having a higher acidity than carbonic acid, diol compounds, and amine compounds. As examples thereof, there can be used an organic acid or inorganic acid such as acetic acid, sulfuric acid, hydrochloric acid, phenol or catechol, a 1,2-glycol or 1,3-glycol or the like such as ethylene glycol or propylene glycol, or an amine such as butylamine or ethylenediamine. The additive can be used at a temperature and pressure in a range as above. The amount added may be in a range of from 0.1 to 100 molar equivalents based on Z. Note, however, that in the case of regenerating and using the mixture after the carbon dioxide has been extracted from the mixture, the extraction is preferably carried out using the method in which an additive is not added. The time for which the extraction is carried out can be freely selected as required, but in the case of using a temperature, pressure, and additive as above, is preferably controlled within a range of from a few seconds to 100 hours in accordance with the amount used.

There are no limitations on a vessel or piping used in the extraction, it being possible to use the publicly known reactor or piping. The reactor may be a tank reactor, a column reactor, or a tube reactor. For example, a batch reactor, a semi-batch reactor, a continuous stirred tank reactor, or a flow reactor, or a combined reactor in which such reactors are connected together may be used. There are no particular limitations on the material of the reactor, it being possible to use the publicly known material. This may be selected in accordance with the extraction conditions from within the scope of common knowledge of persons skilled in the art. For example, a material such as stainless steel (SUS) or iron can be used, examples being martensitic stainless steel (SUS 410 etc.), ferritic stainless steel (SUS 430 etc.), and austenitic stainless steel (SUS 304, SUS 316 etc.). Of metallic materials, stainless steel is preferable. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling.

The mixture according to the present invention can be produced under mild conditions, and hence can easily be produced using low-pressure carbon dioxide discharged from another chemical production process. The production of the mixture according to the present invention is thus a carbon dioxide recovery utilization process. By recovering low-pressure carbon dioxide that conventionally would have been not used but rather discharged into the atmosphere, so as to produce the mixture according to the present invention, and transferring the carbon dioxide (carbon dioxide complex of an alkyltin alkoxide, and dissolved carbon dioxide) contained in the mixture as a liquid or liquefied mixture, the carbon dioxide can be used effectively.

The carbon dioxide that is the object of recovery in the present invention is mainly carbon dioxide-containing gas discharged from a carbonate production process using carbon dioxide as a starting material. More specifically, for a process of producing carbonate by reacting carbon dioxide and an alkyltin alkoxide composition together, it is an object to recover and reuse carbon dioxide gas that is contained in a reaction liquid withdrawn from the carbonate-producing reactor and has not been consumed as carbonate. This unconsumed carbon dioxide is withdrawn from the reaction liquid out of the system as carbon dioxide gas in a carbon dioxide-releasing step, and is generally discharged into the atmosphere, but by using the alkyltin alkoxide composition so as to recover the withdrawn carbon dioxide gas as a mixture containing carbon dioxide complex of alkyltin alkoxide, and introducing the liquid or liquefied mixture into the carbonate-producing reactor, the amount of carbon dioxide gas discharged into the atmosphere can be reduced, and hence the carbon dioxide utilization efficiency can be improved. As the process of producing the carbonate using the mixture, a process previously invented by the present inventors can be preferably used (e.g. WO 2003/055840, WO 2004/014840). The present invention is a development of that invention accomplished by further assiduous studies, the reaction between alkyltin alkoxide and carbon dioxide in that invention simply being replaced by a reaction between the mixture according to the present invention and carbon dioxide, whereby the amount of carbon dioxide used in the carbonate production can be greatly reduced. This is because carbon dioxide that has conventionally been discharged to the atmosphere can be reused in the production of the mixture according to the present invention.

The carbonate production process previously invented by the present inventors is a process in which, as shown in following formula (30), an organometallic compound is reacted with carbon dioxide so as to form a carbon dioxide adduct of the organometallic compound, and then carbonate is produced by thermal decomposition. In the present invention, a specific alkyltin alkoxide is used as the organometallic compound, whereby by reacting the alkyltin alkoxide with gaseous carbon dioxide in advance, a specific mixture containing the carbon dioxide complex of the alkyltin alkoxide is produced, and then after transferring the mixture, carbonate can be produced through a pyrolysis reaction. As the gaseous carbon dioxide, carbon dioxide gas recovered from the reaction liquid after the pyrolysis can be very suitably used.

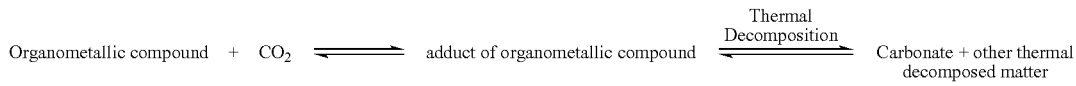

FIG. 1 illustrates an example of the flow of carbonate production using the mixture of the present invention. The process is described below based on FIG. 1.

Step 1: Carbon Dioxide Complex Production Step

This is a step of producing the mixture according to the present invention, being a step of obtaining a mixture for carbon dioxide transfer comprising carbon dioxide and an alkyltin alkoxide composition containing alkyltin alkoxide and the carbon dioxide complex of the alkyltin alkoxide, wherein taking the number of mols of tin atoms in the alkyltin alkoxide and/or the carbon dioxide complex of the alkyltin alkoxide contained in the mixture to be Z, taking carbon dioxide incorporated in the carbon dioxide complex of the alkyltin alkoxide, and carbon dioxide contained in the mixture to be ($CO_2$), and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide, in a relationship $Z:(CO_2)_x:(OR)_y$, a molar proportion represented by x is in a range of from 0.1 to 2, and a molar proportion represented by y is in a range of from 0.5 to 2.

Step 2: Transfer Step

This is a step of transferring the liquid or liquefied mixture into a carbonate synthesis step.

Step 3: Carbonate-Producing Step

This is a step of obtaining a reaction liquid containing carbonate from the mixture under the presence of carbon dioxide.

Step 4: Carbon Dioxide-Releasing Step

This is a step of separating out carbon dioxide as a gaseous component from the reaction liquid. Here, the carbonate-containing reaction liquid obtained through the separation is preferably processed by providing a carbonate separation step and so on.

As described above, a process in which carbon dioxide-containing gas discharged from the carbonate production step in which carbon dioxide was used as a starting material is used to produce the mixture according to the present invention is preferable, it being preferable to obtain the mixture using the gaseous carbon dioxide separated out from step 4 shown in FIG. 1 and above.

Figure 2:
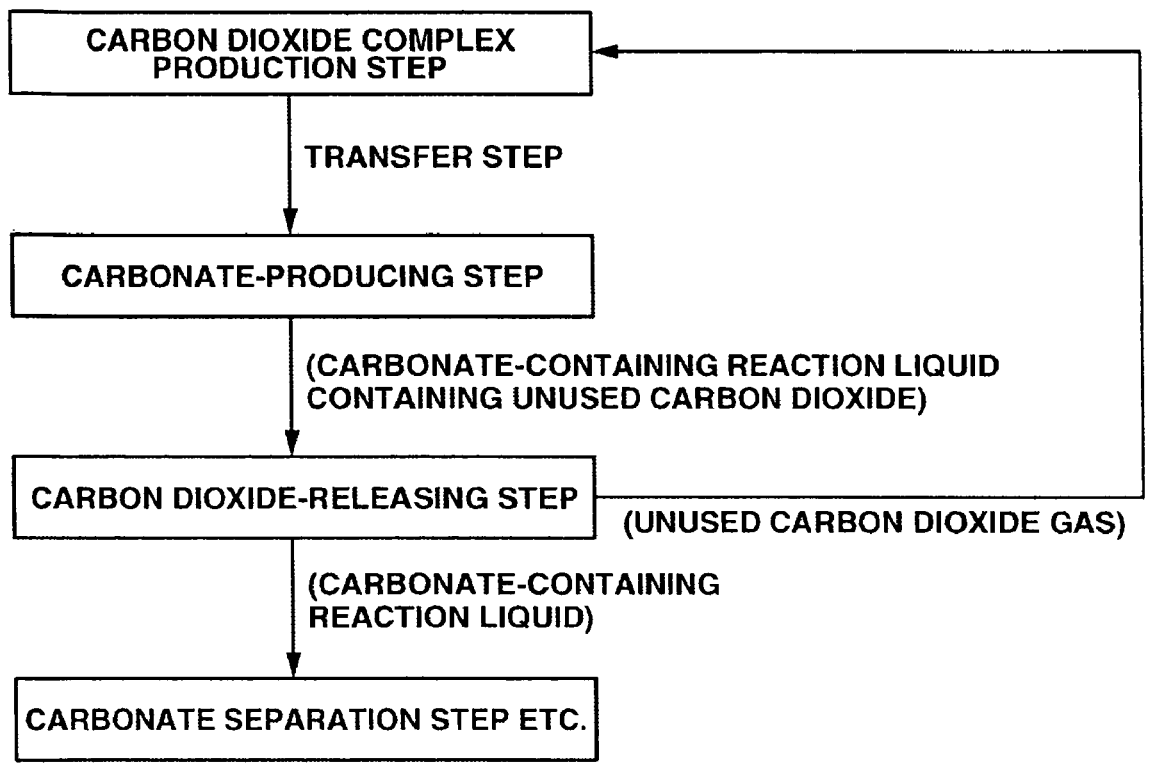
FIG. 2 illustrates a flow diagram in which unused carbon dioxide gas is recovered so as to obtain the mixture of the present invention, and a carbonate is produced.

FIG. 2 illustrates a flow diagram in which the mixture according to the present invention is obtained using the gaseous carbon dioxide separated out from step 4, and carbonate is produced. The process is described below based on FIG. 2.

This is a process in which carbonate is produced by adding following step 5 to the process shown in FIG. 1.

Step 5: Unused Carbon Dioxide Gas Recycling Step

This is a step of recycling the gaseous carbon dioxide separated out in step 4 into step 1.

Figure 3:
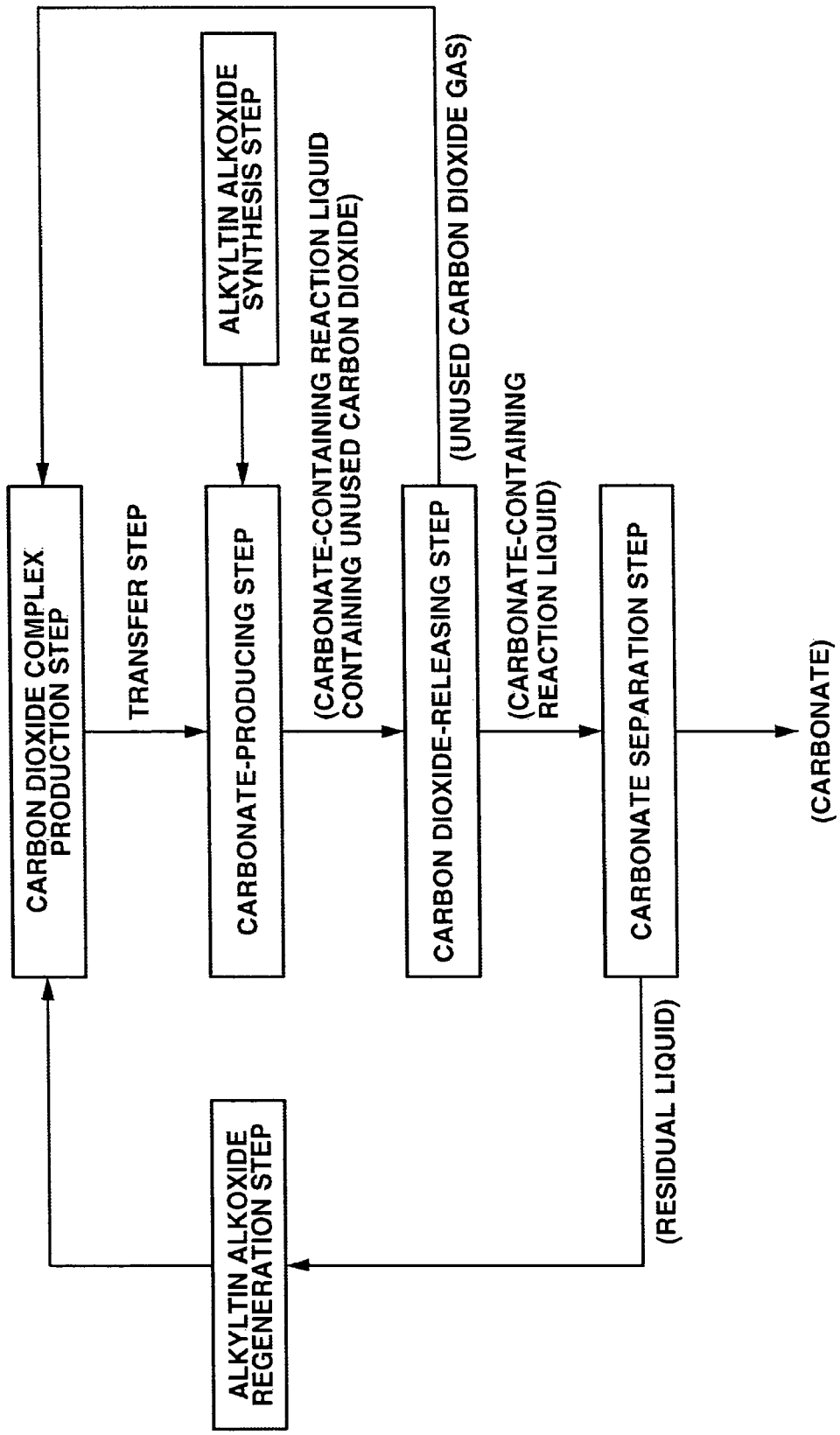
FIG. 3 illustrates a flow diagram in which unused carbon dioxide gas is recovered so as to obtain the mixture of the present invention, and a carbonate is produced.

Furthermore, FIG. 3 illustrates a flow diagram of a continuous carbonate production process in which an alkyltin alkoxide regeneration step is further added. The process is described below based on FIG. 3.

This is a process in which a carbonate is continuously produced by adding following steps 6 to 8 after step 5 shown in FIG. 2.

Step 6: Carbonate Separation Step

This is a step of separating out the carbonate from the reaction liquid from which the carbon dioxide has been separated out in step 4, so as to obtain a residual liquid.

Step 7: Alkyltin Alkoxide Regeneration Step

This is a step of reacting the residual liquid with an alcohol, so as to obtain an alkyltin alkoxide composition.

Step 8: Alkyltin Alkoxide Recycling Step

This is a step of recycling the alkyltin alkoxide composition into step 1.

At the start of the continuous reaction, there is no residual liquid to be used in step 5 or unused carbon dioxide gas to be used in step 1, and hence an alkyltin alkoxide synthesis step is separately provided, alkyltin alkoxide produced in this synthesis step being transferred into step 1 and/or step 3 for startup. In the case of transferring into step 1, fresh carbon dioxide is supplied in. Regarding the specification of this carbon dioxide, carbon dioxide gas as described earlier in process 1) for producing the mixture according to the present invention can be preferably used. In the alkyltin alkoxide synthesis step or alkyltin alkoxide regeneration step, at least alkyltin alkoxide enabling the mixture according to the present invention to be obtained in step 1 is produced and transferred into step 1.

Following is a detailed description of each of the steps.

i) Alkyltin Alkoxide Synthesis Step (Step Used Upon Startup of Continuous Operation)

For this step, an alkyltin alkoxide production process previously disclosed by the present inventors (e.g. WO 2005/111049) can be preferably used. This step is a step of producing alkyltin alkoxide from dialkyltin oxide and alcohol, the alcohol used being one represented by following formula (31):

$$R^{31}OH \tag{31}$$

wherein $R^{31}$ represents an aliphatic group or an aralkyl group.

$R^{31}$ represents a straight chain or branched aliphatic group having from 1 to 12 carbon atoms, a cycloalkyl group having from 5 to 12 carbon atoms, a straight chain or branched alkenyl group having from 2 to 12 carbon atoms, or an aralkyl group having from 7 to 20 carbon atoms comprising an optionally substituted aryl having from 6 to 19 carbon atoms and an alkyl selected from the group consisting of straight chain or branched alkyls having from 1 to 14 carbon atoms and cycloalkyls having from 5 to 14 carbon atoms, or may be a halogenated hydrocarbon group in which all or some of the hydrogens in a hydrocarbon group are substituted with halogen atoms such as nonafluorobutyl or heptafluorobutyl (isomers), although there is no limitation to the above. An alkyl group is preferable, an alcohol having an alkyl group having from 4 to 6 carbon atoms and having a boiling point higher than water at normal pressure being preferable.

Examples of such an alcohol include n-butanol, 2-methyl-1-propanol, pentanol (isomers), and hexanol (isomers). Of the alcohols represented by formula (31), in the case that each of the alkoxy groups of the alkyltin alkoxide obtained is an $OR^{31}$ group formed from the $R^{31}$ group having a substituent on the carbon atom adjacent to the oxygen (O), the mixture according to the present invention obtained from the alkyltin alkoxide may not be liquid, and hence it is most preferable for this adjacent carbon atom to form a methylene ($CH_2$) structure, most preferable examples being alcohols in which $R^{31}$ is an alkyl group having from 4 to 6 carbon atoms and in which the carbon atom adjacent to the oxygen forms a methylene structure, these being primary alcohols having a boiling point higher than water at normal pressure. Most preferable such examples include n-butanol, 2-methyl-1-propanol, n-pentanol, 3-methyl-1-butanol, n-hexanol, and 2-ethyl-1-butanol.

The dialkyltin oxide used in the alkyltin alkoxide synthesis step used in the carbonate production process of the present invention is a dialkyltin oxide represented by formula (23) described earlier. The alcohol and the dialkyltin oxide are subjected to a dehydration reaction, a tetraalkyldialkoxydistannoxane and/or a dialkyltin dialkoxide being obtained while removing produced water from the system. The amount of the alcohol used is in a range of from 2 to 100 molar equivalents based on the dialkyltin oxide, the amount of the alcohol preferably being high so as to increase the proportion of the dialkyltin dialkoxide in the alkyltin alkoxide composition produced and/or increase the production rate. However, considering the size of the reactor and so on, the amount of the alcohol is preferably low. A preferable range is thus from 4 to 80 molar equivalents, more preferably from 4 to 50 molar equivalents. The reaction temperature is, for example, in a range of from 80 to 180° C., and to remove the produced water out of the system by distillation, although dependent on the reaction pressure, is preferably in a range of 100 to 180° C., and considering that the produced alkyltin alkoxides may be altered at high temperature, is more preferably in a range of 100 to 160° C. The reaction pressure is a pressure at which the produced water can be removed out of the system, and although dependent on the reaction temperature, is in a range of from 20 to $1\times10^6$ Pa. There are no particular limitations on the reaction time for the dehydration reaction (the residence time in the case of a continuous process), but this is generally from 0.001 to 50 hours, preferably from 0.01 to 10 hours, more preferably from 0.1 to 2 hours. The reaction may be terminated once the desired alkyltin alkoxide composition has been obtained. The progress of the reaction can be determined by measuring the amount of water withdrawn out of the system, and can also be determined by sampling the reaction liquid and carrying out $^{119}$Sn-NMR. So that the mixture according to the present invention can be produced in step 1, the reaction is terminated once it has been confirmed that the alkyltin alkoxide composition has been obtained for which a molar ratio between the tetraalkyldialkoxydistannoxane and the dialkyltin dialkoxide contained in the composition is in a range of from 0:100 to 80:20, more preferably from 10:90 to 70:30. The composition may be used in a state with the alcohol present as is, or in some cases may be used after removing the alcohol by distillation. It is preferable to remove the alcohol as much as possible, since then there is the advantage that the reactor can be made smaller in other steps. As the removal process, the publicly known removal by distillation is preferable, and moreover the publicly known distillation equipment can be used as the distillation apparatus used in the distillation. As a preferable distillation apparatus, a thin film distillation apparatus can be preferably used since then the alcohol can be removed in a short time. There are no particular limitations on the form of the reactor for the dehydration reaction, it being possible to use a publicly known tank or column reactor. A low boiling point reaction mixture containing water is withdrawn from the reactor by distillation in a gaseous form, and a high boiling point reaction mixture containing the produced alkyltin alkoxide or alkyltin alkoxide mixture is withdrawn from a lower portion of the reactor in a liquid form. For the reactor, any of various publicly known types can be used, for example a type of reactor such as a stirred tank reactor, a multi-stage stirred tank reactor, a distillation column, a multi-stage distillation column, a multi-tubular reactor, a continuous multi-stage distillation column, a packed column, a thin film evaporator, a reactor having a support therein, a forced circulation reactor, a falling film evaporator, a falling droplet evaporator, a trickle phase reactor, or a bubble column, or a type in which such reactors are combined. From the viewpoint of efficiently shifting the equilibrium to the product system side, a process using a column reactor is preferable, and moreover a structure for which the gas-liquid contact area is large is preferable so that the produced water can be rapidly moved into the gas phase. A continuous process using a multi-tubular reactor, a multi-stage distillation column, or a packed column packed with a packing may be used, but the dialkyltin oxide used in the present step is generally solid, and hence a process in which the reaction is first carried out in a tank reactor and then the dialkyltin dialkoxide content is increased in a column reactor is most preferable. The material of the reactor and lines may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling.

ii) Alkyltin Alkoxide Regeneration Step (step 7)

This step is a step carried out after the residual liquid has been obtained in step 6, but is similar to the above alkyltin alkoxide synthesis step, and hence will be described now. This step is a step in which the residual liquid obtained in step 6 is subjected to a dehydration reaction with an alcohol represented by following formula (3), so as to regenerate the alkyltin alkoxide:

$$R^{11}OH \qquad (3)$$

wherein $R^{11}$ is the same as R in the OR groups in the mixture in step 1.

$R^{11}OH$ is an alcohol corresponding to R in the OR groups in the mixture in step 1; the OR groups in the mixture are the alkoxy groups (OR groups) obtained through the above alkyltin alkoxide synthesis step, and hence the same alcohol is used for the alcohol represented by formula (3) as the alcohol represented by chemical formula (30) used in the startup. Examples of this alcohol include alcohols given as examples for chemical formula (30). The conditions for the dehydration reaction are also preferably as for the alkyltin alkoxide synthesis step described above. The amount of the alcohol used is in a range of from 2 to 10 molar equivalents based on the number of mols of tin atoms contained in the residual liquid, the amount of the alcohol preferably being high so as to increase the proportion of the dialkyltin dialkoxide in the alkyltin alkoxide composition produced and/or increase the production rate. However, considering the size of the reactor and so on, the amount of the alcohol is preferably low. A preferable range is thus from 4 to 80 molar equivalents, more preferably from 4 to 50 molar equivalents. The reaction may be terminated once the desired alkyltin alkoxide composition has been obtained. The progress of the reaction can be determined by measuring the amount of water withdrawn out of the system, and can also be determined by sampling the reaction liquid and carrying out $^{119}$Sn-NMR. So that the mixture according to the present invention can be produced in step 1, the reaction is terminated once it has been confirmed that the alkyltin alkoxide composition has been obtained for which the molar ratio between the tetraalkyldialkoxydistannoxane and the dialkyltin dialkoxide contained in the composition is in a range of from 0:100 to 80:20, more preferably from 10:90 to 70:30. The composition may be used in a state with the alcohol present as is, or in some cases may be used after removing the alcohol by distillation. It is preferable to remove the alcohol as much as possible, since then there is the advantage that the reactor can be made smaller in other steps. As the removal process, the publicly known removal by distillation is preferable, and moreover the publicly known distillation equipment can be used as a distillation apparatus used in the distillation. As the preferable distillation apparatus, a thin film distillation apparatus can be preferably used since then the alcohol can be removed in a short time. The present step differs from the alkyltin alkoxide synthesis step in that dialkyltin oxide which is generally solid is not used, and hence there are few constraints on the reactor. There are thus no particular limitations on the form of the reactor for the dehydration reaction, it being possible to use the publicly known tank or column reactor. A low boiling point reaction mixture containing water is withdrawn from the reactor by distillation in a gaseous form, and a high boiling point reaction mixture containing the produced alkyltin alkoxide or alkyltin alkoxide mixture is withdrawn from a lower portion of the reactor in a liquid form. For the reactor, any of various publicly known types can be used, for example a type of reactor such as a stirred tank reactor, a multi-stage stirred tank reactor, a distillation column, a multi-stage distillation column, a multi-tubular reactor, a continuous multi-stage distillation column, a packed column, a thin film evaporator, a reactor having a support therein, a forced circulation reactor, a falling film evaporator, a falling droplet evaporator, a trickle phase reactor, or a bubble column, or a type in which such reactors are combined. From the viewpoint of efficiently shifting the equilibrium to the product system side, a process using a column reactor is preferable, and moreover a structure for which the gas-liquid contact area is large is preferable so that the produced water can be rapidly moved into the gas phase. A continuous process using a multi-tubular reactor, a multi-stage distillation column, or a packed column packed with a packing is particularly preferable. The material of the reactor and lines may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while a publicly known method such as natural cooling, cooling water or brine may be used for cooling.

iii) Carbonate-Producing Step (step 3)

As described above, when starting up the continuous reaction, the alkyltin alkoxides from the alkyltin alkoxide synthesis step may be directly transferred into the carbonate-producing step so as to produce the carbonate, or these alkyltin alkoxides may be used to obtain the mixture according to the present invention using fresh carbon dioxide, with the mixture then being transferred so as to produce the carbonate.

As the process for producing the carbonate from the alkyltin alkoxide composition transferred from the alkyltin alkoxide synthesis step and/or the mixture produced in step 1, a carbonate production process previously disclosed by the present inventors (e.g. WO 03/055840, WO 04/014840 etc.)

can be preferably used. As the reaction conditions, the carbonate-containing reaction liquid can be obtained by reacting for from 0.1 to 10 hours at a temperature in a range of from 110 to 200° C., preferably from 120 to 180° C., and a reaction pressure in a range of from 1.5 MPa to 20 MPa, preferably from 2.0 MPa to 10 MPa. The reaction is preferably terminated once the desired carbonate has been produced in the reactor. The progress of the reaction can be confirmed by sampling the reaction liquid in the reactor, and analyzing the produced carbonate using the method such as gas chromatography. For example, the reaction may be terminated once at least 10% has been produced based on the number of mols of the dialkyltin alkoxide and/or the carbon dioxide complex of the dialkyltin alkoxide contained in the alkyltin alkoxides and/or the carbon dioxide complex of the alkyltin alkoxide transferred into the reactor, and in the case of wishing to make the carbonate yield high, the reaction may be continued until this value is at least 90% before being terminated. As the reactor, the publicly known reactor can be used, it being preferable to use either a column reactor or a tank reactor. The material of the reactor and lines may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling.

iv) Carbon Dioxide-Releasing Step (step 4)

The reaction liquid obtained in step 3 is continuously withdrawn, and unused carbon dioxide contained in the reaction liquid is removed from the reaction liquid as a gaseous component. The temperature in this step depends on the pressure, but is in a range of from 80 to 200° C., and considering productivity, is preferably in a range of from 100 to 200° C.; at high temperature the thermolysis of tin compounds contained in the mixture may occur, and hence a range of from 100 to 150° C. is most preferable. The pressure depends on the temperature, but a pressure of from normal pressure to reduced pressure is generally used, and considering productivity, a range of from 100 Pa to 80 kPa is particularly preferable, from 100 Pa to 50 kPa being most preferable. The present step can be carried out for a time in a range of from 0.01 to 10 hours, but in the case of carrying out the step for a long time, at high temperature the thermolysis of tin compounds contain in the mixture may occur, and hence a range of from 0.01 to 0.5 hours is preferable, a range of from 0.01 to 0.3 hours being most preferable. The present step may be terminated once at least 20% of the unused carbon dioxide has been withdrawn, or in the case of wishing to increase the unused carbon dioxide usage ratio, may be terminated once at least 90% has been withdrawn. Considering using the carbon dioxide efficiently, it is preferable to withdraw as much as possible of the unused carbon dioxide as the gaseous component. As the reactor, the publicly known reactor can be used, it being preferable to use either a column reactor or a tank reactor. The most preferable reactor is a thin film evaporator or a thin film distillation apparatus. The material of the reactor and lines may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling.

v) Unused Carbon Dioxide Gas Recycling Step (Step 5)

This is a step of recycling the gaseous carbon dioxide separated out in step 4 into step 1. The carbon dioxide withdrawn in step 4 is transferred into the reactor of step 1, and moreover is adjusted to the pressure used in step 1. Specifically, the reaction condition in step 1 is from normal pressure to 1 MPa, and so that the mixture obtained in step 1 exists stably, a range of from normal pressure to 0.6 MPa is more preferable; the gaseous carbon dioxide withdrawn in step 4 is thus adjusted to such a pressure. The publicly known method can be used as the method of adjusting the pressure. Examples thereof include a method using a jet turbine, and a method using a compressor. At the same time, in the case that the gaseous carbon dioxide contains impurities, purification may be carried out in the present step. The material of the reactor and lines may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling.

vi) Carbon Dioxide Complex Production Step (Step 1)

The alkyltin alkoxide composition supplied into this step may be supplied from the alkyltin alkoxide synthesis step upon startup or may be supplied from the alkyltin alkoxide regeneration step, i.e. step 7, during continuous production. As the gaseous carbon dioxide used, fresh carbon dioxide is supplied in upon startup, and recycled carbon dioxide supplied from step 5 is supplied in during continuous production. During the continuous production, fresh carbon dioxide may also be supplied in together with the recycled carbon dioxide. The carbon dioxide may be supplied in continuously or intermittently. The mixture containing the carbon dioxide complex of the alkyltin alkoxide can be obtained by absorbing the gaseous carbon dioxide into the alkyltin alkoxide composition, and bringing about chemical reaction. When carrying out the chemical reaction, the reaction is carried out with the alkyltin alkoxide composition in a liquid or liquefied form. The heating method can be preferably used for the liquefaction. Moreover, as described in the section on producing the mixture according to the present invention, the liquefaction may also be carried out by using a solvent or the like. The reaction pressure depends on the reaction temperature, but is preferably in a range of from normal pressure to 1 MPa, and so that the mixture according to the present invention obtained exists stably, a range of from normal pressure to 0.6 MPa is more preferable. The reaction temperature depends on the reaction pressure, but in the case of high temperature and high pressure a carbonate is readily produced so that the mixture according to the present invention tends to no longer exist stably, and hence to obtain the mixture accordingly the present invention, a range of from −40 to 80° C. is preferable; furthermore, the objective of the mixture according to the present invention is to be transferred into step 2, and hence considering the fluidity during the transfer, a range of from 0 to 80° C. is more preferable, the most preferable range being from room temperature (approximately 20° C.) to 80° C. The reaction is preferably carried out with a reaction time of from a few seconds to 100 hours, and considering productivity and so on, a range of from a few minutes to 10 hours is preferable. As the reactor, the publicly known tank reactor or column reactor can be used. Moreover, a plurality of reactors may be used in combination. The carbon dioxide absorbing efficiency of the alkyltin alkoxide composition is higher for the compound represented by formula (1) than for the compound represented by formula (2) at high temperature, and hence it is preferable to carry out the reaction while controlling the individual temperatures in the plurality of reactors in accordance with the ratio between the compounds of formulae (1) and (2) in the composition. The reaction is a reaction between carbon dioxide gas (a gas) and the alkyltin alkoxide composition (a liquid), and hence to carry out the reaction efficiently, it is preferable to make the gas-liquid interface large so that the gas-liquid contact area is large. The publicly known method can be used for carrying out the reaction with a large gas-liquid interface. For example, with a tank reactor, a method in which the stirring rate is increased or gas bubbles are formed in the liquid is preferable, whereas with a column reactor, a method in which a packed column is used or a tray column is used is preferable. As examples of such a column reactor, there can be used, for example, a tray column using trays such as bubble-cap trays, sieve trays, valve trays or counterflow trays, or a packed column packed with any of various packings such as Raschig rings, Lessing rings, Pall rings, Berl saddles, Intalox saddles, a Dixon packing, a McMahon packing, Heli-Pak, a Sulzer packing or Mellapak. The material of the reactor and lines may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling. The reaction is generally an exothermic reaction, and hence cooling may be carried out, or the reactor may be allowed to cool through heat dissipation. Alternatively, if the objective is to carry out a carbonate-producing reaction at the same time, then heating may be carried out. The publicly known method can be used to cool or heat the reactor, for example a method using a jacket, or a method using an internal coil. The carbon dioxide gas and the alkyltin alkoxide composition supplied into the reactor may be supplied into the reactor separately, or may be mixed together before being supplied into the reactor. The supply may be carried out from a plurality of sites on the reactor. Completion of the reaction may be determined by NMR analysis as described earlier. The mixture in the reaction liquid is analyzed, and the reaction is terminated once a mixture has been obtained for which, taking the number of mols of tin atoms in the alkyltin alkoxide and/or the carbon dioxide complex of the alkyltin alkoxide contained in the mixture to be Z, taking carbon dioxide incorporated in the carbon dioxide complex of the alkyltin alkoxide, and carbon dioxide contained in the mixture to be ($CO_2$), and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide, in the relationship Z:$(CO_2)_x$:$(OR)_y$, the molar proportion represented by x is in a range of from 0.1 to 2, and the molar proportion represented by y is in a range of from 0.5 to 2. x is preferably in a range of from 0.1 to 1.5 more preferably from 0.5 to 1.5, and y is preferably in a range of from 0.5 to 1.5. In the case that the value of x or y deviates from such a preferable range, adjustment may be carried out by supplying in alkyltin alkoxides from the alkyltin alkoxide synthesis step or the alkyltin alkoxide regeneration step.

vii) Carbon Dioxide Complex Transfer Step (Step 2)

The mixture obtained in step 1 can be transferred in a liquid or liquefied form, and hence it is very easy to carry out the transfer quantitatively using a liquid feeding pump or the like. The mixture is intended to be transferred in a liquid or liquefied form, but in some cases may be transferred in a solid state. The mixture is preferably transferred as a liquid or in a liquefied form. When transferring the liquid or liquefied mixture, to transfer the mixture stably, the transfer is preferably carried out at a temperature in a range of from −40 to 80° C. Moreover, considering the fluidity during the transfer, a range of from 0 to 80° C. is more preferable, the most preferable range being from room temperature (approximately 20° C.) to 80° C. Other components may be added to the mixture so long as the transfer of the mixture and the recovery and utilization of carbon dioxide are not affected. Examples of such non-affecting components include primary alkyl alcohols, other tin components (e.g. a tetraalkyltin, a tetraalkoxytin, or a monoalkyltin hydroxide, and so long as the transfer is not affected a dialkyltin oxide or tin oxide may also be contained), solvents (ether solvents, aromatic solvents, aliphatic solvents etc. that do not adversely affect the transfer), and inert gases (e.g. nitrogen gas, argon gas, helium gas, methane gas, carbon dioxide gas etc.). Examples of solvents include methanol, ethanol, propanol (isomers), butanol (isomers) pentanol (isomers), hexanol (isomers), heptanol (isomers), tetrahydrofuran, dioxane, benzene, toluene, and xylene (isomers); in the case of using an alcohol, it is preferable in terms of the stability of the mixture to use an alcohol having an alkyl group the same as the alkyl group in the alkoxy groups of an alkyltin alkoxide contained in the alkyltin alkoxide composition. The pressure during the transfer is preferably in a range of from normal pressure to 1 MPa, and so that the mixture obtained exists stably, a range of from normal pressure to 0.6 MPa is more preferable, with a range of from normal pressure to 0.6 MPa being most preferable. The present step is a step of transferring into step 3, and at the stage of supplying the mixture into the reactor in step 3, the pressure may be different to the above. The mixture is a stable mixture, but is subject to hydrolysis as with an ordinary metal alkoxide, and hence during the transfer, it is preferable to pay heed to water to an extent that would be apparent to a person skilled in the art. In the case that the mixture contains carbonate, the carbonate content is preferably not more than 20 mol % based on the number of mols of the tetraalkyldialkoxydistannoxane in the alkyltin alkoxide composition in the mixture, and in the case that the composition contains dialkyltin oxide, the carbonate content is preferably also not more than 20 mol % based on the dialkyltin oxide. This is because in the case that carbonate is present, excess carbon dioxide may be produced, and hence the mixture may become unstable. Furthermore, it is undesirable for the mixture to contain the carbonate, since then the amount of carbonate newly produced may decrease. For the transfer of the mixture according to the present invention, the material of a transfer line or the like may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling.

viii) Carbonate Separation Step (Step 6)

This step is a step of separating out the carbonate from the reaction liquid remaining after the unused carbon dioxide gas has been recovered in step 4, thus obtaining a residual liquid. For the separation process, the publicly known process and apparatus can be suitably used. A preferable process is one using distillation. The reaction liquid transferred from step 4 is subjected to batch, semi-batch style, or continuous distillation, so as to obtain the carbonate and the residual liquid. A preferable distillation process is one in which the reaction liquid is supplied into a distillation apparatus, and the carbonate is separated out of the system from an upper portion of the distillation apparatus as a gas phase component, while the residual liquid is withdrawn from the bottom of the distillation apparatus as a liquid component. The temperature in the present step depends on the boiling point of the carbonate and the pressure, but is preferably in a range of from room temperature (e.g. 20° C.) to 200° C., and because at the high temperature the thermolysis of tin compounds in the residual liquid may occur or the amount of carbonate may decrease through a reverse reaction, is particularly preferably in a range of from room temperature (e.g. 20° C.) to 150° C. The pressure depends on the type of the carbonate and the temperature used, but is generally from normal pressure to reduced pressure, and considering productivity, a range of from 100 Pa to 80 kPa is preferable, from 100 Pa to 50 kPa being particularly preferable. The present step can be carried out for a time in a range of from 0.01 to 10 hours, but in the case of carrying out the step for a long time, at the high temperature the thermolysis of tin compounds in the residual liquid may occur or the amount of carbonate may decrease through a reverse reaction, and hence a range of from 0.01 to 0.5 hours is preferable, a range of from 0.01 to 0.3 hours being particularly preferable. As the distillation apparatus, the publicly known distillation apparatus can be used; a column type distillation apparatus or a tank type distillation apparatus can be preferably used, or a plurality of such apparatuses may be used in combination. A particularly preferable distillation apparatus is a thin film evaporator or a thin film distillation apparatus, a thin film evaporator or thin film distillation apparatus having a distillation column being most preferable. The material of the distillation apparatus and lines may be any publicly known material that does not have an adverse effect, but SUS 304, SUS 316, SUS 316L or the like is inexpensive and can thus be preferably used. Instrumentation such as a flow meter and a thermometer and the publicly known process equipment such as a reboiler, a pump, and a condenser may be added as required, and the publicly known method such as steam or a heater may be used for heating, while the publicly known method such as natural cooling, cooling water or brine may be used for cooling.

The respective steps have been described in detail above, but other steps as described below may be added as required. For example, there may be added a step or apparatus within the scope envisagable by a person skilled in the art such as a step of separating out thermolysis matter produced from an alkyltin alkoxide, a step of removing a by-product out of the system, a step of purifying the alcohol, a step of purifying the carbonate, or a step of disposing of a by-product through incineration or the like.

The carbonate obtained through the above process can be suitably used as a starting material for a polycarbonate, a starting material for an isocyanate, or a starting material for another chemical, or as an electrolyte for a battery such as a lithium ion battery. Through the above process, carbon dioxide which has hitherto been discharged into the atmosphere without being used can be effectively recovered and reused, and hence the process is very useful industrially.

Moreover, according to the process of the present invention, the carbon dioxide gas recovery can all be carried out in a nonaqueous system, and moreover can be carried out under mild conditions with a recovery reaction temperature of not more than 100° C. Moreover, even if the carbon dioxide gas contains water, the water is consumed through alkyltin alkoxide hydrolysis, and hence the carbon dioxide gas discharged from the mixture after the recovery (in the case that there is an excess of water, solid matter may also be produced through the hydrolysis reaction) can be extracted with a very low water content. The present invention is thus very useful industrially.

EXAMPLES

Following is a detailed description of the present invention through examples. However, the present invention is not limited to these examples. Other than the following examples, a person skilled in the art could implement the present invention with various modifications within the scope of the claims of the specification of the present application, and such modifications are deemed to be included under the scope of the claims of the present application.

Analysis Methods
1) NMR Analysis Method

Apparatus: JNM-A400 FT-NMR system made by JEOL Ltd., Japan (1) Preparation of $^1$H-NMR/$^{13}$C-NMR/$^{119}$Sn-NMR Analysis Sample 0.3 g of a tin compound was weighed out, and approximately 0.7 g of deuterated chloroform (made by Aldrich, 99.8%) and 0.08 g of tetramethyltin (made by Wako, Wako 1$^{st}$ Grade) as an $^{119}$Sn-NMR internal standard were added, and the solution was mixed to uniformity, thus obtaining an NMR analysis sample.

(2) Quantitative Analysis Method

Quantitative analysis was carried out on the analysis sample solution based on a calibration curve obtained by carrying out analysis on reference samples of various reference substances.

(3) Calculation Method for Alkyltin Alkoxide Yield

The alkyltin alkoxide yield was calculated as mol % produced, this being the number of mols of tin atoms in each alkyltin alkoxide obtained based on the number of mols of tin atoms in the starting material dialkyltin oxide.

2) Analysis Method for Water

Apparatus: CA-05 trace moisture meter made by Mitsubishi Chemical Corporation, Japan (1) Quantitative Analysis Method for Liquid Sample The analysis sample was collected using a syringe and the weight was measured, and then the sample was injected as is into the water meter and the amount of water was measured. After that, the weight of the syringe was again measured, and hence the amount of the sample injected was calculated, and then the water content in the sample was determined.

(2) Quantitative Analysis Method for Gaseous Sample

The analysis sample was collected using a gas-tight syringe, and injected as is into the water meter and the amount of water was measured. The water content based on the volume of the injected sample was determined.

3) Gas Chromatography Analysis Method for Carbonate

Apparatus: GC-2010 system made by Shimadzu Corporation, Japan (1) Preparation of Analysis Sample Solution 0.2 g of the reaction solution was weighed out, and approximately 1.5 g of dehydrated acetone was added. Approximately 0.04 g of toluene or diphenyl ether was further added as an internal standard, thus obtaining a gas chromatography analysis sample solution.

(2) Gas Chromatography Analysis Conditions
Column: DB-1 (made by J&W Scientific, USA)
Liquid phase: 100% dimethyl polysiloxane
Length: 30 m
Inside diameter: 0.25 mm
Film thickness: 1 μm
Column temperature: 50° C. (rising by 10° C./min) 300° C.
Injection temperature: 300° C.
Detector temperature: 300° C.
Detection method: FID (3) Quantitative Analysis Method Quantitative analysis was carried out on the analysis sample solution based on a calibration curve obtained by carrying out analysis on reference samples of various reference substances.

4) Gas Chromatography Analysis Method for Carbon Dioxide Gas

Apparatus: GC-14B system made by Shimadzu Corporation, Japan (1) Pretreatment of Analysis Sample A sulfuric acid aqueous solution was added to the carbon dioxide complex-containing mixture, and the carbon dioxide gas produced was collected using a gas-tight syringe and analysis was carried out.

(2) Gas Chromatography Analysis Conditions
Column: Silica gel 60-80 (SUS column)
Length: 3 m
Inside diameter: 3 mm
Column temperature: 70° C.
Injection temperature: 200° C.
Detector temperature: 100° C.
Detection method: TCD (3) Quantitative Analysis Method Quantitative analysis was carried out on the analysis sample solution based on a calibration curve obtained by carrying out analysis on reference samples of various reference substances.

Example 1

Step A: Production of Tetraalkyldialkoxydistannoxane 672 g (2.7 mol) of dibutyltin oxide (made by Sankyo Organic Chemicals Co., Ltd., Japan) and 1900 g (21.5 mol) of 3-methyl-1-butanol (made by Kuraray Co., Ltd., Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to approximately 145° C., and the flask was immersed in the oil bath and rotation of the evaporator was commenced. With the purge valve of the evaporator left open, rotational stirring and heating were carried out for approximately 40 minutes at normal pressure, whereupon the liquid mixture boiled, and hence distilling off of water-containing 3-methyl-1-butanol began. This state was maintained for 7 hours, and then the purge valve was closed, and the pressure in the system was gradually reduced, and excess 3-methyl-1-butanol was distilled off with the pressure in the system at from 74 to 35 kPa. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 880 g of reaction liquid was obtained in the flask. According to $^{119}$Sn—, $^{1}$H—, and $^{13}$C-NMR analysis results, the product 1,1,3,3-tetrabutyl-1,3-bis(3-methylbutyloxy)-distannoxane was obtained at a yield of 99% based on the dibutyltin oxide. The same procedure was carried out so as to produce 1,1,3,3-tetrabutyl-1,3-bis(3-methylbutyloxy)-distannoxane to be used in the following step B.

Step B: Production of Carbon Dioxide Complex-Containing Mixture

Figure 4:
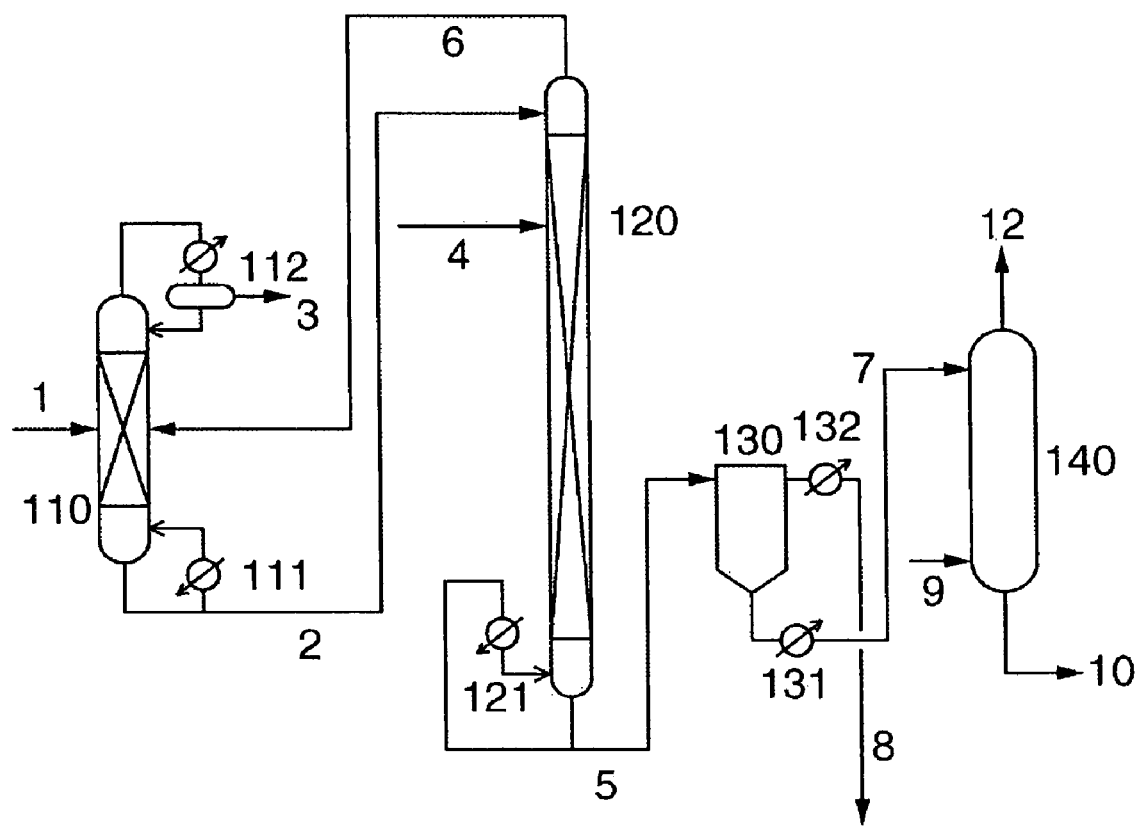
FIG. 4 shows a schematic diagram of an apparatus for producing a mixture containing an alkyltin alkoxide composition and carbon dioxide complex.
Figure 7:
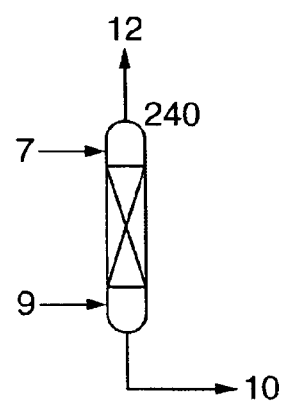
FIG. 7 shows a schematic diagram of an apparatus for producing a carbon dioxide complex-containing mixture.

A carbon dioxide complex-containing mixture was produced using an apparatus as shown in FIG. 4. The 1,1,3,3-tetrabutyl-1,3-bis(3-methylbutyloxy)-distannoxane produced in step A was supplied at 1200 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 23000 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 20000 g/hr of water-containing 3-methyl-1-butanol was transferred from an upper portion of the reactor via a transfer line 6, and approximately 322 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 99 wt % of dibutyl-bis(3-methylbutyloxy)tin. The composition was cooled to approximately 15° C. using a cooler 131, and transferred into an upper portion of a carbon dioxide complex production apparatus 140 at a flow rate of approximately 1490 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 90 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at normal pressure at a temperature of 20° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=1.03 and y=1.99.

Figure 12:
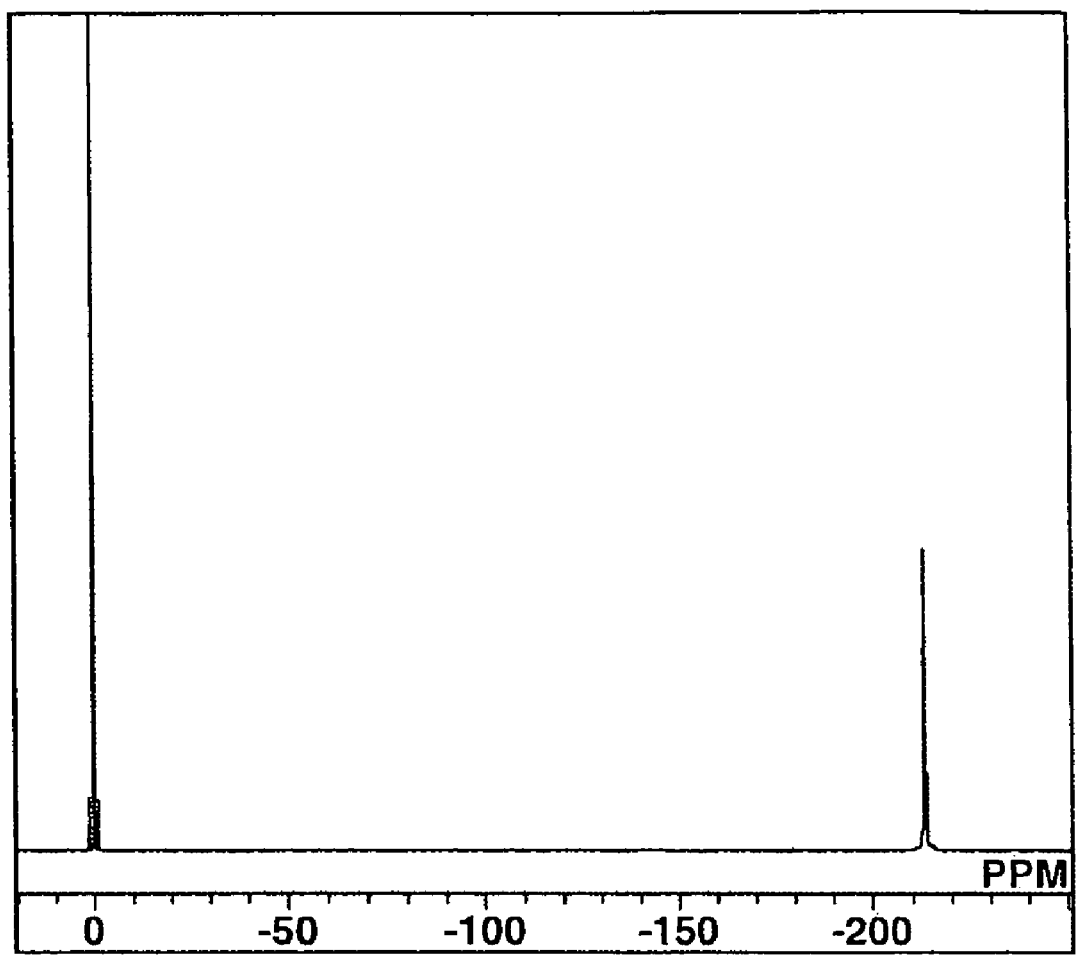
FIG. 12 shows a $^{119}$Sn-NMR spectrum of a carbon dioxide complex-containing mixture.
Figure 13:
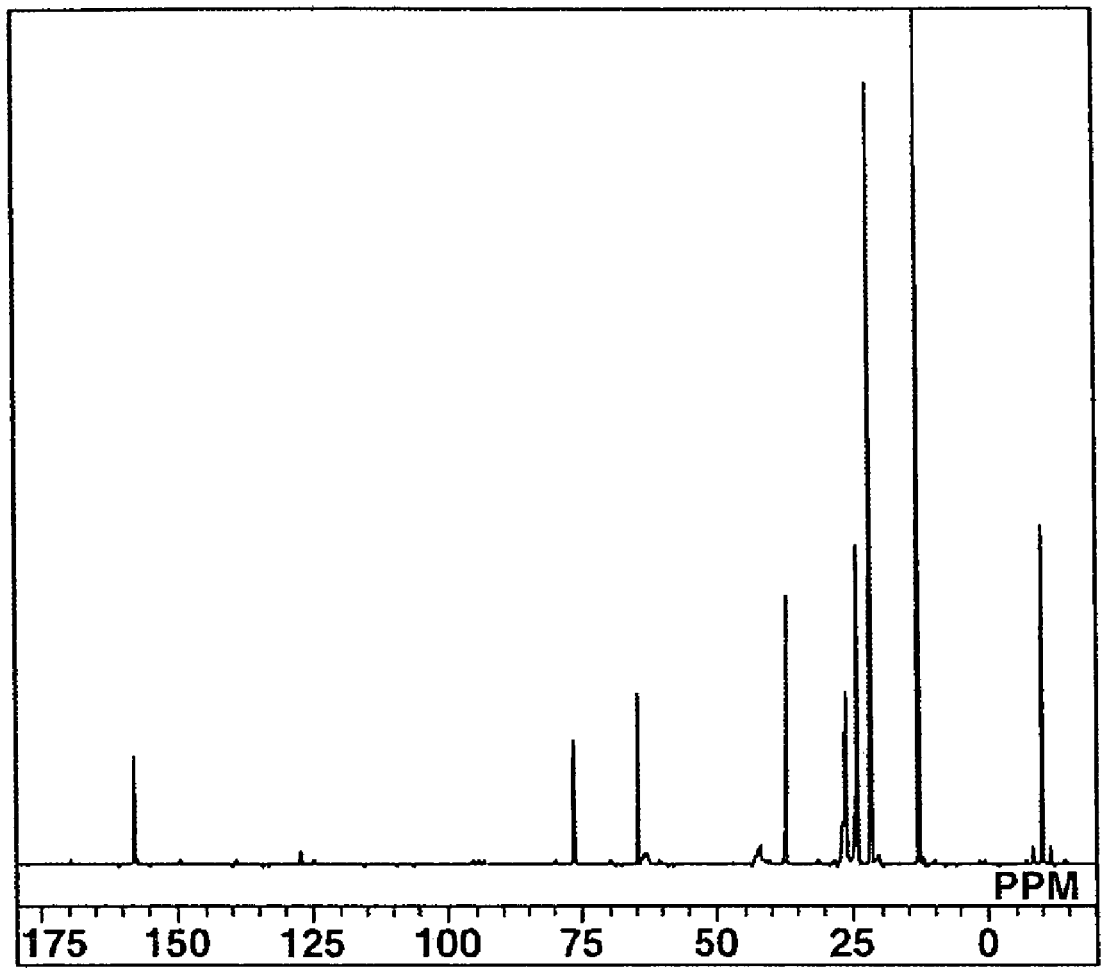
FIG. 13 shows a $^{13}$C-NMR spectrum of the carbon dioxide complex-containing mixture.
Figure 14:
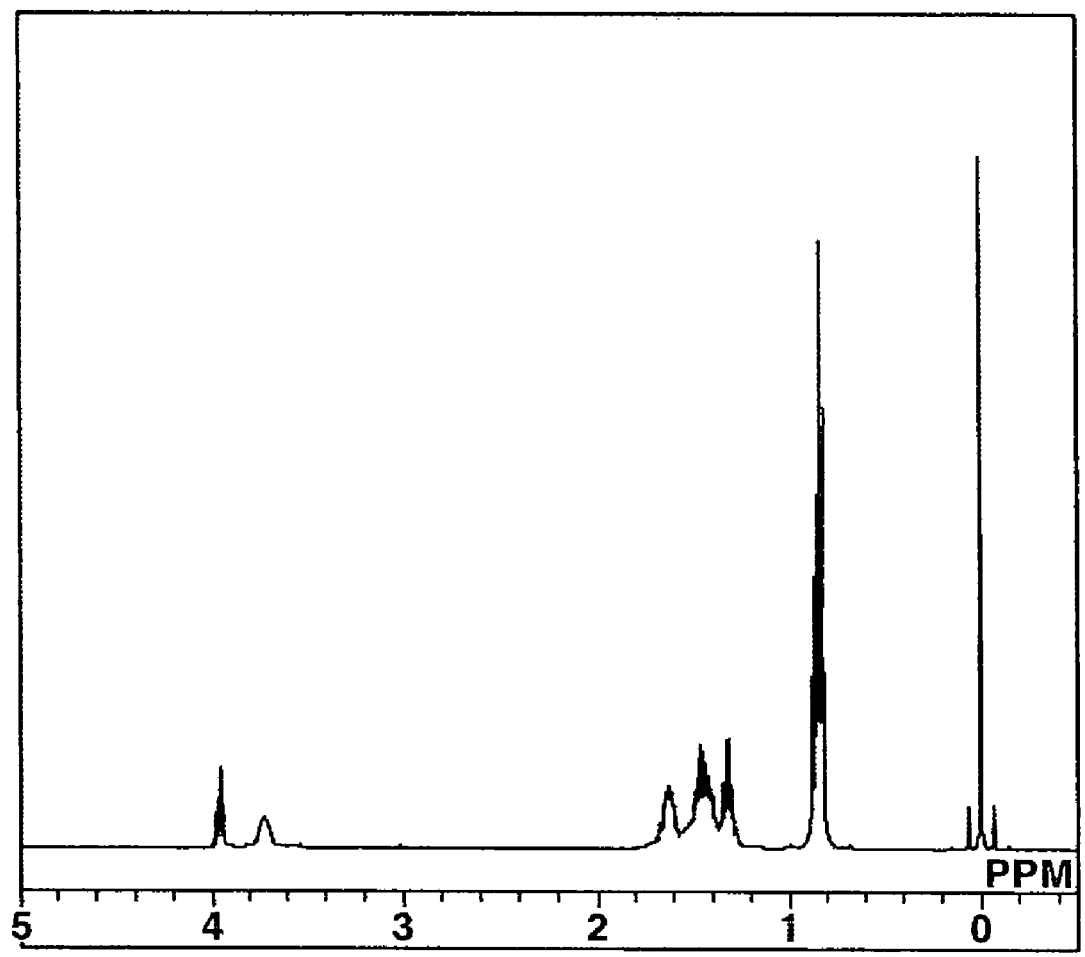
FIG. 14 shows a $^{1}$H-NMR spectrum of the carbon dioxide complex-containing mixture.

NMR analysis results are shown in FIG. 12 ($^{119}$Sn-NMR), FIG. 13 ($^{13}$C-NMR), and FIG. 14 ($^1$H-NMR). ($^{119}$Sn-NMR (based on tetramethyltin): −212.2 ppm; $^1$H-NMR (based on tetramethyltin): 3.97 ppm (2H, t), 3.73 ppm (2H, broad), 1.71-1.59 ppm (6H, m), 1.49-1.28 ppm (12H, m), 0.80-0.90 ppm (18H, m); $^{13}$C-NMR: 158.4 ppm, 65.0 ppm, 63.9 ppm, 42.4 ppm, 37.6 ppm, 26.7 ppm, 26.4 ppm, 25.0 ppm, 24.6 ppm, 22.4 ppm, 22.1 ppm, 13.1 ppm.)

Example 2

Step A: Production of Tetraalkyldialkoxydistannoxane 672 g (2.7 mol) of dibutyltin oxide (made by Sankyo Organic Chemicals Co., Ltd., Japan) and 1102 g (10.8 mol) of 2-ethyl-1-butanol (made by Chisso Corporation, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 157° C., and the flask was immersed in the oil bath and rotation of the evaporator was commenced. With the purge valve of the evaporator left open, rotational stirring and heating were carried out for approximately 40 minutes at normal pressure, and then the purge valve was closed, and the pressure in the system was gradually reduced, and water-containing 2-ethyl-1-butanol was distilled off with the pressure in the system at from 84 to 65 kPa. This state was maintained for 2 hours, and then the pressure in the system was further reduced, and excess 2-ethyl-1-butanol was distilled off. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 883 g of reaction liquid was obtained in the flask. According to $^{119}$Sn—, $^1$H—, and $^{13}$C-NMR analysis results, the product 1,1,3,3-tetrabutyl-1,3-bis(2-ethylbutyloxy)-distannoxane was obtained at a yield of. 99% based on the dibutyltin oxide. The same procedure was carried out so as to produce 1,1,3,3-tetrabutyl-1,3-bis(2-ethylbutyloxy)-distannoxane to be used in the following step B.

Step B: Production of Carbon Dioxide Complex-Containing Mixture

A carbon dioxide complex-containing mixture was produced using a continuous production apparatus as shown in FIG. 4. The 1,1,3,3-tetrabutyl-1,3-bis(2-ethylbutyloxy)-distannoxane was supplied at 1500 g/hr from a transfer line 4 into a column reactor 120 of inside diameter 151 mm and effective length 5040 mm packed with a Metal Gauze CY packing (made by Sulzer. Chemtech Ltd., Switzerland), and 2-ethyl-1-butanol (made by Chisso Corporation, Japan) that had been purified in a distillation column 110 was supplied at 24000 g/hr from a transfer line 2 into the column reactor 120. The liquid temperature in the reactor was adjusted to 160° C. using a heater and a reboiler 121, and the pressure was adjusted to approximately 31 kPa-G using a pressure regulating valve. The residence time in the reactor was approximately 17 minutes. Approximately 16000 g/hr of water-containing 2-ethyl-1-butanol was transferred from an upper portion of the reactor via a transfer line 6, and approximately 448 g/hr of 2-ethyl-1-butanol (made by Chisso Corporation, Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 2-ethyl-1-butanol was transferred out via the transfer line 2 from a lower portion of the distillation column 110. An alkyltin alkoxide composition containing dibutyl-bis(2-ethylbutyloxy)tin was obtained from a lower portion of the column reactor 120, and was supplied into a thin film evaporator 130 (made by Kobelco Eco-Solutions Co., Ltd., Japan) via a transfer line 5. 2-Ethyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 90 wt % of dibutyl-bis(2-ethylbutyloxy)tin and approximately 10 wt % of 2-ethyl-1-butanol. The composition was cooled to approximately 0° C. using a cooler 131, and transferred at a flow rate of approximately 2100 g/hr via a transfer line 7 into an upper portion of a carbon dioxide complex production apparatus 140 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 650 g/hr via a transfer line 9 into a lower portion of the column reactor 240. The pressure in the column was adjusted to 1 MPa-G The reaction temperature in the column reactor 240 was adjusted to 0° C., and a carbon dioxide complex-containing mixture was produced. The carbon dioxide complex-containing mixture obtained was a liquid, and was transferred out at a temperature of 0° C. and a pressure of 1 MPa-G via a transfer line 10, it being possible to carry out the transfer via the transfer line 10 without problems such as blockage of the transfer line occurring. The mixture was sampled, and subjected to elemental analysis, whereupon the molar ratio between tin atoms, carbon dioxide, and OR groups in the carbon dioxide complex ($Z:(CO_2)_x:(OR)_y$) was found to be such that x=1.99 and y=1.99.

Example 3

Step A: Production of Tetraalkyldialkoxydistannoxane 692 g (2.78 mol) of dibutyltin oxide (made by Sankyo Organic Chemicals Co., Ltd., Japan) and 2000 g (27 mol) of 1-butanol (made by Wako, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 126° C., and the flask was immersed in the oil bath and rotation of the evaporator was commenced. With the purge valve of the evaporator left open, rotational stirring and heating were carried out for approximately 30 minutes at normal pressure, whereupon the liquid mixture boiled, and hence distilling off of a low boiling component began. This state was maintained for 8 hours, and then the purge valve was closed, and the pressure in the system was gradually reduced, and residual low boiling component was distilled off with the pressure in the system at from 76 to 54 kPa. Once low boiling component stopped coming off, the flask was lifted out from the oil bath. The reaction liquid was a transparent liquid. After lifting the flask out from the oil bath, the purge valve was gradually opened, so as to return the pressure in the system to normal pressure. 952 g of reaction liquid was obtained in the flask. According to $^{119}$Sn—, $^1$H—, and $^{13}$C-NMR analysis results, the product 1,1,3,3-tetrabutyl-1,3-di(butyloxy)-distannoxane was obtained at a yield of 99% based on the dibutyltin oxide. The same procedure was carried out so as to produce 1,1,3,3-tetrabutyl-1,3-di(butyloxy)-distannoxane to be used in the following step B.

Step B: Production of Carbon Dioxide Complex-Containing Mixture

A carbon dioxide complex-containing mixture was produced using an apparatus as shown in FIG. 4. The 1,1,3,3-tetrabutyl-1,3-di(butyloxy)-distannoxane produced in step A was supplied at 1200 g/hr from a transfer line 4 into a column reactor 120 of inside diameter 151 mm and effective length 5040 mm packed with a Mellapak 750Y packing (made by Sulzer Chemtech Ltd., Switzerland), and 1-butanol (made by Wako Pure Chemical Industries, Ltd., Japan) that had been purified in a distillation column 110 was supplied at 25000 g/hr from a transfer line 2 into the column reactor 120. The liquid temperature in the reactor was adjusted to 150° C. using a heater and a reboiler 121, and the pressure was adjusted to approximately 160 kPa-G using a pressure regulating valve. The residence time in the reactor was approximately 17 minutes. Approximately 18000 g/hr of water-containing 1-butanol was transferred from an upper portion of the reactor via a transfer line 6, and approximately 283 g/hr of 1-butanol (made by Wako Pure Chemical Industries, Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 1-butanol was transferred out via the transfer line 2 from a lower portion of the distillation column 110. An alkyltin alkoxide composition containing dibutyltin dibutoxide and 1,1,3,3-tetrabutyl-1,3-di(butyloxy)-distannoxane was obtained from a lower portion of the column reactor 120, and was supplied into a thin film evaporator 130 (made by Kobelco Eco-Solutions Co., Ltd., Japan) via a transfer line 5. 1-Butanol was evaporated off using the thin film evaporator 130, and recovered from a transfer line 8 via a condenser 132. The alkyltin alkoxide composition was obtained from a lower portion of the thin film evaporator 130, this composition containing approximately 90 mol % of dibutyltin dibutoxide and approximately 10 mol % of 1,1,3,3-tetrabutyl-1,3-di(butyloxy)-distannoxane. The composition was cooled to approximately 15° C. using a cooler 131, and transferred at a flow rate of approximately 1545 g/hr via a transfer line 7 into an upper portion of a carbon dioxide complex production apparatus 140. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at 0.4 MPa-G at approximately 100 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at a temperature of 20° C. and a pressure of 0.4 MPa-G via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture ($Z:(CO_2)_x:(OR)_y$) was found to be such that x=1.16 and y=1.90.

Example 4

Step A: Production of Tetraalkyldialkoxydistannoxane 700 g (1.94 mol) of dioctyltin oxide (made by Sankyo Organic Chemicals Co., Ltd., Japan) and 1700 g (19.3 mol) of 3-methyl-1-butanol (made by Kuraray Co., Ltd., Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 143° C., and the flask was immersed in the oil bath and rotation of the evaporator was commenced. With the purge valve of the evaporator left open, rotational stirring and heating were carried out for approximately 40 minutes at normal pressure, whereupon the liquid mixture boiled, and hence distilling off of a low boiling component began. This state was maintained for 7 hours, and then the purge valve was closed, and the pressure in the system was gradually reduced, and residual low boiling component was distilled off with the pressure in the system at from 76 to 32 kPa. Once low boiling component stopped coming off, the flask was lifted out from the oil bath. The reaction liquid was a transparent liquid. After lifting the flask out from the oil bath, the purge valve was gradually opened, so as to return the pressure in the system to normal pressure. 864 g of reaction liquid was obtained in the flask. According to $^{119}$Sn—, $^1$H—, and $^{13}$C-NMR analysis results, the product 1,1,3,3-tetraoctyl-1,3-bis(3-methylbutyloxy)-distannoxane was obtained at a yield of 99% based on the dioctyltin oxide. The same procedure was carried out so as to produce 1,1,3,3-tetraoctyl-1,3-bis(3-methylbutyloxy)-distannoxane to be used in the following step B.

Step B: Production of Carbon Dioxide Complex-Containing Mixture

A carbon dioxide complex-containing mixture was produced using an apparatus as shown in FIG. 4. The 1,1,3,3-tetraoctyl-1,3-bis(3-methylbutyloxy)-distannoxane produced in step A was supplied at 1200 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 24000 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 20000 g/hr of water-containing 3-methyl-1-butanol was transferred from an upper portion of the reactor via a transfer line 6, and approximately 240 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 99 wt % of dioctyl-bis(3-methyl-butyloxy)tin. The composition was cooled to approximately 50° C. using a cooler 131, and transferred into an upper portion of a carbon dioxide complex production apparatus 140 at a flow rate of approximately 1420 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of 0.4 MPa-G at approximately 125 g/hr via a transfer line 9 into a lower portion of the column reactor 240. The reaction temperature in the column reactor 240 was adjusted to approximately 60° C., and a carbon dioxide complex-containing mixture was produced. The mixture was a liquid, and was transferred out at a temperature of 60° C. and a pressure of 0.4 MPa-G via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture $(Z:(CO_2)_x:(OR)_y)$ was found to be such that $x=1.01$ and $y=1.99$.

Example 5

Step A: Production of Tetraalkyldialkoxydistannoxane 700 g (1.94 mol) of dioctyltin oxide (made by Sankyo Organic Chemicals Co., Ltd., Japan) and 1102 g (10.8 mol) of 2-ethyl-1-butanol (made by Chisso Corporation, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 157° C., and the flask was immersed in the oil bath and rotation of the evaporator was commenced. With the purge valve of the evaporator left open, rotational stirring and heating were carried out for approximately 40 minutes at normal pressure, and then the purge valve was closed, and the pressure in the system was gradually reduced, and water-containing 2-ethyl-1-butanol was distilled off with the pressure in the system at from 84 to 65 kPa. This state was maintained for 2 hours, and then the pressure in the system was further reduced, and excess 2-ethyl-1-butanol was distilled off. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 883 g of reaction liquid was obtained in the flask. According to $^{119}$Sn—, $^1$H—, and $^{13}$C-NMR analysis results, the product 1,1,3,3-tetraoctyl-1,3-bis(2-ethylbutyloxy)-distannoxane was obtained at a yield of 99% based on the dioctyltin oxide.

The same procedure was carried out so as to produce 1,1,3,3-tetraoctyl-1,3-bis(2-ethylbutyloxy)-distannoxane to be used in the following step B.

Step B: Production of Carbon Dioxide Complex-Containing Mixture

A carbon dioxide complex-containing mixture was produced using a continuous production apparatus as shown in FIG. 4. The 1,1,3,3-tetraoctyl-1,3-bis(2-ethylbutyloxy)-distannoxane was supplied at 3500 g/hr from a transfer line 4 into a column reactor 120 of inside diameter 151 mm and effective length 5040 mm packed with a Metal Gauze CY packing (made by Sulzer Chemtech Ltd., Switzerland), and 2-ethyl-1-butanol (made by Chisso Corporation, Japan) that had been purified in a distillation column 110 was supplied at 6000 g/hr from a transfer line 2 into the column reactor 120. The liquid temperature in the reactor was adjusted to 150° C. using a heater and a reboiler 121, and the pressure was adjusted to approximately −2 kPa-G using a pressure regulating valve. The residence time in the reactor was approximately 17 minutes. Approximately 4000 g/hr of water-containing 2-ethyl-1-butanol was transferred from an upper portion of the reactor via a transfer line 6, and approximately 390 g/hr of 2-ethyl-1-butanol (made by Chisso Corporation, Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 2-ethyl-1-butanol was transferred out via the transfer line 2 from a lower portion of the distillation column 110. An alkyltin alkoxide composition containing dioctyl-bis(2-ethylbutyloxy)tin was obtained from a lower portion of the column reactor 120, and was supplied into a thin film evaporator 130 (made by Kobelco Eco-Solutions Co., Ltd., Japan) via a transfer line 5. 2-Ethyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 60 mol % of dioctyl-bis(2-ethylbutyloxy)tin and approximately 40 mol % of 1,1,3,3-tetraoctyl-1,3-bis(2-ethylbutyloxy)-distannoxane. The composition was cooled to approximately 70° C. using a cooler 131, and transferred at a flow rate of approximately 3890 g/hr via a transfer line 7 into an upper portion of a carbon dioxide complex production apparatus 140 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 100 g/hr via a transfer line 9 into a lower portion of the column reactor 240. The reaction temperature in the column reactor 240 was adjusted to approximately 80° C., and a carbon dioxide complex-containing mixture was produced. The carbon dioxide complex-containing mixture obtained was a liquid, and was transferred out at normal pressure at a temperature of 80° C. via a transfer line 10, it being possible to carry out the transfer via the transfer line 10 without problems such as blockage of the transfer line occurring. The mixture was sampled, and subjected to elemental analysis, whereupon the molar ratio between tin atoms, carbon dioxide, and OR groups in the carbon dioxide complex $(Z:(CO_2)_x:(OR)_y)$ was found to be such that x=0.26 and y=1.60.

Example 6

Step A: Production of Tetraalkyldialkoxydistannoxane 1,1,3,3-Tetrabutyl-1,3-di(butyloxy)-distannoxane was produced using the same process as in Example 3.

Step B: Production of Carbon Dioxide Complex-Containing Mixture

A carbon dioxide complex-containing mixture was produced using an apparatus as shown in FIG. 4. The 1,1,3,3-tetrabutyl-1,3-di(butyloxy)-distannoxane produced in step A was supplied at 1200 g/hr from a transfer line 4 into a column reactor 120 of inside diameter 151 mm and effective length 5040 mm packed with a Mellapak 750Y packing (made by Sulzer Chemtech Ltd., Switzerland), and 1-butanol (made by Wako Pure Chemical Industries, Ltd., Japan) that had been purified in a distillation column 110 was supplied at 25000 g/hr from a transfer line 2 into the column reactor 120. The liquid temperature in the reactor was adjusted to 150° C. using a heater and a reboiler 121, and the pressure was adjusted to approximately 160 kPa-G using a pressure regulating valve. The residence time in the reactor was approximately 17 minutes. Approximately 18000 g/hr of water-containing 1-butanol was transferred from an upper portion of the reactor via a transfer line 6, and approximately 283 g/hr of 1-butanol (made by Wako Pure Chemical Industries, Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 1-butanol was transferred out via the transfer line 2 from a lower portion of the distillation column 110. An alkyltin alkoxide composition containing dibutyltin dibutoxide was obtained from a lower portion of the column reactor 120, and was supplied into a thin film evaporator 130 (made by Kobelco Eco-Solutions Co., Ltd., Japan) via a transfer line 5. 1-Butanol was evaporated off using the thin film evaporator 130, and recovered from a transfer line 8 via a condenser 132. The alkyltin alkoxide composition was obtained from a lower portion of the thin film evaporator 130, this composition containing approximately 85 wt % of dibutyltin dibutoxide and approximately 15 wt % of 1-butanol (the 1,1,3,3-tetrabutyl-1,3-di(butyloxy)-distannoxane content was not more than 1 wt %). The composition was cooled to approximately −42° C. using a cooler 131, and transferred at a flow rate of approximately 1666 g/hr via a transfer line 7 into an upper portion of a carbon dioxide complex production apparatus 140. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 280 g/hr via a transfer line 9 into a lower portion of the column reactor 240. The reaction temperature in the column reactor 240 was adjusted to approximately −40° C., and a carbon dioxide complex-containing mixture was produced. The mixture was a liquid, and was transferred out at normal pressure at a temperature of −40° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=1.58 and y=1.99.

Example 7

Figure 5:
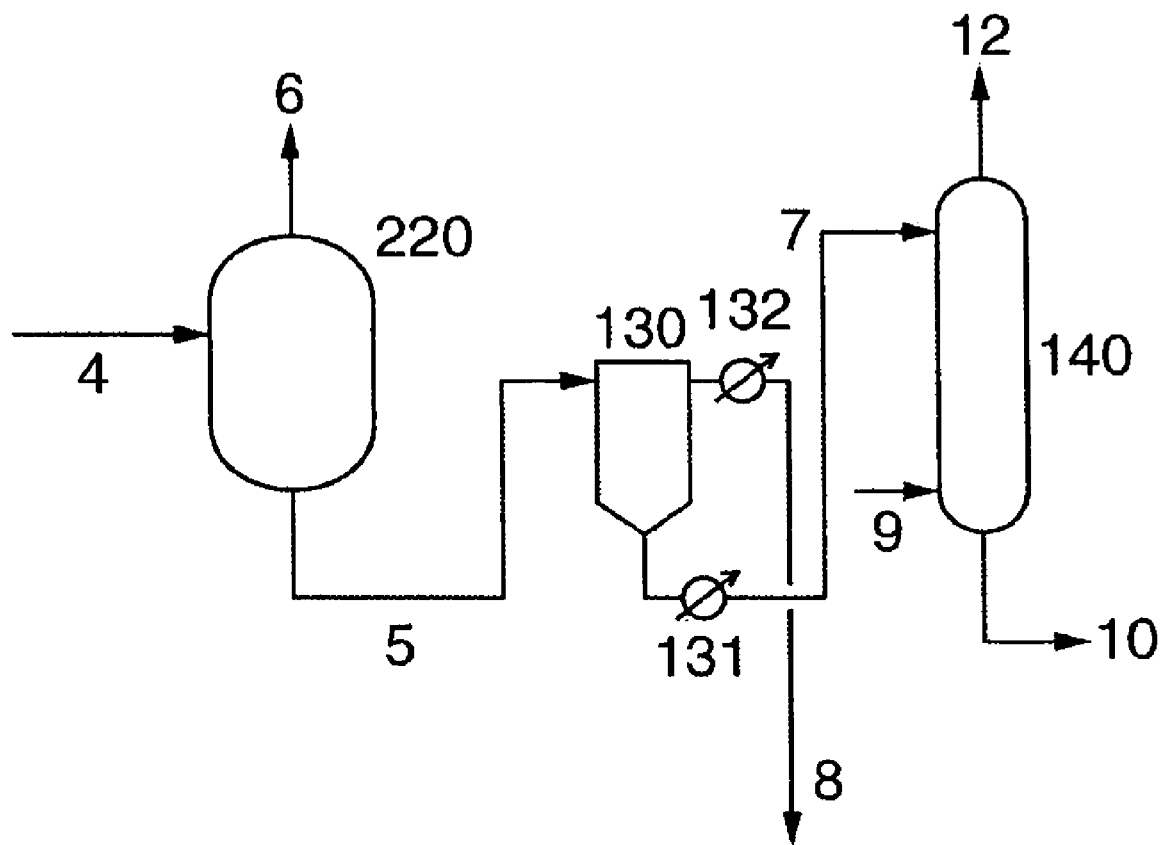
FIG. 5 shows a schematic diagram of an apparatus for producing a mixture containing an alkyltin alkoxide composition and carbon dioxide complex.

A carbon dioxide complex-containing mixture was produced using an apparatus as shown in FIG. 5. Approximately 1000 g of dibutyltin dibutoxide produced using the same process as in Example 6 and approximately 7200 g of benzyl alcohol (made by Aldrich, USA, dehydrated grade) were fed via a transfer line 4 into a tank reactor 220 equipped with a stirrer, and the liquid mixture was heated to approximately 140° C., so as to produce dibutyl-bis(benzyloxy)tin. 1-butanol-containing benzyl alcohol produced from the reaction was recovered from a transfer line 6, and a dibutyl-bis(benzyloxy)tin-containing alkyltin alkoxide composition was transferred via a transfer line 5 into a thin film evaporator 130, where benzyl alcohol was evaporated off, and recovered via a condenser 132 and a transfer line 8. The alkyltin alkoxide composition was obtained from a lower portion of the thin film evaporator 130, this composition containing approximately 99 wt % of dibutyl-bis(benzyloxy)tin. The composition was cooled to approximately 15° C. using a cooler 131, and transferred into an upper portion of a carbon dioxide complex production apparatus 140 at a flow rate of approximately 1180 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 100 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at normal pressure at a temperature of 20° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.75 and y=1.99.

Example 8

A carbon dioxide complex-containing mixture was produced using an apparatus as shown in FIG. 5. Approximately 1000 g of dibutyltin dibutoxide produced using the same process as in Example 6 and approximately 7500 g of 1-heptanol (made by Aldrich, USA, purified by distillation in advance) were fed via a transfer line 4 into a tank reactor 220 equipped with a stirrer, and the liquid mixture was heated to approximately 140° C., so as to produce dibutyl-bis(heptyloxy)tin. 1-Butanol-containing 1-heptanol produced from the reaction was recovered from a transfer line 6, and a dibutyl-bis(heptyloxy)tin-containing alkyltin alkoxide composition was transferred via a transfer line 5 into a thin film evaporator 130, where 1-heptanol was evaporated off, and recovered via a condenser 132 and a transfer line 8. The alkyltin alkoxide composition was obtained from a lower portion of the thin film evaporator 130, this composition containing approximately 99 wt % of dibutyl-bis(heptyloxy)tin. The composition was cooled to approximately 100° C. using a cooler 131, and transferred into an upper portion of a carbon dioxide complex production apparatus 140 at a flow rate of approximately 1230 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 100 g/hr via a transfer line 9 into a lower portion of the column reactor 240. The reaction temperature in the column reactor 240 was adjusted to approximately 100° C., and a carbon dioxide complex-containing mixture was produced. The mixture was a liquid, and was transferred out at normal pressure at a temperature of 100° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.10 and y=1.99.

Example 9

A carbon dioxide complex-containing mixture was produced using an apparatus as shown in FIG. 5. Approximately 1000 g of dibutyltin dimethoxide (made by Aldrich, USA) and approximately 7500 g of 1-propanol (made by Wako Pure Chemical Industries, Ltd., dehydrated grade) were fed via a transfer line 4 into a tank reactor 220 equipped with a stirrer, and the liquid mixture was heated to approximately 100° C., so as to produce dibutyltin dipropoxide. Methanol-containing 1-propanol produced from the reaction was recovered from a transfer line 6, and a dibutyltin dipropoxide-containing alkyltin alkoxide composition was transferred via a transfer line 5 into a thin film evaporator 130, where 1-propanol was evaporated off, and recovered via a condenser 132 and a transfer line 8. The alkyltin alkoxide composition was obtained from a lower portion of the thin film evaporator 130, this composition containing approximately 92 wt % of dibutyltin dipropoxide and approximately 7 wt % of 1,1,3,3-tetrabutyl-1,3-di(propyloxy)-distannoxane. The composition was cooled to approximately 95° C. using a cooler 131, and transferred into an upper portion of a carbon dioxide complex production apparatus 140 at a flow rate of approximately 1175 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 200 g/hr via a transfer line 9 into a lower portion of the column reactor 240. The reaction temperature in the column reactor 240 was adjusted to approximately 100° C., and a carbon dioxide complex-containing mixture was produced. The mixture was a liquid, and was transferred out at normal pressure at a temperature of 100° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture ($Z:(CO_2)_x:(OR)_y$) was found to be such that x=0.25 and y=1.88.

Example 10

A carbon dioxide complex-containing mixture was produced using an apparatus as shown in FIG. 5. Approximately 1000 g of dibutyltin dibutoxide produced using the same process as in Example 6 and approximately 7500 g of 2-ethyl-1-hexanol (made by Aldrich, USA) were fed via a transfer line 4 into a tank reactor 220 equipped with a stirrer, and the liquid mixture was heated to approximately 150° C., so as to produce dibutyl-bis(2-ethylhexyloxy)tin. The pressure in the system was gradually reduced, and 1-butanol-containing 2-ethyl-1-hexanol produced from the reaction was recovered from a transfer line 6. After carrying out reaction for approximately 4 hr, a dibutyl-bis(2-ethylhexyloxy)tin-containing alkyltin alkoxide composition was transferred via a transfer line 5 into a thin film evaporator 130, where 2-ethyl-1-hexanol was evaporated off, and recovered via a condenser 132 and a transfer line 8. The alkyltin alkoxide composition was obtained from a lower portion of the thin film evaporator 130, this composition containing approximately 95 wt % of dibutyl-bis(2-ethylhexyloxy)tin. The composition was cooled to approximately 10° C. using a cooler 131, and transferred into an upper portion of a carbon dioxide complex production apparatus 140 at a flow rate of approximately 1297 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of 0.4 MPa-G at approximately 150 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at a temperature of 20° C. and a pressure of 0.4 MPa-G via a transfer line 10, but because of high viscosity of the mixture, the pressure increase was high and as the result the transfer was difficult. The mixture was sampled, and subjected to elemental analysis, whereupon the molar ratio between tin atoms, carbon dioxide, and OR groups in the mixture ($Z:(CO_2)_x:(OR)_y$) was found to be such that x=1.18 and y=1.99.

Example 11

Step A: Production of Tetraalkyldialkoxydistannoxane

The same procedure as in Example 4 was carried out, so as to produce 1,1,3,3-tetraoctyl-1,3-bis(3-methylbutyloxy)-distannoxane to be used in the following step B.

Step B: Production of Carbon Dioxide Complex-Containing Mixture

Figure 15:
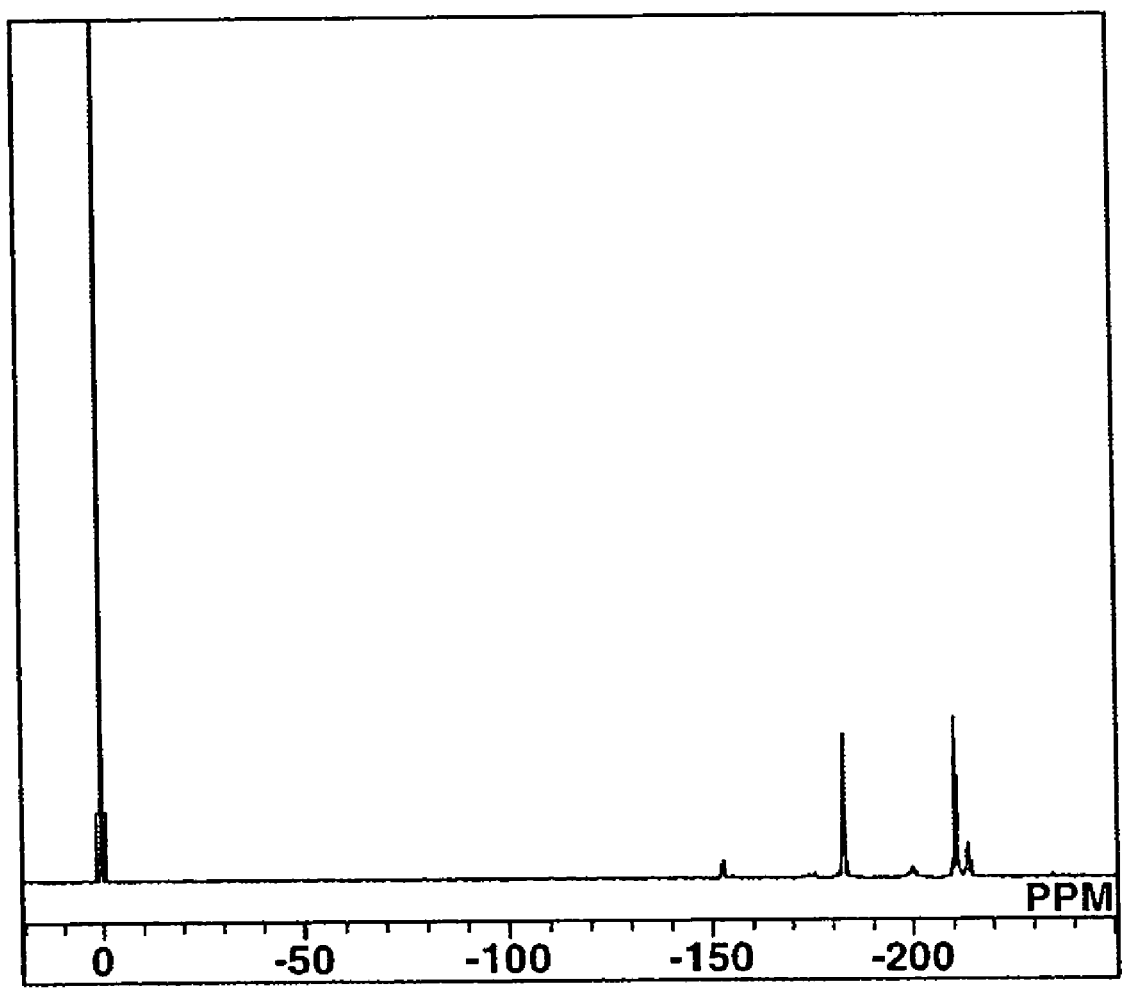
FIG. 15 shows a $^{119}$Sn-NMR spectrum of a carbon dioxide complex-containing mixture.

A carbon dioxide complex-containing mixture was produced using an apparatus as shown in FIG. 4. The 1,1,3,3-tetraoctyl-1,3-bis(3-methylbutyloxy)-distannoxane produced in step A was supplied at 1200 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 240 g/hr from a transfer line 2 into the column reactor 120. The liquid temperature in the reactor was adjusted to 140° C. using a heater and a reboiler 121, and the pressure was adjusted to approximately 24 kPa-G using a pressure regulating valve. The residence time in the reactor was approximately 17 minutes. Approximately 180 g/hr of water-containing 3-methyl-1-butanol was transferred from an upper portion of the reactor via a transfer line 6, and approximately 14 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 20 mol % of dioctyl-bis(3-methylbutyloxy)tin and approximately 80 mol % of 1,1,3,3-tetraoctyl-1,3-bis(3-methylbutyloxy)-distannoxane. The composition was cooled to approximately 15° C. using a cooler 131, and transferred into an upper portion of a carbon dioxide complex production apparatus 140 at a flow rate of approximately 1225 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of 0.4 MPa-G at approximately 100 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at a temperature of 20° C. and a pressure of 0.4 MPa-G via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.77 and y=1.11. NMR analysis results are shown in FIG. 15 ($^{119}$Sn-NMR).

Example 12

Step A: Production of Tetraalkyldialkoxydistannoxane

The same procedure as in Example 4 was carried out, so as to produce 1,1,3,3-tetraoctyl-1,3-bis(3-methylbutyloxy)-distannoxane to be used in the following step B.

Step B: Production of Carbon Dioxide Complex-Containing Mixture

A carbon dioxide complex-containing mixture was produced using an apparatus as shown in FIG. 7. The 1,1,3,3-tetraoctyl-1,3-bis(3-methylbutyloxy)-distannoxane produced in step A (temperature approximately 15° C.) was transferred via a transfer line 7 into an upper portion of a carbon dioxide complex production apparatus 240 at a flow rate of approximately 1200 g/hr. The carbon dioxide complex production apparatus 240 was a column reactor of inside diameter 53.5 mm and effective length 2680 mm (packed length approximately 2000 mm) packed with a Dixon packing (made by Tokyo Tokushu Kanaami, Japan, size 6 mm) and equipped with a cooling jacket. Gaseous carbon dioxide (made by Showa Tansan Co., Ltd., Japan, purity 99.99%, water content not more than 40 ppm) was supplied at a pressure of 0.4 MPa-G at approximately 100 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at a temperature of 20° C. and a pressure of 0.4 MPa-G via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.56 and y=0.98.

Example 13

Step A: Production of Tetraalkyldialkoxydistannoxane 700 g (1.94 mol) of dioctyltin oxide (made by Sankyo Organic Chemicals Co., Ltd., Japan) and 1600 g (15.7 mol) of 2-ethyl-1-butanol (made by Chisso Corporation, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 157° C., and the flask was immersed in the oil bath and rotation of the evaporator was commenced. With the purge valve of the evaporator left open, rotational stirring and heating were carried out for approximately 40 minutes at normal pressure, and then the purge valve was closed, and the pressure in the system was gradually reduced, and water-containing 2-ethyl-1-butanol was distilled off with the pressure in the system at from 84 to 65 kPa. This state was maintained for 7 hours, and then the pressure in the system was further reduced, and excess 2-ethyl-1-butanol was distilled off. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 883 g of reaction liquid was obtained in the flask. According to $^{119}$Sn—, $^1$H—, and $^{13}$C-NMR analysis results, the product 1,1,3,3-tetraoctyl-1,3-bis(2-ethylbutyloxy)-distannoxane was obtained at a yield of 99% based on the dioctyltin oxide. The same procedure was carried out so as to produce 1,1,3,3-tetraoctyl-1,3-bis(2-ethylbutyloxy)-distannoxane to be used in the following step B.

Step B: Production of Carbon Dioxide Complex-Containing Mixture

Figure 9:
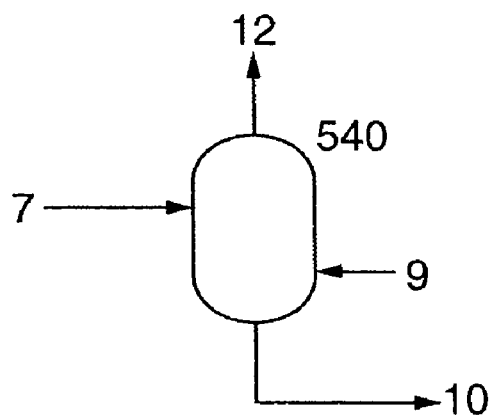
FIG. 9 shows a schematic diagram of an apparatus for producing a carbon dioxide complex-containing mixture.

A carbon dioxide complex-containing mixture was produced using an apparatus as shown in FIG. 9. Approximately 1200 g of the 1,1,3,3-tetraoctyl-1,3-bis(2-ethylbutyloxy)-distannoxane produced in step A was transferred via a transfer line 7 into an upper portion of an autoclave 540 equipped with a heat exchange jacket and a stirrer. The autoclave was cooled to approximately 0° C., whereupon the 1,1,3,3-tetraoctyl-1,3-bis(2-ethylbutyloxy)-distannoxane became a solid. Gaseous carbon dioxide (made by Showa Tansan Co., Ltd., Japan, purity 99.99%, water content not more than 40 ppm) was supplied via a transfer line 9 into the autoclave 540, and the pressure was adjusted to 0.4 MPa-G, whereby a carbon dioxide complex-containing mixture was produced. The mixture was a mixture of a liquid and a solid, and hence transfer was difficult due to blockage of the line. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.23 and y=0.98.

Example 14

Step A: Production of Alkyltin Alkoxide Composition

The same procedure as in Example 18 was carried out, so as to produce dibutyl-bis(3-methylbutyloxy)-tin and 1,1,3,3-tetrabutyl-1,3-bis(3-methylbutyloxy)-distannoxane to be used in the following step B.

Step B: Production of Carbon Dioxide Complex-Containing Mixture

A carbon dioxide complex-containing mixture was produced using an apparatus as shown in FIG. 9. A liquid mixture comprising approximately 1200 g of the alkyltin alkoxide composition produced in step A (approximately 74 wt % of dibutyl-bis(3-methylbutyloxy)-tin and approximately 25 wt % of 1,1,3,3-tetrabutyl-1,3-bis(3-methylbutyloxy)-distannoxane) and approximately 18.5 g of bis(3-methylbutyl) carbonate produced as in Example 18 was transferred via a transfer line 7 into an upper portion of an autoclave 540 equipped with a heat exchange jacket and a stirrer. The autoclave was set to approximately 80° C., and gaseous carbon dioxide (made by Showa Tansan Co., Ltd., Japan, purity 99.99%, water content not more than 40 ppm) was further supplied via a transfer line 9 into the autoclave, and the internal pressure was adjusted to 0.01 MPa-G, whereby a carbon dioxide complex-containing mixture was produced. The mixture was a liquid, and was transferred out via a transfer line 10 at a temperature of 80° C. and a pressure of 0.01 MPa-G, but because of the generation of gas in the transfer line, the pump cavitation occurred and as the result the transfer was difficult. The mixture was sampled, and subjected to elemental analysis, whereupon the molar ratio between tin atoms, carbon dioxide, and OR groups in the mixture (Z:$(CO_2)_x$:$(OR)_y$) was found to be such that x=1.07 and y=1.98.

Example 15

Step A: Production of Tetraalkyldialkoxydistannoxane

The same procedure as in Example 4 was carried out, so as to produce 1,1,3,3-tetraoctyl-1,3-bis(3-methylbutyloxy)-distannoxane to be used in the following step B.

Step B: Production of Carbon Dioxide Complex-Containing Mixture

A carbon dioxide complex-containing mixture was produced using an apparatus as shown in FIG. 4. The 1,1,3,3-tetraoctyl-1,3-bis(3-methylbutyloxy)-distannoxane produced in step A was supplied at 1200 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 24000 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 20000 g/hr of water-containing 3-methyl-1-butanol was transferred from an upper portion of the reactor via a transfer line 6, and approximately 240 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 99 wt % of dioctyl-bis(3-methylbutyloxy)tin. The composition was cooled to approximately 100° C. using a cooler 131, and transferred into an upper portion of a carbon dioxide complex production apparatus 140 at a flow rate of approximately 1430 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of 0.1 MPa-G at approximately 130 g/hr via a transfer line 9 into a lower portion of the column reactor 240. The reaction temperature in the column reactor 240 was adjusted to approximately 100° C., and a carbon dioxide complex-containing mixture was produced. The mixture was a liquid, and was transferred out at a temperature of 100° C. and a pressure of 0.1 MPa-G via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.23 and y=1.99.

Example 16

Step A: Production of Tetraalkyldialkoxydistannoxane

The same procedure as in Example 4 was carried out, so as to produce 1,1,3,3-tetraoctyl-1,3-bis(3-methylbutyloxy)-distannoxane to be used in the following step B.

Step B: Production of Carbon Dioxide Complex-Containing Mixture

A carbon dioxide complex-containing mixture was produced using an apparatus as shown in FIG. 4. The 1,1,3,3-tetraoctyl-1,3-bis(3-methylbutyloxy)-distannoxane produced in step A was supplied at 1200 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 24000 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 20000 g/hr of water-containing 3-methyl-1-butanol was transferred from an upper portion of the reactor via a transfer line 6, and approximately 240 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 90 wt % of dioctyl-bis(3-methylbutyloxy)tin and approximately 10 wt % of 3-methyl-1-butanol (the 1,1,3,3-tetraoctyl-1,3-bis(3-methylbutyloxy)-distannoxane content was not more than 1 wt %). The composition was cooled to approximately −60° C. using a cooler 131, and transferred into an upper portion of a carbon dioxide complex production apparatus 140 at a flow rate of approximately 1410 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of 0.1 MPa-G at approximately 130 g/hr via a transfer line 9 into a lower portion of the column reactor 240. The reaction temperature in the column reactor 240 was adjusted to approximately −60° C., and a carbon dioxide complex-containing mixture was produced. The mixture was transferred out at a temperature of −60° C. and a pressure of 0.1 MPa-G via a transfer line 10, but because of high viscosity of the mixture, the pressure increase was high and as the result the transfer was difficult. The mixture was sampled, and subjected to elemental analysis, whereupon the molar ratio between tin atoms, carbon dioxide, and OR groups in the mixture (Z:$(CO_2)_x$:$(OR)_y$) was found to be such that x=1.8 and y=1.99.

Example 17

Step A: Production of Tetraalkyldialkoxydistannoxane

The same procedure as in Example 4 was carried out, so as to produce 1,1,3,3-tetraoctyl-1,3-bis(3-methylbutyloxy)-distannoxane to be used in the following step B.

Step B: Production of Carbon Dioxide Complex-Containing Mixture

A carbon dioxide complex-containing mixture was produced using an apparatus as shown in FIG. 9. A liquid mixture comprising approximately 1200 g of the 1,1,3,3-tetraoctyl-1,3-bis(3-methylbutyloxy)-distannoxane produced in step A and approximately 270 g of bis(3-methylbutyl) carbonate produced as in Example 18 was transferred via a transfer line 7 into an upper portion of an autoclave 540 equipped with a heat exchange jacket and a stirrer. The autoclave was set to approximately 140° C., the reaction time was made to be approximately 5 hr, and a carbon dioxide complex-containing mixture was produced. After the reaction, the autoclave was cooled, thus making the temperature of the mixture be approximately 20° C. The mixture was a liquid, and was transferred out at normal pressure at a temperature of 20° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.49 and y=1.98.

Comparative Example 1

A carbon dioxide complex-containing mixture was produced using an apparatus as shown in FIG. 5. Approximately 1000 g of dibutyltin dibutoxide produced using the same process as in Example 6 and approximately 7500 g of phenol (made by Wako Pure Chemical Industries, Ltd., Japan, purified by distillation in advance) were fed via a transfer line 4 into a tank reactor 220 equipped with a stirrer, and the liquid mixture was heated to approximately 140° C., so as to produce dibutyltin diphenoxide. 1-Butanol-containing phenol produced from the reaction was distilled off, and recovered from a transfer line 6, and a dibutyltin diphenoxide-containing alkyltin alkoxide composition was transferred via a transfer line 5 into a thin film evaporator 130, where phenol was evaporated off, and recovered via a condenser 132 and a transfer line 8. The alkyltin alkoxide composition was obtained from a lower portion of the thin film evaporator 130, this composition containing approximately 99 wt % of dibutyltin diphenoxide. The composition was cooled to approximately 60° C. using a cooler 131, and transferred into an upper portion of a carbon dioxide complex production apparatus 140 at a flow rate of approximately 1107 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 100 g/hr via a transfer line 9 into a lower portion of the column reactor 240. The reaction temperature in the column reactor 240 was adjusted to approximately 60° C., and a carbon dioxide complex-containing mixture was produced. The mixture was a liquid, and was transferred out at normal pressure at a temperature of 60° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.02 and y=1.99.

Comparative Example 2

A carbon dioxide complex-containing mixture was produced using an apparatus as shown in FIG. 5. Approximately 1000 g of dibutyltin dibutoxide produced using the same process as in Example 6 and approximately 7500 g of 1-ethoxy-2-propanol (made by Wako Pure Chemical Industries, Ltd., Japan, purified by distillation to remove a primary alcohol impurity) were fed via a transfer line 4 into a tank reactor 220 equipped with a stirrer, and the liquid mixture was heated to approximately 140° C., so as to produce dibutyl-bis(1-ethoxy-propyl-2-oxy)tin. 1-butanol-containing 1-ethoxy-2-propanol produced from the reaction was distilled off, and recovered from a transfer line 6, and a dibutyl-bis(1-ethoxypropyl-2-oxy)tin-containing alkyltin alkoxide composition was transferred via a transfer line 5 into a thin film evaporator 130, where 1-ethoxy-2-propanol was evaporated off, and recovered via a condenser 132 and a transfer line 8. The alkyltin alkoxide composition was obtained from a lower portion of the thin film evaporator 130, this composition containing approximately 99 wt % of dibutyl-bis(1-ethoxy-propyl-2-oxy)tin. The composition was cooled to approximately 50° C. using a cooler 131, and transferred into an upper portion of a carbon dioxide complex production apparatus 140 at a flow rate of approximately 1160 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 100 g/hr via a transfer line 9 into a lower portion of the column reactor 240. The reaction temperature in the column reactor 240 was adjusted to approximately 50° C., and a carbon dioxide complex-containing mixture was produced. The mixture was a liquid, and was transferred out at normal pressure at a temperature of 50° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture $(Z:(CO_2)_x:(OR)_y)$ was found to be such that x=0.04 and y=1.99.

Comparative Example 3

A carbon dioxide complex-containing mixture was produced using an apparatus as shown in FIG. 5. Approximately 1000 g of an alkyltin alkoxide composition produced using the same process as in Example 3 (approximately 90 mol % of dibutyltin dibutoxide and approximately 10 mol % of 1,1,3,3-tetrabutyl-1,3-di(butyloxy)-distannoxane) and approximately 7000 g of 1-ethoxy-2-propanol (made by Wako Pure Chemical Industries, Ltd., Japan, purified by distillation to remove a primary alcohol impurity) were fed via a transfer line 4 into a tank reactor 220 equipped with a stirrer, and the liquid mixture was heated to approximately 140° C., so as to produce dibutyl-bis(1-ethoxy-propyl-2-oxy)tin. Water- and 1-butanol-containing 1-ethoxy-2-propanol produced from the reaction was distilled off, and recovered from a transfer line 6, and a dibutyl-bis(1-ethoxy-propyl-2-oxy)tin-containing alkyltin alkoxide composition was transferred via a transfer line 5 into a thin film evaporator 130, where 1-ethoxy-2-propanol was evaporated off, and recovered via a condenser 132 and a transfer line 8. The alkyltin alkoxide composition was obtained from a lower portion of the thin film evaporator 130, this composition containing approximately 98 mol % of dibutyl-bis(1-ethoxy-propyl-2-oxy)tin and approximately 2 mol % of 1,1,3,3-tetrabutyl-1,3-bis(1-ethoxy-propyl-2-oxy)-distannoxane. The composition was cooled to approximately 60° C. using a cooler 131, and transferred into an upper portion of a carbon dioxide complex production apparatus 140 at a flow rate of approximately 1160 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 100 g/hr via a transfer line 9 into a lower portion of the column reactor 240. The reaction temperature in the column reactor 240 was adjusted to approximately 70° C., and a carbon dioxide complex-containing mixture was produced. The mixture was a liquid, and was transferred out at normal pressure at a temperature of 50° C. via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture $(Z:(CO_2)_x:(OR)_y)$ was found to be such that x=0.06 and y=1.94.

Comparative Example 4

Step A: Production of Tetraalkyldialkoxydistannoxane

The same procedure as in Example 1 was carried out, so as to produce 1,1,3,3-tetrabutyl-1,3-bis(3-methylbutyloxy)-distannoxane to be used in the following step B.

Step B: Production of Carbon Dioxide Complex-Containing Mixture

A carbon dioxide complex-containing mixture was produced using an apparatus as shown in FIG. 4. The 1,1,3,3-tetrabutyl-1,3-bis(3-methylbutyloxy)-distannoxane produced in step A was supplied at 1200 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 23000 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 20000 g/hr of water-containing 3-methyl-1-butanol was transferred from an upper portion of the reactor via a transfer line 6, and approximately 322 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 99 wt % of dibutyl-bis(3-methylbutyloxy)tin. The composition was cooled to approximately 80° C. using a cooler 131, and transferred into an upper portion of a carbon dioxide complex production apparatus 140 at a flow rate of approximately 1490 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of approximately 13 kPa at approximately 90 g/hr via a transfer line 9 into a lower portion of the column reactor 240. The reaction temperature in the column reactor 240 was adjusted to approximately 80° C., and a carbon dioxide complex-containing mixture was produced. The mixture was a liquid, and was transferred out at a temperature of 80° C. and a pressure of approximately 13 kPa via a transfer line 10, but cavitation occurred and hence continuous transfer could not be carried out. The mixture was sampled, and subjected to elemental analysis, whereupon the molar ratio between tin atoms, carbon dioxide, and OR groups in the mixture (Z: $(CO_2)_x$:$(OR)_y$) was found to be such that x=0.08 and y=1.99.

Example 18

Step A: Production of Tetraalkyldialkoxydistannoxane 672 g (2.7 mol) of dibutyltin oxide (made by Sankyo Organic Chemicals Co., Ltd., Japan) and 1900 g (21.5 mol) of 3-methyl-1-butanol (made by Kuraray Co., Ltd., Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to approximately 145° C., and the flask was immersed in the oil bath and rotation of the evaporator was commenced. With the purge valve of the evaporator left open, rotational stirring and heating were carried out for approximately 40 minutes at normal pressure, whereupon the liquid mixture boiled, and hence distilling off of water-containing 3-methyl-1-butanol began. This state was maintained for 7 hours, and then the purge valve was closed, and the pressure in the system was gradually reduced, and excess 3-methyl-1-butanol was distilled off with the pressure in the system at from 74 to 35 kPa. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 880 g of reaction liquid was obtained in the flask. According to $^{119}$Sn—, $^1$H—, and $^{13}$C-NMR analysis results, the product 1,1,3,3-tetrabutyl-1,3-bis(3-methylbutyloxy)-distannoxane was obtained at a yield of 99% based on the dibutyltin oxide. The same procedure was carried out so as to produce 1,1,3,3-tetrabutyl-1,3-bis(3-methylbutyloxy)-distannoxane to be used in the following step B.

Step B: Production of Carbonate Using Continuous Production Apparatus

Figure 6:
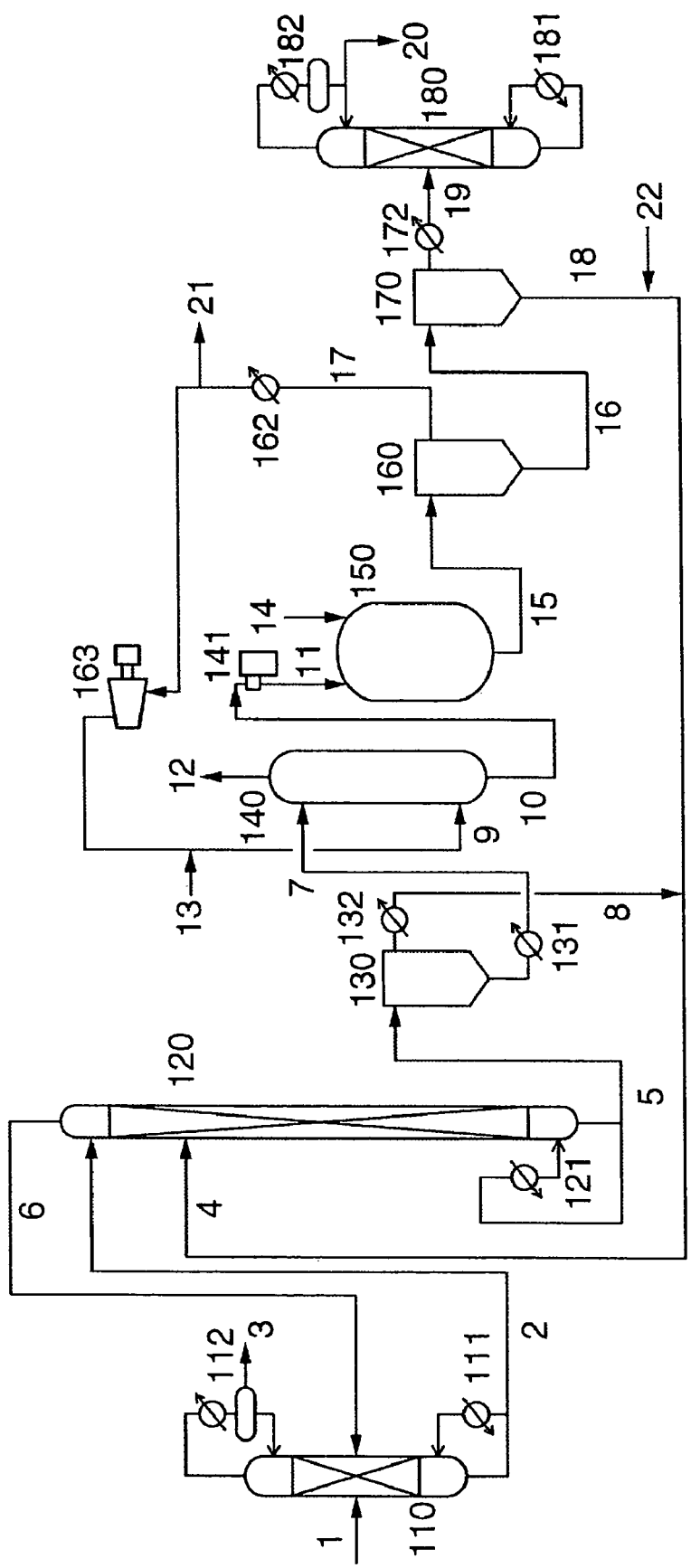
FIG. 6 shows a schematic diagram of a carbonate production apparatus including a step of producing a carbon dioxide complex-containing mixture.

A carbonate was produced using a continuous production apparatus as shown in FIG. 6. A liquid mixture of the 1,1,3,3-tetrabutyl-1,3-bis(3-methylbutyloxy)-distannoxane produced in step A and 3-methyl-1-butanol (distannoxane concentration approximately 33 wt %) was supplied at approximately 13384 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14953 g/hr from a transfer line 2 into the column reactor 120. The liquid temperature in the reactor was adjusted to 140° C. using a heater and a reboiler 121, and the pressure was adjusted to approximately 23 kPa-G using a pressure regulating valve. The residence time in the reactor was approximately 17 minutes. Approximately 14950 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed, with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 50° C. using a cooler 131, and transferred into an upper portion of a carbon dioxide complex production apparatus 140 at a flow rate of approximately 5130 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.45 MPa-G. The reaction temperature in the column reactor 240 was adjusted to 60° C., and carbon dioxide complex was produced. The carbon dioxide complex obtained was a liquid, and could be transferred out via a transfer line 10 without problems such as blockage of the line occurring. Furthermore, flow of gas through a vent line 12 was not seen, the supplied carbon dioxide and the alkyltin alkoxides being converted into a carbon dioxide complex-containing mixture. The mixture was sampled, and subjected to elemental analysis, whereupon the molar ratio between tin atoms, carbon dioxide, and OR groups in the mixture (Z: $(CO_2)_x$:$(OR)_y$) was found to be such that x=1.31 and y=1.72. The mixture was transferred via the transfer line 10 at a temperature of 50° C. and a pressure of 0.5 MPa-G, and further supplied using a booster pump 141 via a transfer line 11 at a flow rate of approximately 5894 g/hr into an autoclave 150 equipped with a stirrer. Carbon dioxide (made by Showa Tansan Co., Ltd., Japan, purity 99.99%, water content not more than 40 ppm) was supplied at approximately 210 g/hr via a supply line 14 into the autoclave, the pressure in the autoclave being maintained at 4 MPa-G. The temperature in the autoclave was set to 120° C., and the residence time was adjusted to approximately 5 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off, and recovered from a transfer line 17. After that, the separated bis(3-methylbutyl) carbonate-containing reaction liquid was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The bis(3-methylbutyl) carbonate-containing distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20.

Example 19

1,1,3,3-Tetrabutyl-1,3-bis(3-methylbutyloxy)-distannoxane was produced using the same process as in step A of Example 18, and then a carbonate was produced in the following step.

A carbonate was produced using a continuous production apparatus as shown in FIG. 6. A liquid mixture of the 1,1,3,3-tetrabutyl-1,3-bis(3-methylbutyloxy)-distannoxane and 3-methyl-1-butanol (distannoxane concentration approximately 33 wt %) was supplied at approximately 13384 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14953 g/hr from a transfer line 2 into the column reactor 120. The liquid temperature in the reactor was adjusted to 140° C. using a heater and a reboiler 121, and the pressure was adjusted to approximately 22 kPa-G using a pressure regulating valve. The residence time in the reactor was approximately 17 minutes. Approximately 14950 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 50° C. using a cooler 131, and transferred into an upper portion of a carbon dioxide complex production apparatus 140 at a flow rate of approximately 5130 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.45 MPa-G The reaction temperature in the column reactor 240 was adjusted to 60° C., and carbon dioxide complex was produced. The carbon dioxide complex obtained was a liquid, and could be transferred out via a transfer line 10 without problems such as blockage of the line occurring. Furthermore, flow of gas through a vent line 12 was not seen, the supplied carbon dioxide and the alkyltin alkoxides being converted into a carbon dioxide complex-containing mixture. The mixture was supplied via the transfer line 10 at a flow rate of approximately 5894 g/hr into an autoclave 150 equipped with a stirrer. Carbon dioxide was supplied at approximately 210 g/hr via a supply line 14 into the autoclave, the pressure in the autoclave being maintained at 4 MPa-G. The temperature in the autoclave was set to 120° C., and the residence time was adjusted to approximately 5 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9. At the same time, the amount of carbon dioxide supplied in from the supply line 13 was gradually reduced, and in a steady state the supply of the carbon dioxide from the supply line 13 was stopped, and the unused carbon dioxide was transferred out from the transfer line 17 at approximately 764 g/hr. The carbon dioxide complex-containing mixture obtained was a liquid as in Example 18, and could be transferred out via the transfer line 10 at a temperature of 50° C. and a pressure of 0.5 MPa-G without problems such as blockage of the transfer line occurring. Furthermore, flow of gas through the vent line 12 was not seen, the recycled unused carbon dioxide being recovered in the form of the carbon dioxide complex-containing mixture. The mixture was sampled, and subjected to elemental analysis, whereupon the molar ratio between tin atoms, carbon dioxide, and OR groups in the mixture $(Z:(CO_2)_x:(OR)_y)$ was found to be such that $x=1.32$ and $y=1.72$.

Example 20

1,1,3,3-Tetrabutyl-1,3-bis(3-methylbutyloxy)-distannoxane was produced using the same process as in step A of Example 18, and then a carbonate was produced in the following step.

A carbonate was produced using a continuous production apparatus as shown in FIG. 6. A liquid mixture of the 1,1,3,3-tetrabutyl-1,3-bis(3-methylbutyloxy)-distannoxane and 3-methyl-1-butanol (distannoxane concentration approximately 33 wt %) was supplied at approximately 13384 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14953 g/hr from a transfer line 2 into the column reactor 120. The liquid temperature in the reactor was adjusted to 140° C. using a heater and a reboiler 121, and the pressure was adjusted to approximately 23 kPa-G using a pressure regulating valve. The residence time in the reactor was approximately 17 minutes. Approximately 14950 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 50° C. using a cooler 131, and transferred into an upper portion of a carbon dioxide complex production apparatus 140 at a flow rate of approximately 5130 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 into a lower portion of the column reactor 240. The pressure in the column was adjusted to 0.45 MPa-G The reaction temperature in the column reactor 240 was adjusted to 60° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into the carbon dioxide complex-containing mixture. The mixture was supplied via the transfer line 10 at a flow rate of approximately 5894 g/hr into an autoclave 150 equipped with a stirrer. Carbon dioxide (made by Showa Tansan Co., Ltd., Japan, purity 99.99%, water content not more than 40 ppm) was supplied at approximately 212 g/hr via a supply line 14 into the autoclave, the pressure in the autoclave being maintained at 4 MPa-G. The temperature in the autoclave was set to 120° C., and the residence time was adjusted to approximately 5 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid as in Example 18, and was transferred out via the transfer line 10 at a temperature of 60° C. and a pressure of 0.45 MPa-G, it being possible to carry out the transfer without problems such as blockage of the transfer line occurring. Furthermore, flow of gas through the vent line 12 was not seen, the recycled unused carbon dioxide being recovered in the form of the carbon dioxide complex-containing mixture. The mixture was sampled, and subjected to elemental analysis, whereupon the molar ratio between tin atoms, carbon dioxide, and OR groups in the mixture $(Z:(CO_2)_x:(OR)_y)$ was found to be such that $x=1.33$ and $y=1.71$.

The bis(3-methylbutyl) carbonate-containing reaction liquid separated out by the thin film evaporator 160 was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20. The amount of carbon dioxide consumed in the carbonate production was 210 g/hr based on 212 g/hr of supplied carbon dioxide, and hence the carbon dioxide usage ratio was 99%, i.e. a high carbon dioxide usage ratio could be obtained through the recycling of the carbon dioxide separated out by the thin film evaporator 160.

Example 21

Step A: Production of Tetraalkyldialkoxydistannoxane 700 g (1.94 mol) of dioctyltin oxide (made by Sankyo Organic Chemicals Co., Ltd., Japan) and 1700 g (19.3 mol) of 3-methyl-1-butanol (made by Kuraray Co., Ltd., Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 143° C., and the flask was immersed in the oil bath and rotation of the evaporator was commenced. With the purge valve of the evaporator left open, rotational stirring and heating were carried out for approximately 40 minutes at normal pressure, whereupon the liquid mixture boiled, and hence distilling off of a low boiling component began. This state was maintained for 7 hours, and then the purge valve was closed, and the pressure in the system was gradually reduced, and residual low boiling component was distilled off with the pressure in the system at from 76 to 32 kPa. Once low boiling component stopped coming off, the flask was lifted out from the oil bath. The reaction liquid was a transparent liquid. After lifting the flask out from the oil bath, the purge valve was gradually opened, so as to return the pressure in the system to normal pressure. 864 g of reaction liquid was obtained in the flask. According to $^{119}$Sn—, $^{1}$H—, and $^{13}$C-NMR analysis results, the product 1,1,3,3-tetraoctyl-1,3-bis(3-methylbutyloxy)-distannoxane was obtained at a yield of 99% based on the dioctyltin oxide. The same procedure was carried out so as to produce 1,1,3,3-tetraoctyl-1,3-bis(3-methylbutyloxy)-distannoxane to be used in the following step B.

Step B: Production of Carbonate Using Continuous Production Apparatus

A carbonate was produced using a continuous production apparatus as shown in FIG. 6. A liquid mixture of the 1,1,3,3-tetraoctyl-1,3-bis(3-methylbutyloxy)-distannoxane and 3-methyl-1-butanol (distannoxane concentration approximately 40 wt %) was supplied at approximately 14883 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14953 g/hr from a transfer line 2 into the column reactor 120. The liquid temperature in the reactor was adjusted to 140° C. using a heater and a reboiler 121, and the pressure was adjusted to approximately 23 kPa-G using a pressure regulating valve. The residence time in the reactor was approximately 17 minutes. Approximately 14950 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 73 wt % of dioctyl-bis(3-methylbutyloxy)tin and approximately 26 wt % of 1,1,3,3-tetraoctyl-1,3-bis(3-methylbutyloxy)-distannoxane. The composition was cooled to approximately 50° C. using a cooler 131, and transferred into an upper portion of a carbon dioxide complex production apparatus 140 at a flow rate of approximately 6630 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.45 MPa-G. The reaction temperature in the column reactor 240 was adjusted to 60° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into the carbon dioxide complex-containing mixture. The carbon dioxide complex was transferred via the transfer line 10 at a temperature of 60° C. and a pressure of 0.45 MPa-G, and further supplied using a booster pump 141 via a transfer line 11 at a flow rate of approximately 7394 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 6 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex $(Z:(CO_2)_x:(OR)_y)$ was found to be such that x=1.33 and y=1.71.

The bis(3-methylbutyl) carbonate-containing reaction liquid separated out by the thin film evaporator 160 was transferred via a transfer line 16 with the flow rate adjusted to approximately 6840 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20.

Example 22

Step A: Production of Tetraalkyldialkoxydistannoxane 1,1,3,3-Tetraoctyl-1,3-bis(3-methylbutyloxy)-distannoxane was produced using the same process as in step A of Example 21, and then a carbonate was produced in the following step.

Step B: Production of Carbonate Using Continuous Production Apparatus

A carbonate was produced using a continuous production apparatus as shown in FIG. 6. A liquid mixture of the 1,1,3,3-tetraoctyl-1,3-bis(3-methylbutyloxy)-distannoxane and 3-methyl-1-butanol (distannoxane concentration approximately 40 wt %) was supplied at approximately 14883 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14953 g/hr from a transfer line 2 into the column reactor 120. The liquid temperature in the reactor was adjusted to 140° C. using a heater and a reboiler 121, and the pressure was adjusted to approximately 23 kPa-G using a pressure regulating valve. The residence time in the reactor was approximately 17 minutes. Approximately 14950 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 73 wt % of dioctyl-bis(3-methylbutyloxy)tin and approximately 26 wt % of 1,1,3,3-tetraoctyl-1,3-bis(3-methylbutyloxy)-distannoxane. The composition was cooled to approximately 70° C. using a cooler 131, and transferred at a flow rate of approximately 6630 g/hr via a transfer line 7 into an upper portion of a carbon dioxide complex production apparatus 140 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 1.0 MPa-G. The reaction temperature in the column reactor 240 was adjusted to 80° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into the carbon dioxide complex-containing mixture. The carbon dioxide complex was transferred via the transfer line 10 at a temperature of 80° C. and a pressure of 1.0 MPa-G, and further supplied using a booster pump 141 via a transfer line 11 at a flow rate of approximately 7394 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 6 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex $(Z:(CO_2)_x:(OR)_y)$ was found to be such that x=1.33 and y=1.71.

The bis(3-methylbutyl) carbonate-containing reaction liquid separated out by the thin film evaporator 160 was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20.

Example 23

Step A: Production of Tetraalkyldialkoxydistannoxane 692 g (2.78 mol) of dibutyltin oxide (made by Sankyo Organic Chemicals Co., Ltd., Japan) and 2000 g (27 mol) of 1-butanol (made by Wako, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 126° C., and the flask was immersed in the oil bath and rotation of the evaporator was commenced. With the purge valve of the evaporator left open, rotational stirring and heating were carried out for approximately 30 minutes at normal pressure, whereupon the liquid mixture boiled, and hence distilling off of a low boiling component began. This state was maintained for 8 hours, and then the purge valve was closed, and the pressure in the system was gradually reduced, and residual low boiling component was distilled off with the pressure in the system at from 76 to 54 kPa. Once low boiling component stopped coming off, the flask was lifted out from the oil bath. The reaction liquid was a transparent liquid. After lifting the flask out from the oil bath, the purge valve was gradually opened, so as to return the pressure in the system to normal pressure. 952 g of reaction liquid was obtained in the flask. According to $^{119}$Sn—, $^1$H—, and $^{13}$C-NMR analysis results, the product 1,1,3,3-tetrabutyl-1,3-di(butyloxy)-distannoxane was obtained at a yield of 99% based on the dibutyltin oxide. The same procedure was carried out so as to produce 1,1,3,3-tetrabutyl-1,3-di(butyloxy)-distannoxane to be used in the following step B.

Step B: Production of Carbonate Using Continuous Production Apparatus

A carbonate was produced using a continuous production apparatus as shown in FIG. 6. A liquid mixture of the 1,1,3,3-tetrabutyl-1,3-di(butyloxy)-distannoxane and 1-butanol (distannoxane concentration approximately 22 wt %) was supplied at approximately 19350 g/hr from a transfer line 4 into a column reactor 120 of inside diameter 151 mm and effective length 5040 mm packed with a Mellapak 750Y packing (made by Sulzer Chemtech Ltd., Switzerland), and 1-butanol (made by Wako Pure Chemical Industries, Ltd., Japan) that had been purified in a distillation column 110 was supplied at 24716 g/hr from a transfer line 2 into the column reactor 120. The liquid temperature in the reactor was adjusted to 140° C. using a heater and a reboiler 121, and the pressure was adjusted to approximately 96 kPa-G using a pressure regulating valve. The residence time in the reactor was approximately 17 minutes. Approximately 24700 g/hr of water-containing 1-butanol was transferred from an upper portion of the reactor via a transfer line 6, and approximately 824 g/hr of 1-butanol (made by Wako Pure Chemical Industries, Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 1-butanol was transferred out via the transfer line 2 from a lower portion of the distillation column 110. An alkyltin alkoxide composition containing dibutyltin dibutoxide and 1,1,3,3-tetrabutyl-1,3-di(butyloxy)-distannoxane was obtained from a lower portion of the column reactor 120, and was supplied into a thin film evaporator 130 (made by Kobelco Eco-Solutions Co., Ltd., Japan) via a transfer line 5. 1-Butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyltin dibutoxide and approximately 24 wt % of 1,1,3,3-tetrabutyl-1,3-di(butyloxy)-distannoxane. The composition was cooled to approximately 50° C. using a cooler 131, and transferred at a flow rate of approximately 4812 g/hr via a transfer line 7 into an upper portion of a carbon dioxide complex production apparatus 140. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.45 MPa-G. The reaction temperature in the column reactor 240 was adjusted to 60° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into the carbon dioxide complex-containing mixture. The carbon dioxide complex was transferred via the transfer line 10 at a temperature of 60° C. and a pressure of 0.45 MPa-G, and further supplied using a booster pump 141 via a transfer line 11 at a flow rate of approximately 5576 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 5 hours, whereby a dibutyl carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex (Z: $(CO_2)_x:(OR)_y$) was found to be such that x=1.34 and y=1.72.

The dibutyl carbonate-containing reaction liquid separated out by the thin film evaporator 160 was transferred via a transfer line 16 with the flow rate adjusted to approximately 5020 g/hr into a thin film evaporator 170 (made by Kobelco Eco-Solutions Co., Ltd., Japan) set to approximately 140° C. and approximately 1.4 kPa, and dibutyl carbonate-containing distillate was obtained. The distillate was supplied at approximately 830 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % dibutyl carbonate being obtained at 813 g/hr from a recovery line 20.

Example 24

Step A: Production of Tetraalkyldialkoxydistannoxane 700 g (1.94 mol) of dioctyltin oxide (made by Sankyo Organic Chemicals Co., Ltd., Japan) and 1600 g (15.7 mol) of 2-ethyl-1-butanol (made by Chisso Corporation, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 157° C., and the flask was immersed in the oil bath and rotation of the evaporator was commenced. With the purge valve of the evaporator left open, rotational stirring and heating were carried out for approximately 40 minutes at normal pressure, and then the purge valve was closed, and the pressure in the system was gradually reduced, and water-containing 2-ethyl-1-butanol was distilled off with the pressure in the system at from 84 to 65 kPa. This state was maintained for 7 hours, and then the pressure in the system was further reduced, and excess 2-ethyl-1-butanol was distilled off. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 883 g of reaction liquid was obtained in the flask. According to $^{119}$Sn—, $^1$H—, and $^{13}$C-NMR analysis results, the product 1,1,3,3-tetraoctyl-1,3-bis(2-ethylbutyloxy)-distannoxane was obtained at a yield of 99% based on the dioctyltin oxide. The same procedure was carried out so as to produce 1,1,3,3-tetraoctyl-1,3-bis(2-ethylbutyloxy)-distannoxane to be used in the following step B.

Step B: Production of Carbonate Using Continuous Production Apparatus

A carbonate was produced using a continuous production apparatus as shown in FIG. 6. A liquid mixture of the 1,1,3,3-tetraoctyl-1,3-bis(2-ethylbutyloxy)-distannoxane and 2-ethyl-1-butanol (distannoxane concentration approximately 43 wt %) was supplied at approximately 14233 g/hr from a transfer line 4 into a column reactor 120 of inside diameter 151 mm and effective length 5040 mm packed with a Metal Gauze CY packing (made by Sulzer Chemtech Ltd., Switzerland), and 2-ethyl-1-butanol (made by Chisso Corporation, Japan) that had been purified in a distillation column 110 was supplied at 12260 g/hr from a transfer line 2 into the column reactor 120. The liquid temperature in the reactor was adjusted to 150° C. using a heater and a reboiler 121, and the pressure was adjusted to approximately −2.0 kPa-G using a pressure regulating valve. The residence time in the reactor was approximately 17 minutes. Approximately 12250 g/hr of water-containing 2-ethyl-1-butanol was transferred from an upper portion of the reactor via a transfer line 6, and approximately 958 g/hr of 2-ethyl-1-butanol (made by Chisso Corporation, Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 2-ethyl-1-butanol was transferred out via the transfer line 2 from a lower portion of the distillation column 110. An alkyltin alkoxide composition containing dioctyl-bis(2-ethylbutyloxy)tin and 1,1,3,3-tetraoctyl-1,3-bis(2-ethylbutyloxy)-distannoxane was obtained from a lower portion of the column reactor 120, and was supplied into a thin film evaporator 130 (made by Kobelco Eco-Solutions Co., Ltd., Japan) via a transfer line 5. 2-Ethyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dioctyl-bis(2-ethylbutyloxy)tin and approximately 25 wt % of 1,1,3,3-tetraoctyl-1,3-bis(2-ethylbutyloxy)-distannoxane. The composition was cooled to approximately 40° C. using a cooler 131, and transferred at a flow rate of approximately 6945 g/hr via a transfer line 7 into an upper portion of a carbon dioxide complex production apparatus 140 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.3 MPa-G. The reaction temperature in the column reactor 240 was adjusted to 50° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into the carbon dioxide complex-containing mixture. The carbon dioxide complex was transferred via the transfer line 10 at a temperature of 50° C. and a pressure of 0.3 MPa-G, and further supplied using a booster pump 141 via a transfer line 11 at a flow rate of approximately 7710 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 4 hours, whereby a bis(2-ethylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex (Z: $(CO_2)_x:(OR)_y$) was found to be such that x=1.38 and y=1.72.

The bis(2-ethylbutyl) carbonate-containing reaction liquid separated out by the thin film evaporator 160 was transferred via a transfer line 16 with the flow rate adjusted to approximately 6074 g/hr into a thin film evaporator 170 (made by Kobelco Eco-Solutions Co., Ltd., Japan) set to a temperature of approximately 150° C. and a pressure of approximately 0.3 kPa, and bis(2-ethylbutyl) carbonate-containing distillate was obtained. The distillate was supplied at approximately 964 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(2-ethylbutyl) carbonate being obtained at 956 g/hr from a recovery line 20.

Example 25

1,1,3,3-Tetrabutyl-1,3-bis(3-methylbutyloxy)-distannoxane was produced using the same process as in step A of Example 18, and then a carbonate was produced in the following step.

A carbonate was produced using a continuous production apparatus as shown in FIG. 6. A liquid mixture of the 1,1,3,3-tetrabutyl-1,3-bis(3-methylbutyloxy)-distannoxane and 3-methyl-1-butanol (distannoxane concentration approximately 33 wt %) was supplied at approximately 13385 g/hr from a transfer line 4 into a column reactor 120 of inside diameter 1.51 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14953 g/hr from a transfer line 2 into the column reactor 120. The liquid temperature in the reactor was adjusted to 140° C. using a heater and a reboiler 121, and the pressure was adjusted to approximately 23 kPa-G using a pressure regulating valve. The residence time in the reactor was approximately 17 minutes. Approximately 14900 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 50° C. using a cooler 131, and transferred into an upper portion of a carbon dioxide complex production apparatus 140 at a flow rate of approximately 5130 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.45 MPa-G The reaction temperature in the column reactor 240 was adjusted to 60° C., and a carbon dioxide complex-containing mixture was produced. The carbon dioxide complex-containing mixture obtained was a liquid, and could be transferred out via a transfer line 10 without problems such as blockage of the line occurring. Furthermore, flow of gas through a vent line 12 was not seen, the supplied carbon dioxide and the alkyltin alkoxide composition being converted into the carbon dioxide complex-containing mixture. The mixture was supplied via the transfer line 10 at a flow rate of approximately 5894 g/hr into an autoclave 150 equipped with a stirrer. Carbon dioxide (made by Showa Tansan Co., Ltd., Japan, purity 99.99%, water content not more than 40 ppm) was supplied at approximately 210 g/hr via a supply line 14 into the autoclave, the pressure in the autoclave being maintained at 4 MPa-G. The temperature in the autoclave was set to 120° C., and the residence time was adjusted to approximately 5 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9. At the same time, the amount of carbon dioxide supplied in from the supply line 13 was gradually reduced, and in a steady state the supply of the carbon dioxide from the supply line 13 was stopped, and the unused carbon dioxide was transferred out from the transfer line 17 at approximately 764 g/hr. The carbon dioxide complex-containing mixture obtained was a liquid as in Example 18, and could be transferred out via the transfer line 10 at a temperature of 60° C. and a pressure of 0.45 MPa-G without problems such as blockage of the transfer line occurring. Furthermore, flow of gas through the vent line 12 was not seen, the recycled unused carbon dioxide being recovered in the form of the carbon dioxide complex-containing mixture. The mixture was sampled, and subjected to elemental analysis, whereupon the molar ratio between tin atoms, carbon dioxide, and OR groups in the mixture $(Z:(CO_2)_x:(OR)_y)$ was found to be such that x=1.32 and y=1.72.

The bis(3-methylbutyl) carbonate-containing reaction liquid separated out by the thin film evaporator 160 was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis (3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20. Meanwhile, an alkyltin alkoxide composition-containing residual liquid was obtained from the thin film evaporator 170, and was recycled into the column reactor 120 via a transfer line 18 and the transfer line 4. The residual liquid was supplied into the column reactor 120 at approximately 4388 g/hr, and was reacted with the 3-methyl-1-butanol that had been purified in the distillation column 110. Alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via the transfer line 5. 3-Methyl-1-butanol was evaporated off using the thin film evaporator 130, and returned into the column reactor 120 via the condenser 132, the transfer line 8 and the transfer line 4. The alkyltin alkoxide composition was obtained from the lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 50° C. using the cooler 131, and transferred into the upper portion of the carbon dioxide complex production apparatus 140 at a flow rate of approximately 5130 g/hr via the transfer line 7. The composition was reacted with the unused carbon dioxide (approximately 764 g/hr) separated off from the thin film evaporator 160. The carbon dioxide complex-containing mixture obtained was a liquid as in Example 18, and was transferred out via the transfer line 10 at a temperature of 60° C. and a pressure of 0.45 MPa-G, it being possible to carry out the transfer without problems such as blockage of the transfer line occurring. Furthermore, flow of gas through the vent line 12 was not seen, the recycled alkyltin alkoxide composition and the recycled unused carbon dioxide being converted into the carbon dioxide complex-containing mixture. The mixture was sampled, and subjected to elemental analysis, whereupon the molar ratio between tin atoms, carbon dioxide, and OR groups in the mixture $(Z:(CO_2)_x:(OR)_y)$ was found to be such that x=1.34 and y=1.73.

Reference Example 1

1,1,3,3-Tetrabutyl-1,3-bis(3-methylbutyloxy)-distannoxane was produced using the same process as in step A of Example 18, and then a carbonate was produced in the following step.

A carbonate was produced using a continuous production apparatus as shown in FIG. 6. A liquid mixture of the 1,1,3, 3-tetrabutyl-1,3-bis(3-methylbutyloxy)-distannoxane and 3-methyl-1-butanol (distannoxane concentration approximately 33 wt %) was supplied at approximately 13385 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14953 g/hr from a transfer line 2 into the column reactor 120. The liquid temperature in the reactor was adjusted to 140° C. using a heater and a reboiler 121, and the pressure was adjusted to approximately 22 kPa-G using a pressure regulating valve. The residence time in the reactor was approximately 17 minutes. Approximately 14950 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 50° C. using a cooler 131, and transferred into an upper portion of a carbon dioxide complex production apparatus 140 at a flow rate of approximately 5130 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.5 MPa-G. The reaction temperature in the column reactor 240 was adjusted to 50° C., and a carbon dioxide complex-containing mixture was produced. The carbon dioxide complex-containing mixture obtained was a liquid as in Example 18, and was transferred out via the transfer line 10 at a temperature of 60° C. and a pressure of 0.45 MPa-G, it being possible to carry out the transfer without problems such as blockage of the transfer line occurring. Furthermore, flow of gas through the vent line 12 was not seen, the carbon dioxide and the alkyltin alkoxide composition being converted into the carbon dioxide complex-containing mixture. The mixture was sampled, and subjected to elemental analysis, whereupon the molar ratio between tin atoms, carbon dioxide, and OR groups in the mixture $(Z:(CO_2)_x:(OR)_y)$ was found to be such that x=1.33 and y=1.72. The mixture was supplied via the transfer line 10, a booster pump, and a transfer line 11 at a flow rate of approximately 5894 g/hr into an autoclave 150 equipped with a stirrer. Carbon dioxide (made by Showa Tansan Co., Ltd., Japan, purity 99.99%, water content not more than 40 ppm) was supplied at approximately 212 g/hr via a supply line 14 into the autoclave, the pressure in the autoclave being maintained at 4 MPa-G. The temperature in the autoclave was set to 120° C., and the residence time was adjusted to approximately 5 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and discharged from a vent line 21.

The bis(3-methylbutyl) carbonate-containing reaction liquid separated out by the thin film evaporator 160 was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20. The amount of carbon dioxide consumed in the carbonate production was 210 g/hr based on 973 g/hr of supplied carbon dioxide, and hence the carbon dioxide usage ratio was 22%, i.e. was greatly reduced compared with Example 20.

Comparative Example 5

A carbon dioxide complex-containing mixture was produced using an apparatus as shown in FIG. 9. Approximately 800 g of dibutyltin dimethoxide (made by Aldrich, USA) was transferred via a transfer line 7 into an upper portion of an autoclave 540 equipped with a heat exchange jacket and a stirrer. The autoclave was heated to approximately 180° C., and gaseous carbon dioxide (made by Showa Tansan Co., Ltd., Japan, purity 99.99%, water content not more than 40 ppm) was supplied via a transfer line 9 into the autoclave 540, and the pressure was adjusted to 20 MPa-G, whereby a carbon dioxide complex-containing mixture was produced. The mixture was cooled to room temperature, and transferred out via a transfer line 10, but while solid formed and hence the transfer could not be carried out due to blockage of the line.

Example 26

Step A: Production of
Tetraalkyldialkoxydistannoxane 500 g (2.01 mol) of dibutyltin oxide (made by Sankyo Organic Chemicals Co., Ltd., Japan) and 1047 g (8.04 mol) of 2-ethyl-1-hexanol (made by Wako Pure Chemical Industries, Ltd., Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 157° C., and the flask was immersed in the oil bath and rotation of the evaporator was commenced. With the purge valve of the evaporator left open, rotational stirring and heating were carried out for approximately 40 minutes at normal pressure, and then the purge valve was closed, and the pressure in the system was gradually reduced, and water-containing 2-ethyl-1-hexanol was distilled off with the pressure in the system at from 40 to 20 kPa. This state was maintained for 2 hours, and then the pressure in the system was further reduced, and excess 2-ethyl-1-hexanol was distilled off. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 750 g of reaction liquid was obtained in the flask. According to $^{119}$Sn—, $^{1}$H—, and $^{13}$C-NMR analysis results, the product 1,1,3,3-tetrabutyl-1,3-bis(2-ethylhexyloxy)-distannoxane was obtained at a yield of 98% based on the dibutyltin oxide. The same procedure was carried out so as to produce 1,1,3,3-tetrabutyl-1,3-bis(2-ethylhexyloxy)-distannoxane to be used in the following step B.

Step B: Production of Carbonate Using Continuous Production Apparatus

A carbonate was produced using a continuous production apparatus as shown in FIG. 6. The 1,1,3,3-tetrabutyl-1,3-bis(2-ethylhexyloxy)-distannoxane was supplied at approximately 4943 g/hr from a transfer line 4 into a column reactor 120 of inside diameter 151 mm and effective length 5040 mm packed with a Metal Gauze CY packing (made by Sulzer Chemtech Ltd., Switzerland), and 2-ethyl-1-hexanol (made by Wako Pure Chemical Industries, Ltd., Japan) that had been purified in a distillation column 110 was supplied at 15653 g/hr from a transfer line 2 into the column reactor 120. The liquid temperature in the reactor was adjusted to 140° C. using a heater and a reboiler 121, and the pressure was adjusted to approximately −58 kPa-G using a pressure regulating valve. The residence time in the reactor was approximately 17 minutes. Approximately 15000 g/hr of water-containing 2-ethyl-1-hexanol was transferred from an upper portion of the reactor via a transfer line 6, and approximately 1223 g/hr of 2-ethyl-1-hexanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 2-ethyl-1-hexanol was transferred out via the transfer line 2 from a lower portion of the distillation column 110. An alkyltin alkoxide composition containing dibutyl-bis(2-ethylhexyloxy)tin and 1,1,3,3-tetrabutyl-1,3-bis(2-ethylhexyloxy)-distannoxane was obtained from a lower portion of the column reactor 120, and was supplied into a thin film evaporator 130 (made by Kobelco Eco-Solutions Co., Ltd., Japan) via a transfer line 5. 2-Ethyl-1-hexanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 70 wt % of dibutyl-bis(2-ethylhexyloxy)tin and approximately 28 wt % of 1,1,3,3-tetrabutyl-1,3-bis(2-ethylhexyloxy)-distannoxane. The composition was cooled to approximately 100° C. using a cooler 131, and transferred via a transfer line 7 into an upper portion of a carbon dioxide complex production apparatus 140 at a flow rate of approximately 6083 g/hr. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at normal pressure at approximately 764 g/hr via a supply line 13 and a transfer line 9 into a lower portion of the column reactor 240. The reaction temperature in the column reactor 240 was adjusted to 100° C., and a carbon dioxide complex-containing mixture was produced. Approximately 380 g/hr of unreacted carbon dioxide flowed through a vent line 12. The carbon dioxide complex-containing mixture obtained was a liquid as in Example 18, and was transferred out via a transfer line 10 at a temperature of 100° C. and normal pressure, it being possible to carry out the transfer without problems such as blockage of the transfer line occurring. The mixture was sampled, and subjected to elemental analysis, whereupon the molar ratio between tin atoms, carbon dioxide, and OR groups in the mixture (Z:(CO$_2$)$_x$:(OR)$_y$) was found to be such that x=0.65 and y=1.71. The mixture was supplied via the transfer line 10, a booster pump, and a transfer line 11 at a flow rate of approximately 6465 g/hr into an autoclave 150 equipped with a stirrer. Carbon dioxide (made by Showa Tansan Co., Ltd., Japan, purity 99.99%, water content not more than 40 ppm) was supplied at approximately 592 g/hr via a supply line 14 into the autoclave, the pressure in the autoclave being maintained at 4 MPa-G. The temperature in the autoclave was set to 120° C., and the residence time was adjusted to approximately 4 hours, whereby a bis(2-ethylhexyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 382 g/hr. The carbon dioxide complex-containing mixture obtained was a liquid as in Example 18, and was transferred out via the transfer line 10 at a temperature of 100° C. and normal pressure, it being possible to carry out the transfer without problems such as blockage of the transfer line occurring. The flow of carbon dioxide gas through the vent line 12 was approximately 380 g/hr. The mixture was sampled, and subjected to elemental analysis, whereupon the molar ratio between tin atoms, carbon dioxide, and OR groups in the mixture (Z:(CO$_2$)$_x$:(OR)$_y$) was found to be such that x=0.65 and y=1.71.

The bis(2-ethylhexyl) carbonate-containing reaction liquid separated out by the thin film evaporator 160 was transferred via a transfer line 16 with the flow rate adjusted to approximately 6282 g/hr into a thin film evaporator 170 (made by Kobelco Eco-Solutions Co., Ltd., Japan) set to approximately 160° C. and approximately 0.1 kPa, and bis(2-ethylhexyl) carbonate-containing distillate was obtained.

The distillate was supplied at approximately 1350 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(2-ethylhexyl) carbonate being obtained at 1338 g/hr from a recovery line 20. The amount of carbon dioxide consumed in the carbonate production was 210 g/hr based on 590 g/hr of supplied carbon dioxide, and hence the carbon dioxide usage ratio was approximately 35%.

Example 27

Step A: Production of Tetraalkyldialkoxydistannoxane

The same procedure as in Example 21 was carried out, so as to produce 1,1,3,3-tetraoctyl-1,3-bis(3-methylbutyloxy)-distannoxane to be used in the following step B.

Step B: Production of Carbonate Using Continuous Production Apparatus

A carbon dioxide complex-containing mixture was produced using an apparatus as shown in FIG. 6. The 1,1,3,3-tetraoctyl-1,3-bis(3-methylbutyloxy)-distannoxane produced in step A was supplied at 5885 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at approximately 1000 g/hr from a transfer line 2 into the column reactor 120. The liquid temperature in the reactor was adjusted to 140° C. using a heater and a reboiler 121, and the pressure was adjusted to approximately 23 kPa-G using a pressure regulating valve. The residence time in the reactor was approximately 17 minutes. Approximately 700 g/hr of water-containing 3-methyl-1-butanol was transferred from an upper portion of the reactor via a transfer line 6, and approximately 70 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 18 mol % of dioctyl-bis(3-methylbutyloxy)tin and approximately 82 mol % of 1,1,3,3-tetraoctyl-1,3-bis(3-methylbutyloxy)-distannoxane. The composition was cooled to approximately 15° C. using a cooler 131, and transferred into an upper portion of a carbon dioxide complex production apparatus 140 at a flow rate of approximately 6010 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of 0.4 MPa-G at approximately 500 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at a temperature of 20° C. and a pressure of 0.4 MPa-G via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture ($Z:(CO_2)_x:(OR)_y$) was found to be such that x=0.75 and y=1.09. The carbon dioxide complex was transferred via the transfer line 10, and further supplied using a booster pump 141 via a transfer line 11 at a flow rate of approximately 6500 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 6 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex ($Z:(CO_2)_x:(OR)_y$) was found to be such that x=0.75 and y=1.09.

The bis(3-methylbutyl) carbonate-containing reaction liquid separated out by the thin film evaporator 160 was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 200 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 185 g/hr from a recovery line 20.

Example 28

Step A: Production of Tetraalkyldialkoxydistannoxane

The same procedure as in Example 21 was carried out, so as to produce 1,1,3,3-tetraoctyl-1,3-bis(3-methylbutyloxy)-distannoxane to be used in the following step B.

Step B: Production of Carbonate Using Continuous Production Apparatus

A carbon dioxide complex-containing mixture was produced using an apparatus as shown in FIG. 6. The 1,1,3,3-tetraoctyl-1,3-bis(3-methylbutyloxy)-distannoxane produced in step A was supplied at 5880 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at approximately 100 g/hr from a transfer line 2 into the column reactor 120. The liquid temperature in the reactor was adjusted to 140° C. using a heater and a reboiler 121, and the pressure was adjusted to approximately 21 kPa-G using a pressure regulating valve. The residence time in the reactor was approximately 17 minutes. Approximately 70 g/hr of water-containing 3-methyl-1-butanol was transferred from an upper portion of the reactor via a transfer line 6, and approximately 5 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 97 mol % of 1,1,3,3-tetraoctyl-1,3-bis(3-methylbutyloxy)-distannoxane. The composition was cooled to approximately 15° C. using a cooler 131, and transferred into an upper portion of a carbon dioxide complex production apparatus 140 at a flow rate of approximately 5890 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at a pressure of 0.4 MPa-G at approximately 500 g/hr via a transfer line 9 into a lower portion of the column reactor 240. The reaction temperature in the column reactor 240 was adjusted to approximately 20° C., and a carbon dioxide complex-containing mixture was produced. The mixture was a liquid, and was transferred out at a temperature of 20° C. and a pressure of 0.4 MPa-G via a transfer line 10, it being possible to carry out the transfer via the transfer line 10 without problems such as blockage of the line occurring. The mixture was sampled, and subjected to elemental analysis, whereupon the molar ratio between tin atoms, carbon dioxide, and OR groups in the mixture (Z:$(CO_2)_x$:$(OR)_y$) was found to be such that x=0.56 and y=0.98. The carbon dioxide complex was transferred via the transfer line 10, and further supplied using a booster pump 141 via a transfer line 11 at a flow rate of approximately 6300 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 6 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex (Z:$(CO_2)_x$:$(OR)_y$) was found to be such that x 0.55 and y=0.98.

The bis(3-methylbutyl) carbonate-containing reaction liquid separated out by the thin film evaporator 160 was transferred via a transfer line 16 with the flow rate adjusted to approximately 5990 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 90 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at approximately 80 g/hr from a recovery line 20.

Example 29

Step A: Production of Tetraalkyldialkoxydistannoxane 1,1,3,3-Tetraoctyl-1,3-bis(3-methylbutyloxy)-distannoxane was produced using the same process as in step A of Example 21, and then a carbonate was produced in the following step.

Step B: Production of Carbonate Using Continuous Production Apparatus

A carbonate was produced using a continuous production apparatus as shown in FIG. 6. The 1,1,3,3-tetraoctyl-1,3-bis(3-methylbutyloxy)-distannoxane was transferred at a flow rate of approximately 5887 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at approximately 14953 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 14000 g/hr of water-containing 3-methyl-1-butanol was transferred from an upper portion of the reactor via a transfer line 6, and approximately 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 72 wt % of dioctyl-bis(3-methylbutyloxy)tin and approximately 27 wt % of 1,1,3,3-tetraoctyl-1,3-bis(3-methylbutyloxy)-distannoxane. The composition was cooled to approximately 40° C. using a cooler 131, and transferred into an upper portion of a carbon dioxide complex production apparatus 140 at a flow rate of approximately 6627 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.25 MPa-G. The reaction temperature in the column reactor 240 was adjusted to 50° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into a carbon dioxide complex-containing mixture. The mixture was supplied via the transfer line 10 at a flow rate of approximately 7391 g/hr into an autoclave 150 equipped with a stirrer. Carbon dioxide (made by Showa Tansan Co., Ltd., Japan, purity 99.99%, water content not more than 40 ppm) was supplied at approximately 210 g/hr via a supply line 14 into the autoclave, the pressure in the autoclave being maintained at 4 MPa-G. The temperature in the autoclave was set to 120° C., and the residence time was adjusted to approximately 7 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9. At the same time, the amount of carbon dioxide supplied in from the supply line 13 was gradually reduced, and in a steady state the supply of the carbon dioxide from the supply line 13 was stopped, and the unused carbon dioxide was transferred out from the transfer line 17 at approximately 764 g/hr. The carbon dioxide complex-containing mixture obtained was a liquid as in Example 18, and was transferred out via the transfer line 10 at a temperature of 50° C. and a pressure of 0.25 MPa-G, it being possible to carry out the transfer without problems such as blockage of the transfer line occurring. Furthermore, flow of gas through the vent line 12 was not seen, the recycled unused carbon dioxide being recovered in the form of the carbon dioxide complex-containing mixture. The mixture was sampled, and subjected to elemental analysis, whereupon the molar ratio between tin atoms, carbon dioxide, and OR groups in the mixture (Z: $(CO_2)_x$:$(OR)_y$) was found to be such that x=1.33 and y=1.72.

The bis(3-methylbutyl) carbonate-containing reaction liquid separated out by the thin film evaporator 160 was transferred via a transfer line 16 into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20. Meanwhile, an alkyltin alkoxide composition-containing residual liquid was obtained from the thin film evaporator 170, and was recycled into the column reactor 120 via a transfer line 18 and the transfer line 4. The residual liquid was analyzed, and the 1,1,3,3-tetraoctyl-1,3-bis(3-methylbutyloxy)-distannoxane produced in step A was supplied in from a supply line 22 such that the 1,1,3,3-tetraoctyl-1,3-bis(3-methylbutyloxy)-distannoxane flow rate was approximately 5887 g/hr, and this was transferred into the column reactor 120 via the transfer line 18 and the transfer line 4, and reacted with the 3-methyl-1-butanol that had been purified in the distillation column 110. Alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via the transfer line 5. 3-Methyl-1-butanol was evaporated off using the thin film evaporator 130, and returned into the column reactor 120 via the condenser 132, the transfer line 8 and the transfer line 4. The alkyltin alkoxide composition was obtained from the lower portion of the thin film evaporator 130, this composition containing approximately 72 wt % of dioctyl-bis(3-methylbutyloxy)tin and approximately 27% of 1,1,3,3-tetraoctyl-1,3-bis(3-methylbutyloxy)-distannoxane. The composition was cooled to approximately 50° C. using the cooler 131, and transferred into the upper portion of the carbon dioxide complex production apparatus 140 at a flow rate of approximately 6627 g/hr via the transfer line 7. The composition was reacted with the unused carbon dioxide (approximately 764 g/hr) separated off from the thin film evaporator 160. The carbon dioxide complex-containing mixture obtained was a liquid as in Example 18, and was transferred out via the transfer line 10 at a temperature of 50° C. and a pressure of 0.25 MPa-G, it being possible to carry out the transfer without problems such as blockage of the transfer line occurring. Furthermore, flow of gas through the vent line 12 was not seen, the recycled alkyltin alkoxide composition and the recycled unused carbon dioxide being converted into the carbon dioxide complex-containing mixture. The mixture was sampled, and subjected to elemental analysis, whereupon the molar ratio between tin atoms, carbon dioxide, and OR groups in the mixture $(Z:(CO_2)_x:(OR)_y)$ was found to be such that x=1.31 and y=1.71. Continuous operation was carried out for approximately 600 hours under the above conditions. It was found that, after that, the alkyltin alkoxide composition recovered from the transfer line 18 contained approximately 60 wt % of 1,1,3,3-tetraoctyl-1,3-bis(3-methylbutyloxy)-distannoxane, and also contained approximately 20 wt % of trioctyl-(3-methylbutyloxy)-tin, and furthermore shifts originating from a plurality of tin compounds were also seen in a range of from −220 to −605 ppm in the $^{119}$Sn-NMR spectrum. The carbon dioxide complex-containing mixture obtained from the transfer line 10 was sampled and analyzed, whereupon the molar ratio between tin atoms, carbon dioxide, and OR groups in the mixture $(Z:(CO_2)_x:(OR)_y)$ was found to be such that x=1.31 and y=1.72. Moreover, the bis(3-methylbutyl) carbonate yield was continuously approximately 944 g/hr.

Example 30

Step A: Production of Tetraalkyldialkoxydistannoxane 1,1,3,3-Tetraoctyl-1,3-bis(3-methylbutyloxy)-distannoxane was produced using the same process as in step A of Example 21, and then a carbonate was produced in the following step.

Step B: Production of Carbonate Using Continuous Production Apparatus

A carbonate was produced using a continuous production apparatus as shown in FIG. 6. The 1,1,3,3-tetraoctyl-1,3-bis(3-methylbutyloxy)-distannoxane was transferred at 5887 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at approximately 14953 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 14000 g/hr of water-containing 3-methyl-1-butanol was transferred from an upper portion of the reactor via a transfer line 6, and approximately 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 72 wt % of dioctyl-bis(3-methylbutyloxy)tin and approximately 27 wt % of 1,1,3,3-tetraoctyl-1,3-bis(3-methylbutyloxy)-distannoxane. The composition was cooled to approximately 40° C. using a cooler 131, and transferred into an upper portion of a carbon dioxide complex production apparatus 140 at a flow rate of approximately 6627 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.25 MPa-G. The reaction temperature in the column reactor 240 was adjusted to 50° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into the carbon dioxide complex-containing mixture. The mixture was supplied via the transfer line 10 at a flow rate of approximately 7391 g/hr into an autoclave 150 equipped with a stirrer. Carbon dioxide (made by Showa Tansan Co., Ltd., Japan, purity 99.99%, water content not more than 40 ppm) was supplied at approximately 210 g/hr via a supply line 14 into the autoclave, the pressure in the autoclave being maintained at 4 MPa-G. The temperature in the autoclave was set to 120° C., and the residence time was adjusted to approximately 7 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9. At the same time, the amount of carbon dioxide supplied in from the supply line 13 was gradually reduced, and in a steady state the supply of the carbon dioxide from the supply line 13 was stopped, and the unused carbon dioxide was transferred out from the transfer line 17 at approximately 764 g/hr. The carbon dioxide complex-containing mixture obtained was a liquid as in Example 18, and was transferred out via the transfer line 10 at a temperature of 50° C. and a pressure of 0.25 MPa-G, it being possible to carry out the transfer without problems such as blockage of the transfer line occurring. Furthermore, flow of gas through the vent line 12 was not seen, the recycled unused carbon dioxide being recovered in the form of the carbon dioxide complex-containing mixture. The mixture was sampled, and subjected to elemental analysis, whereupon the molar ratio between tin atoms, carbon dioxide, and OR groups in the mixture (Z:$(CO_2)_x$:$(OR)_y$) was found to be such that x=1.30 and y=1.71.

The bis(3-methylbutyl) carbonate-containing reaction liquid separated out by the thin film evaporator 160 was transferred via a transfer line 16 into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20. Meanwhile, an alkyltin alkoxide composition-containing residual liquid was obtained from the thin film evaporator 170, and was recycled into the column reactor 120 via a transfer line 18 and the transfer line 4, and was reacted with the 3-methyl-1-butanol that had been purified in the distillation column 110. Alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 72 wt % of dioctyl-bis(3-methylbutyloxy)tin and approximately 27% of 1,1,3,3-tetraoctyl-1,3-bis(3-methylbutyloxy)-distannoxane. The composition was cooled to approximately 50° C. using the cooler 131, and transferred at a flow rate of approximately 6627 g/hr via the transfer line 7 into the upper portion of the carbon dioxide complex production apparatus 140. The composition was reacted with the unused carbon dioxide (approximately 764 g/hr) separated off from the thin film evaporator 160. The carbon dioxide complex-containing mixture obtained was a liquid as in Example 18, and was transferred out via the transfer line 10 at a temperature of 50° C. and a pressure of 0.25 MPa-G, it being possible to carry out the transfer without problems such as blockage of the transfer line occurring. Furthermore, flow of gas through the vent line 12 was not seen, the recycled alkyltin alkoxide composition and the recycled unused carbon dioxide being converted into the carbon dioxide complex-containing mixture. The mixture was sampled, and subjected to elemental analysis, whereupon the molar ratio between tin atoms, carbon dioxide, and OR groups in the mixture (Z:$(CO_2)_x$:$(OR)_y$) was found to be such that x=1.3 and y=1.7. Continuous operation was carried out for approximately 1800 hours under the above conditions. It was found that, after that, the alkyltin alkoxide composition recovered from the transfer line 18 contained approximately 10 wt % of 1,1,3,3-tetraoctyl-1,3-bis(3-methylbutyloxy)-distannoxane, and also contained approximately 45 wt % of trioctyl-(3-methylbutyloxy)-tin, and furthermore shifts originating from a plurality of tin compounds were also seen in a range of from −220 to −605 ppm in the $^{119}$Sn-NMR spectrum. The carbon dioxide complex-containing mixture obtained from the transfer line 10 was sampled and analyzed, whereupon the molar ratio between tin atoms, carbon dioxide, and OR groups in the mixture (Z:$(CO_2)_x$:$(OR)_y$) was found to be such that x=1.02 and y=0.96. Moreover, the bis(3-methylbutyl) carbonate yield continuously decreased, being approximately 56 g/hr after approximately 1200 hours of operation.

Example 31

Step A: Production of Tetraalkyldialkoxydistannoxane

The same procedure as in Example 21 was carried out, so as to produce 1,1,3,3-tetraoctyl-1,3-bis(3-methylbutyloxy)-distannoxane to be used in the following step B.

Step B: Production of Dry Gaseous Carbon Dioxide

A carbon dioxide complex-containing mixture was produced using an apparatus as shown in FIG. 4. The 1,1,3,3-tetraoctyl-1,3-bis(3-methylbutyloxy)-distannoxane produced in step A was supplied at 1200 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 20000 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 18000 g/hr of water-containing 3-methyl-1-butanol was transferred from an upper portion of the reactor via a transfer line 6, and approximately 100 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and recovered from a transfer line 8 via a condenser 132. The alkyltin alkoxide composition was obtained from a lower portion of the thin film evaporator 130, this composition containing approximately 90 mol % of dioctyl-bis(3-methylbutyloxy)tin and approximately 10 mol % of 1,1,3,3-tetraoctyl-1,3-bis(3-methylbutyloxy)-distannoxane. The composition was cooled to approximately 30° C. using a cooler 131, and transferred into an upper portion of a carbon dioxide complex production apparatus 140 at a flow rate of approximately 1375 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.9%, water content approximately 120 ppm) was supplied at a pressure of 0.1 MPa-G at approximately 200 g/hr via a transfer line 9 into a lower portion of the column reactor 240. The reaction temperature in the column reactor 240 was adjusted to approximately 40° C., and a carbon dioxide complex-containing mixture was produced. The mixture was a liquid, and was transferred out at a temperature of 40° C. and a pressure of 0.1 MPa-G via a transfer line 10, it being possible to carry out the transfer via the transfer line 10 continuously without problems such as blockage of the line occurring. The mixture was sampled, and subjected to elemental analysis, whereupon the molar ratio between tin atoms, carbon dioxide, and OR groups in the mixture ($Z:(CO_2)_x:(OR)_y$) was found to be such that $x=1.34$ and $y=1.80$. The mixture was heated to approximately 120° C., so as to eliminate the carbon dioxide. The carbon dioxide was analyzed, and found to have a water content of approximately 10 ppm. Carbon dioxide was continuously withdrawn in a gaseous form from the vent line 12, and was analyzed, and found to have a water content of approximately 10 ppm.

Comparative Example 6

Carbon dioxide absorption was carried out using a sodium hydroxide aqueous solution. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as an apparatus. The sodium hydroxide aqueous solution (made by Wako Pure Chemical Industries, Ltd, Japan, concentration 5 mol/L) was supplied into an upper portion of the column reactor 240 via a transfer line 7 at approximately 1.5 L/hr, and gaseous carbon dioxide (made by Showa Tansan Co., Ltd., Japan, purity 99.9%, water content approximately 120 ppm) was supplied at a pressure of 0.1 MPa-G at approximately 200 g/hr via a transfer line 9 into a lower portion of the column reactor 240. The reaction temperature in the column reactor 240 was adjusted to approximately 40° C., and carbon dioxide absorption was carried out. Carbon dioxide was continuously withdrawn in a gaseous form from a vent line 12, and was analyzed, and found to have a water content of approximately 5000 ppm. Approximately 1 L of the sodium hydroxide aqueous solution that had been reacted with the carbon dioxide was recovered from a transfer line 10, and approximately 1.2 L of a sulfuric acid aqueous solution (made by Wako Pure Chemical Industries, Ltd., Japan, 47%) was added to the sodium hydroxide aqueous solution, so as to eliminate the carbon dioxide. The carbon dioxide was analyzed, and was found to have a water content of approximately 6000 ppm.

Example 32

Step A: Production of Tetraalkyldialkoxydistannoxane 1,1,3,3-Tetraoctyl-1,3-bis(2-ethyl butyloxy)-distannoxane was produced using the same process as in step A of Example 24, and then a carbonate was produced in the following step.

Step B: Production of Carbonate Using Continuous Production Apparatus

A carbonate was produced using a continuous production apparatus as shown in FIG. 6. The 1,1,3,3-tetraoctyl-1,3-bis(2-ethylbutyloxy)-distannoxane was supplied at 6074 g/hr from a transfer line 4 into a column reactor 120 of inside diameter 151 mm and effective length 5040 mm packed with a Metal Gauze CY packing (made by Sulzer Chemtech Ltd., Switzerland), and 2-ethyl-1-butanol (made by Chisso Corporation, Japan) that had been purified in a distillation column 110 was supplied at 13500 g/hr from a transfer line 2 into the column reactor 120. The liquid temperature in the reactor was adjusted to 160° C. using a heater and a reboiler 121, and the pressure was adjusted to approximately 31 kPa-G using a pressure regulating valve. The residence time in the reactor was approximately 17 minutes. Approximately 12350 g/hr of water-containing 2-ethyl-1-butanol was transferred from an upper portion of the reactor via a transfer line 6, and approximately 958 g/hr of 2-ethyl-1-butanol (made by Chisso Corporation, Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 2-ethyl-1-butanol was transferred out via the transfer line 2 from a lower portion of the distillation column 110. An alkyltin alkoxide composition containing dioctyl-bis(2-ethylbutyloxy)tin and 1,1,3,3-tetraoctyl-1,3-bis(2-ethylbutyloxy)-distannoxane was obtained from a lower portion of the column reactor 120, and was supplied into a thin film evaporator 130 (made by Kobelco Eco-Solutions Co., Ltd., Japan) via a transfer line 5. 2-ethyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dioctyl-bis(2-ethylbutyloxy)tin and approximately 25 wt % of 1,1,3,3-tetraoctyl-1,3-bis(2-ethylbutyloxy)-distannoxane. The composition was cooled to approximately 40° C. using a cooler 131, and transferred at a flow rate of approximately 6945 g/hr via a transfer line 7 into an upper portion of a carbon dioxide complex production apparatus 140 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 973 g/hr via a supply line 13 and a transfer line 9 into a lower portion of the column reactor 240. The pressure in the column was adjusted to 1 MPa-G. The reaction temperature in the column reactor 240 was adjusted to approximately 45° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into a carbon dioxide complex-containing mixture. The carbon dioxide complex was transferred via the transfer line 10 at a temperature of approximately 45° C. and a pressure of 1 MPa-G, and further supplied using a booster pump 141 via a transfer line 11 at a flow rate of approximately 7710 g/hr into an autoclave 150 equipped with a stirrer. With carbon dioxide not being supplied into the autoclave 150, the temperature in the autoclave was set to 120° C., and the residence time was adjusted to approximately 4 hours, whereby a bis(2-ethylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex (Z: $(CO_2)_x:(OR)_y$) was found to be such that x=1.65 and y=1.70.

The bis(2-ethylbutyl) carbonate-containing reaction liquid separated out by the thin film evaporator 160 was transferred via a transfer line 16 with the flow rate adjusted to approximately 6074 g/hr into a thin film evaporator 170 (made by Kobelco Eco-Solutions Co., Ltd., Japan) set to a temperature of approximately 150° C. and a pressure of approximately 0.3 kPa, and bis(2-ethylbutyl) carbonate-containing distillate was obtained. The distillate was supplied at approximately 964 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(2-ethylbutyl) carbonate being obtained at 956 g/hr from a recovery line 20.

Example 33

Step A: Production of Tetraalkyldialkoxydistannoxane 1,1,3,3-Tetraoctyl-1,3-bis(3-methylbutyloxy)-distannoxane was produced using the same process as in step A of Example 21, and then a carbonate was produced in the following step.

Step B: Production of Carbonate Using Continuous Production Apparatus

Figure 8:
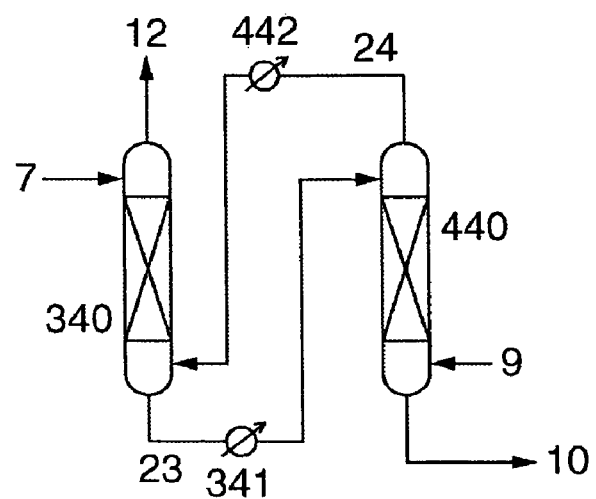
FIG. 8 shows a schematic diagram of an apparatus for producing a carbon dioxide complex-containing mixture.

A carbonate was produced using a continuous production apparatus as shown in FIG. 6. The 1,1,3,3-tetraoctyl-1,3-bis (3-methylbutyloxy)-distannoxane was supplied at 5887 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at approximately 14953 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 14953 g/hr of water-containing 3-methyl-1-butanol was transferred from an upper portion of the reactor via a transfer line 6, and approximately 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 73 wt % of dioctyl-bis(3-methylbutyloxy)tin and approximately 26 wt % of 1,1,3,3-tetraoctyl-1,3-bis(3-methylbutyloxy)-distannoxane. The composition was cooled to approximately 40° C. using a cooler 131, and transferred at a flow rate of approximately 6630 g/hr via a transfer line 7 into an upper portion of a carbon dioxide complex production apparatus 140. A combination of a column reactor 340 and a column reactor 440 each of inside diameter 53.5 mm and effective length 1380 mm (packed length approximately 1000 mm) packed with a Dixon packing (made by Tokyo Tokushu Kanaami, Japan, size 6 mm) as shown in FIG. 8 was used as the carbon dioxide complex production apparatus 140 (the two column reactors were the same as one another, and were joined together by a transfer line 23 and a transfer line 24). Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 440. The pressure in the column was adjusted to 0.02 MPa-G. Unreacted carbon dioxide in the column reactor 440 was transferred via the transfer line 24 and a cooler 442 into a lower portion of the column reactor 340, and was further reacted with the alkyltin alkoxide composition in the column reactor 340. A carbon dioxide complex-containing mixture was obtained from the lower portion of the column reactor 340, and the mixture, which was at a temperature of approximately 68° C., was cooled to approximately 20° C. using a cooler 341, and transferred via the transfer line 23 into the upper portion of the column reactor 440, and further reacted with the carbon dioxide. The carbon dioxide complex-containing mixture obtained from the lower portion of the column reactor 440 was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into a carbon dioxide complex-containing mixture. The carbon dioxide complex was transferred via the transfer line 10 at a temperature of approximately 24° C. and a pressure of 0.02 MPa-G, and further supplied using a booster pump 141 via a transfer line 11 at a flow rate of approximately 7394 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 6 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex $(Z:(CO_2)_x:(OR)_y)$ was found to be such that x=1.34 and y=1.72.

The bis(3-methylbutyl) carbonate-containing reaction liquid separated out by the thin film evaporator 160 was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20.

Example 34

Step A: Production of
Tetraalkyldialkoxydistannoxane 1,1,3,3-Tetraoctyl-1,3-bis(3-methylbutyloxy)-distannoxane was produced using the same process as in step A of Example 21, and then a carbonate was produced in the following step.

Step B: Production of Carbonate Using Continuous Production Apparatus

A carbonate was produced using a continuous production apparatus as shown in FIG. 6. The 1,1,3,3-tetraoctyl-1,3-bis(3-methylbutyloxy)-distannoxane was supplied at 5887 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at approximately 14953 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. Approximately 14953 g/hr of water-containing 3-methyl-1-butanol was transferred from an upper portion of the reactor via a transfer line 6, and approximately 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dioctyl-bis(3-methylbutyloxy)tin and 1,1,3,3-tetraoctyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 73 wt % of dioctyl-bis(3-methylbutyloxy)tin and approximately 26 wt % of 1,1,3,3-tetraoctyl-1,3-bis(3-methylbutyloxy)-distannoxane. The composition was cooled to approximately 40° C. using a cooler 131, and transferred at a flow rate of approximately 6630 g/hr via a transfer line 7 into a carbon dioxide complex production apparatus 140. An autoclave 540 equipped with a heat exchange jacket and a stirrer as shown in FIG. 9 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a transfer line 9 into a lower portion of the autoclave 540, and the pressure was adjusted to 0.25 MPa-G. The reaction temperature in the autoclave 540 was adjusted to 50° C., and a carbon dioxide complex-containing mixture was produced. The carbon dioxide complex-containing mixture obtained was a liquid, and could be transferred out via a transfer line 10 without problems such as blockage of the transfer line occurring. Furthermore, flow of gas through a vent line 12 was not seen, the supplied carbon dioxide and the alkyltin alkoxide composition being converted into a carbon dioxide complex-containing mixture. The carbon dioxide complex was transferred via the transfer line 10 at a temperature of 50° C. and a pressure of 0.25 MPa-G, and further supplied using a booster pump 141 via a transfer line 11 at a flow rate of approximately 7394 g/hr into an autoclave 150 equipped with a stirrer. Carbon dioxide was supplied at approximately 210 g/hr via a supply line 14 into the autoclave 150, the pressure in the autoclave being maintained at 4 MPa-G. The temperature in the autoclave was set to 120° C., and the residence time was adjusted to approximately 6 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was recycled into the carbon dioxide complex production apparatus 140 via a cooler 162, a transfer line 17, a compressor 163, and the transfer line 9, and reacted with the alkyltin alkoxide composition which was transferred in via the transfer line 7, so as to produce the carbon dioxide complex-containing mixture. At the same time, the amount of carbon dioxide supplied in from the supply line 13 was gradually reduced, and in a steady state the supply of the carbon dioxide from the supply line 13 was stopped, the carbon dioxide supply being made to be from the supply line 14 only, and the unused carbon dioxide was transferred out from the transfer line 17 at approximately 764 g/hr. The carbon dioxide complex-containing mixture obtained was a liquid, and could be transferred out via the transfer line 10 without problems such as blockage of the transfer line occurring. Furthermore, flow of gas through the vent line 12 was not seen, the supplied unused carbon dioxide being recovered as carbon dioxide complex. The carbon dioxide complex was sampled, and subjected to elemental analysis, whereupon the molar ratio between tin atoms, carbon dioxide, and OR groups in the carbon dioxide complex (Z: $(CO_2)_x$:$(OR)_y$) was found to be such that x=1.35 and y=1.72.

The bis(3-methylbutyl) carbonate-containing reaction liquid separated out by the thin film evaporator 160 was transferred via a transfer line 16 with the flow rate adjusted to approximately 5332 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20.

Example 35

1,1,3,3-Tetrabutyl-1,3-bis(3-methylbutyloxy)-distannoxane was produced using the same process as in step A of Example 18, and then a carbonate was produced in the following step.

Figure 10:
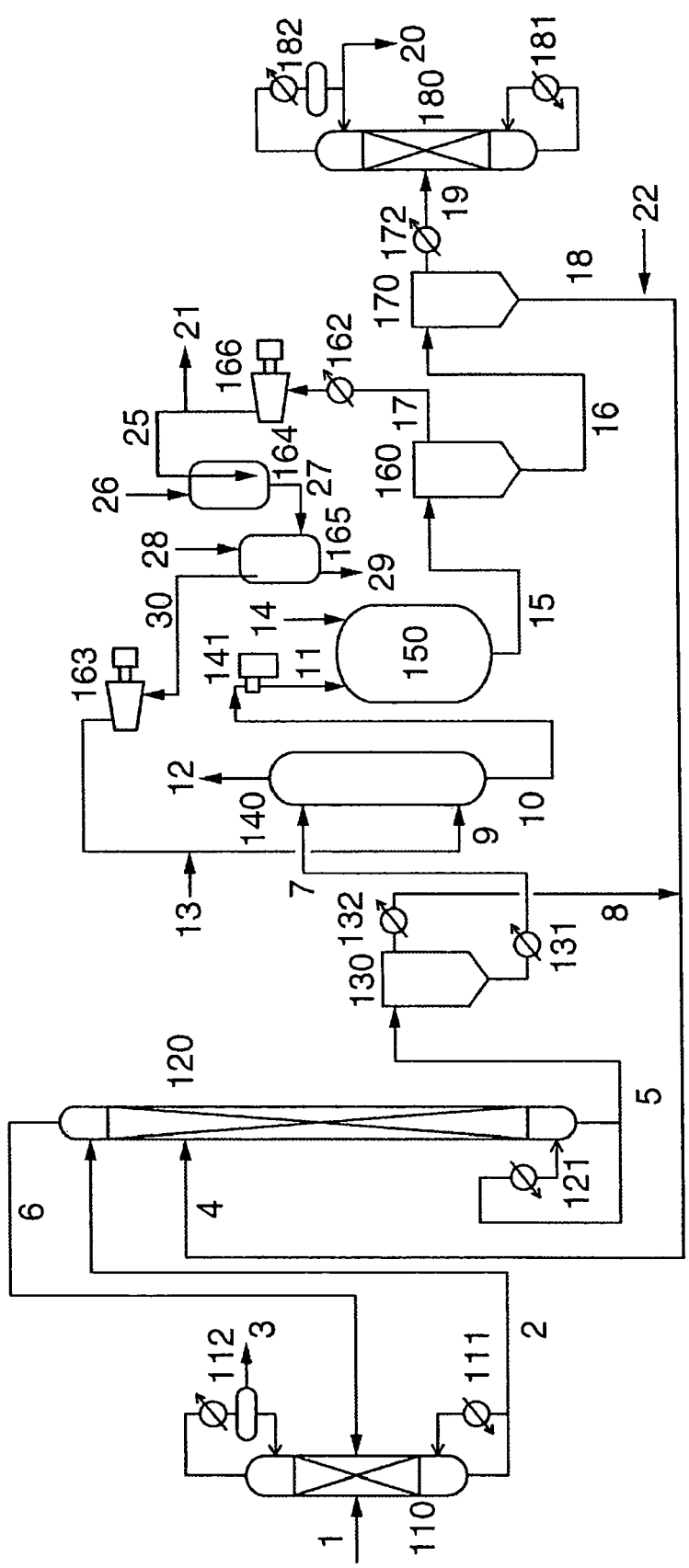
FIG. 10 shows a schematic diagram of a carbonate production apparatus including a step of producing a carbon dioxide complex-containing mixture.

A carbonate was produced using a continuous production apparatus as shown in FIG. 10. The 1,1,3,3-tetrabutyl-1,3-bis(3-methylbutyloxy)-distannoxane was supplied at 4388 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14952 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. 14000 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 30° C. using a cooler 131, and transferred into an upper portion of a carbon dioxide complex production apparatus 140 at a flow rate of approximately 5130 g/hr via a transfer line 7. A column reactor 240 of inside diameter 53.5 mm and effective length 2680 mm (packed length approximately 2000 mm) packed with a Dixon packing (made by Tokyo Tokushu Kanaami, Japan, size 6 mm) and equipped with a cooling jacket as shown in FIG. 7 was used as the carbon dioxide complex production apparatus 140. Gaseous carbon dioxide (made by Showa Tansan Co., Ltd., Japan, purity 99.99%, water content not more than 40 ppm) was supplied at approximately 764 g/hr via a supply line 13 and a transfer line 9 into a lower portion of the column reactor 240. The pressure in the column was adjusted to 0.05 MPa-G The reaction temperature in the column reactor 240 was adjusted to 40° C., and carbon dioxide complex was produced. The carbon dioxide complex obtained was a liquid, and could be transferred out via a transfer line 10 without problems such as blockage of the line occurring. Furthermore, flow of gas through a vent line 12 was not seen, the supplied carbon dioxide and the alkyltin alkoxides being converted into a carbon dioxide complex-containing mixture. The mixture was supplied via the transfer line 10 at a flow rate of approximately 5894 g/hr into an autoclave 150 equipped With a stirrer. Carbon dioxide was supplied at approximately 210 g/hr via a supply line 14 into the autoclave, the pressure in the autoclave being maintained at 4 MPa-G. The temperature in the autoclave was set to 120° C., and the residence time was adjusted to approximately 5 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was transferred into a tank reactor 164 via a cooler 162, a transfer line 17, a compressor 166, and a transfer line 25. A sodium hydroxide aqueous solution (made by Wako Pure Chemical Industries, Ltd, Japan, concentration 8 mol/L) was supplied into the tank reactor 164 from a supply line 26 at approximately 3 L/hr, and the carbon dioxide was bubbled at normal pressure through the aqueous solution, whereby the carbon dioxide was absorbed. The aqueous solution having the carbon dioxide absorbed therein was transferred into a tank reactor 165 via a transfer line 27, and reacted with a sulfuric acid aqueous solution (made by Wako Pure Chemical Industries, Ltd., Japan, concentration 47%) which was supplied in at approximately 3.5 L/hr from a supply line 28, and the aqueous solution that had been subjected to the reaction was recovered from a recovery line 29, while the eliminated carbon dioxide was recycled into the carbon dioxide complex production apparatus 140 via a transfer line 30, a compressor 163, and the transfer line 9. At the same time, the amount of carbon dioxide supplied in from the supply line 13 was gradually reduced, and in a steady state the supply of the carbon dioxide from the supply line 13 was stopped, and the unused carbon dioxide was transferred out from the transfer line 17 at approximately 764 g/hr. The carbon dioxide complex-containing mixture obtained was a liquid as in Example 18, and could be transferred out via the transfer line 10 at a temperature of 40° C. and a pressure of 0.05 MPa-G without problems such as blockage of the transfer line occurring. Furthermore, flow of gas through the vent line 12 was not seen, the recycled unused carbon dioxide being recovered in the form of the carbon dioxide complex-containing mixture. The mixture was sampled, and subjected to elemental analysis, whereupon the molar ratio between tin atoms, carbon dioxide, and OR groups in the mixture $(Z:(CO_2)_x:(OR)_y)$ was found to be such that $x=1.32$ and $y=1.71$. The bis(3-methylbutyl) carbonate-containing reaction liquid separated out by the thin film evaporator 160 was transferred via a transfer line 16 with the flow rate adjusted to approximately 5330 g/hr into a thin film evaporator 170 (made by Kobelco Eco-Solutions Co., Ltd., Japan) set to approximately 142° C. and approximately 0.5 kPa, and bis(3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20. After the carbon dioxide recycling was commenced, the bis(3-methylbutyl) carbonate yield gradually decreased, reaching a steady state at approximately 850 g/hr.

Comparative Example 7

1,1,3,3-Tetrabutyl-1,3-bis(3-methylbutyloxy)-distannoxane was produced using the same process as in step A of Example 18, and then a carbonate was produced in the following step.

Figure 11:
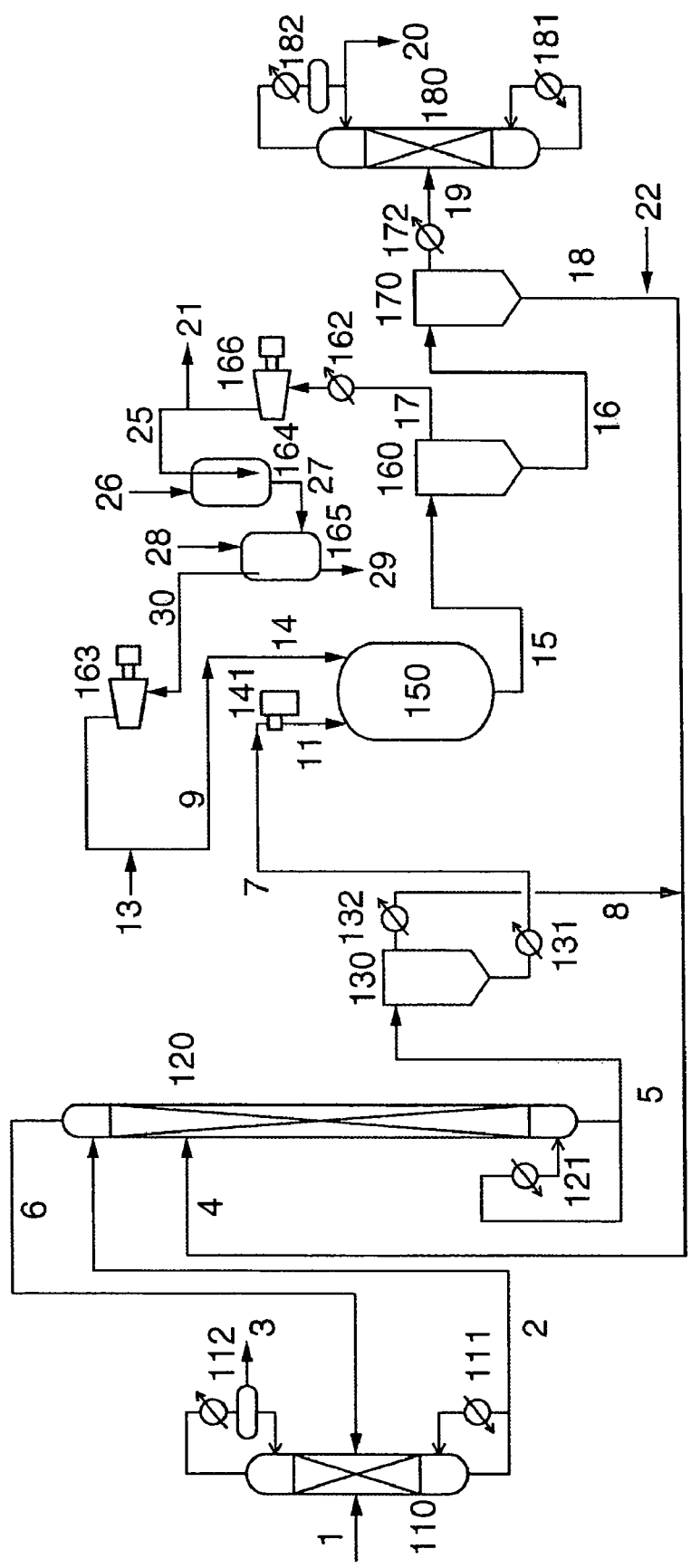
FIG. 11 shows a schematic diagram of a carbonate production apparatus including a carbon dioxide recovery step.

A carbonate was produced using a continuous production apparatus as shown in FIG. 11. The apparatus was not provided with a carbon dioxide complex production apparatus, but rather unused carbon dioxide was recovered by being reacted with an aqueous solution of an alkali. The 1,1,3,3-tetrabutyl-1,3-bis(3-methylbutyloxy)-distannoxane was supplied at 4388 g/hr from a transfer line 4 into a column reactor 120 of inside diameter 151 mm and effective length 5040 mm packed with a Metal Gauze CY packing (made by Sulzer Chemtech Ltd., Switzerland), and 3-methyl-1-butanol (made by Kuraray Co., Ltd., Japan) that had been purified in a distillation column 110 was supplied at 14952 g/hr from a transfer line 2 into the column reactor 120. The liquid temperature in the reactor was adjusted to 160° C. using a heater and a reboiler 121, and the pressure was adjusted to approximately 120 kPa-G using a pressure regulating valve. The residence time in the reactor was approximately 17 minutes. 14000 g/hr of water-containing 3-methyl-1-butanol was transferred from an upper portion of the reactor via a transfer line 6, and 825 g/hr of 3-methyl-1-butanol (made by Kuraray Co., Ltd., Japan) via a supply line 1, into the distillation column 110 which was packed with a Metal Gauze CY packing (made by Sulzer Chemtech Ltd., Switzerland) and had a reboiler 111 and a condenser 112, and purification was carried out by distillation. Distillate containing a high concentration of water from an upper portion of the distillation column 110 was condensed by the condenser 112, and recovered from a recovery line 3. Purified 3-methyl-1-butanol was transferred out via the transfer line 2 from a lower portion of the distillation column 110. An alkyltin alkoxide composition containing dibutyl-bis(3-methylbutyloxy)tin and 1,1,3,3-tetrabutyl-1,3-bis(3-methylbutyloxy)-distannoxane was obtained from a lower portion of the column reactor 120, and was supplied into a thin film evaporator 130 (made by Kobelco Eco-Solutions Co., Ltd., Japan) via a transfer line 5. 3-Methyl-1-butanol was evaporated off using the thin film evaporator 130, and returned into the column reactor 120 via a condenser 132, a transfer line 8 and the transfer line 4. The alkyltin alkoxide composition was obtained from a lower portion of the thin film evaporator 130, this composition containing approximately 74 wt % of dibutyl-bis(3-methylbutyloxy)tin and approximately 25 wt % of 1,1,3,3-tetrabutyl-1,3-bis(3-methylbutyloxy)-distannoxane. The composition was cooled to approximately 80° C. using a cooler 131, and supplied via a transfer line 7 and a booster pump 141 at a flow rate of approximately 5130 g/hr into an autoclave 150 equipped with a stirrer. Carbon dioxide was supplied at approximately 974 g/hr via a supply line 13, a transfer line 9, and a supply line 14 into the autoclave, the pressure in the autoclave being maintained at 4 MPa-G. The temperature in the autoclave was set to 120° C., and the residence time was adjusted to approximately 5 hours, whereby a bis(3-methylbutyl) carbonate-containing reaction liquid containing unused carbon dioxide was obtained. The reaction liquid was transferred via a transfer line 15 and a regulating valve into a thin film evaporator 160 (made by Kobelco Eco-Solutions Co., Ltd., Japan) set to a temperature of approximately 120° C. and a pressure of approximately 13 kPa. The unused carbon dioxide was separated off in a gaseous form, and was transferred into a tank reactor 164 via a cooler 162, a transfer line 17, a compressor 166, and a transfer line 25. A sodium hydroxide aqueous solution (made by Wako Pure Chemical Industries, Ltd, Japan, concentration 8 mol/L) was supplied into the tank reactor 164 from a supply line 26 at approximately 3 L/hr, and the carbon dioxide was bubbled at normal pressure through the aqueous solution, whereby the carbon dioxide was absorbed. The aqueous solution having the carbon dioxide absorbed therein was transferred into a tank reactor 165 via a transfer line 27, and reacted with a sulfuric acid aqueous solution (made by Wako Pure Chemical Industries, Ltd., Japan, concentration 47%) which was supplied in at approximately 3.5 L/hr from a supply line 28, and the aqueous solution that had been subjected to the reaction was recovered from a recovery line 29, while the eliminated carbon dioxide was recycled into the autoclave 150 via a transfer line 30, a compressor 163, the transfer line 9, and the supply line 14. At the same time, the amount of carbon dioxide supplied in from the supply line 13 was gradually reduced, and in a steady state the amount of unused carbon dioxide flowing through the transfer line 17 was approximately 763 g/hr, and the amount of carbon dioxide supplied in from the supply line 13 was approximately 210 g/hr.

The bis(3-methylbutyl) carbonate-containing reaction liquid separated out by the thin film evaporator 160 was transferred via a transfer line 16 with the flow rate adjusted to approximately 5330 g/hr into a thin film evaporator 170 (made by Kobelco Eco-Solutions Co., Ltd., Japan) set to approximately 142° C. and approximately 0.5 kPa, and bis (3-methylbutyl) carbonate-containing distillate was obtained. The distillate was supplied at approximately 950 g/hr via a condenser 172 and a transfer line 19 into a distillation column 180 which was packed with a Metal Gauze CY packing (made by Sulzer Chemtech Ltd., Switzerland) and had a reboiler 181 and a condenser 182, and purification was carried out by distillation, 99 wt % bis(3-methylbutyl) carbonate being obtained at 944 g/hr from a recovery line 20. After the carbon dioxide recycling was commenced, the bis (3-methylbutyl) carbonate yield gradually decreased, reaching a steady state at approximately 560 g/hr. A reduction in the amount of carbonate compared with Example 35 was observed.

Comparative Example 8

Approximately 60 g of hexamethylenediamine (made by Tokyo Chemical Industry Co., Ltd, Japan, purity 99%) was transferred into a transparent bottle in air and left to stand at room temperature (approximately 23° C.). The hexamethylenediamine was colorless and transparent immediately after being left to stand, but had turned yellow after approximately 1 year.

Example 36

Carbon dioxide complex obtained as in Example 2 was heated to approximately 120° C., so as to eliminate the carbon dioxide (water content approximately 10 ppm). Approximately 800 g of the carbon dioxide was reacted at room temperature with approximately 60 g of hexamethylenediamine (made by Tokyo Chemical Industry Co., Ltd, Japan, purity 99%). The hexamethylenediamine carbamate thus produced was a white solid, and this solid was transferred into a transparent bottle in air at room temperature as in Comparative Example 9 and left to stand at room temperature (approximately 23° C.) for approximately 1 year. After that, there had been no change in the color of the solid, and the solid was put into a 300 mL flask, purging with nitrogen was carried out, and the solid was heated to 150° C. at normal pressure, so as to eliminate the carbon dioxide. The heating was continued until gas was no longer produced, whereby a colorless transparent liquid was obtained. The liquid was cooled to room temperature, and analyzed, whereupon it was found that the liquid was hexamethylenediamine, the purity being 99%.

Comparative Example 9

The carbon dioxide obtained from Comparative Example 6 (water content approximately 6000 ppm) was reacted at room temperature with approximately 60 g of hexamethylenediamine (made by Tokyo Chemical Industry Co., Ltd, Japan, purity 99%). The hexamethylenediamine carbamate thus produced was a white solid, and this solid was transferred into a transparent bottle in air at room temperature as in Comparative Example 9 and left to stand at room temperature (approximately 23° C.) for approximately 1 year. After that, there had been no change in the color of the solid, and the solid was put into a 300 mL flask, purging with nitrogen was carried out, and the solid was heated to 150° C. at normal pressure, so as to eliminate the carbon dioxide. The heating was continued until gas was no longer produced, whereby a brown liquid was obtained. The liquid was cooled to room temperature, and analyzed, whereupon it was found that the liquid was hexamethylenediamine, the purity being approximately 97%.

INDUSTRIAL APPLICABILITY

By using the mixture according to the present invention, carbon dioxide can be transferred as a liquid mixture, and furthermore carbon dioxide obtained from the mixture contains substantially no water. Moreover, the mixture according to the present invention can easily be obtained by reacting carbon dioxide gas and an alkyltin alkoxide composition together, and hence can be used as a carbon dioxide recovery utilization mixture with good efficiency. The present invention is thus very useful industrially.

We claim:
1. A method of obtaining a liquid mixture for transferring carbon dioxide, comprising
reacting gaseous carbon dioxide with an alkyltin alkoxide at a temperature in a range of from −60° C. to 100° C., forming a carbon dioxide complex of an alkyltin alkoxide, and
preparing a liquid mixture comprising
an alkyltin alkoxide composition containing an alkyltin alkoxide, the carbon dioxide complex, and a tetraalkyldialkoxydistannoxane; and
carbon dioxide;
wherein taking the number of mols of tin atoms in the alkyltin alkoxide and/or the carbon dioxide complex of the alkyltin alkoxide contained in the mixture to be Z,
taking carbon dioxide incorporated in the carbon dioxide complex of the alkyltin alkoxide, and carbon dioxide contained in the mixture to be ($CO_2$),
and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide, in a relationship Z:($CO_2$)$_x$:(OR)$_y$, a molar proportion represented by Z is 1, a molar proportion represented by x is in a range of from 0.1 to 2, and a molar proportion represented by y is in a range of from 0.5 to 2.

2. The method according to claim 1, wherein each of the R groups is an aliphatic group.

3. The method according to claim 1, wherein each of the R groups is an alkyl group having from 1 to 6 carbon atoms.

4. The method according to claim 1, wherein each of the R groups is an alkyl group having from 4 to 6 carbon atoms.

5. The method according to claim 1, wherein the chemical reaction is brought about at a pressure in a range of from about 1 atm to 1 MPa.

6. The method according to claim 1, wherein the alkyltin alkoxide composition is in a liquid state when the gaseous carbon dioxide is absorbed therein.

7. The method according to claim 1, wherein the tetraalkyldialkoxydistannoxane is a tetraalkyldialkoxydistannoxane represented by following general formula (1):

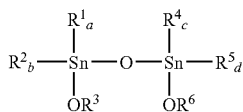

(1)

wherein $R^1$, $R^2$, $R^4$, and $R^5$ independently represent an aliphatic group or an aralkyl group, $R^3$ and $R^6$ independently represent an aliphatic group or an aralkyl group, a and b are integers from 0 to 2 with a+b=2, and c and d are integers from 0 to 2 with c+d=2.

8. The method according to claim 1, wherein the alkyltin alkoxide composition is an alkyltin alkoxide composition containing a monomer, aggregate, or polymeric component of at least one dialkyltin alkoxide.

9. A carbonate production process, comprising reacting the liquid mixture according to claim 1 with carbon dioxide.

10. A carbon dioxide recovery utilization method comprising:
heating and/or subjecting to reduced pressure the liquid mixture obtained from the method according to claim 1 so as to eliminate carbon dioxide, and utilizing the eliminated carbon dioxide.

11. A process for producing a dry gaseous carbon dioxide, comprising obtaining the liquid mixture obtained from the method according to claim 1, the liquid mixture being a mixture obtained by continuously supplying gaseous carbon dioxide into a reactor and bringing about chemical reaction, and simultaneously continuously withdrawing a gas phase portion from the reactor, so as to obtain dry gaseous carbon dioxide having a lower water content than the continuously supplied gaseous carbon dioxide.

12. The method according to claim 1, wherein the gaseous carbon dioxide is reacted with the alkyltin alkoxide composition at a temperature in a range of from −40° C. to 80° C.

13. A method for transferring carbon dioxide, comprising transferring the liquid mixture obtained from the method according to claim 1 through a vessel, piping, or a feeding pump.

14. The method for transferring according to claim 13, wherein the liquid mixture is transferred at a temperature in a range of from −40° C. to 80° C.

15. The method according to claim 1, wherein the alkyltin alkoxide composition contains a dialkyltin dialkoxide.

16. The method according to claim 15, wherein a molar ratio between the tetraalkyldialkoxydistannoxane and the dialkyltin dialkoxide contained in the alkyltin alkoxide composition is in a range of from 10:90 to 80:20.

17. The method according to claim 15, wherein the mixture further contains a carbonate, the content of the carbonate being less than 20 mol % based on the number of mols of the tetraalkyldialkoxydistannoxane in the alkyltin alkoxide composition.

18. The method according to claim 15, wherein the dialkyltin dialkoxide is a dialkyltin dialkoxide represented by following general formula (2)

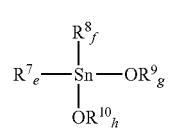

(2)

wherein $R^7$ and $R^8$ independently represent an aliphatic group or an aralkyl group, $R^9$ and $R^{10}$ independently represents an aliphatic group or an aralkyl group, e and f are integers from 0 to 2 with e+f=2, and g and h are integers from 0 to 2 with g+h=2.

19. A carbonate production process comprising:
obtaining a liquid mixture comprising
carbon dioxide and
an alkyltin alkoxide composition containing a carbon dioxide complex of an alkyltin alkoxide obtained by reacting the alkyltin alkoxide with gaseous carbon dioxide at a temperature in a range of from −60° C. to 100° C.,
wherein taking the number of mols of tin atoms in the alkyltin alkoxide and/or the carbon dioxide complex of the alkyltin alkoxide contained in the liquid mixture to be Z,
taking carbon dioxide incorporated in the carbon dioxide complex of the alkyltin alkoxide, and carbon dioxide contained in the liquid mixture to be ($CO_2$),
and taking OR groups contained in the mixture to be (OR), wherein O in each of the OR groups represents an oxygen atom, and R represents an aliphatic group or an aralkyl group, being (i) R of an OR group forming a tin-OR linkage and/or (ii) R of an OR group forming an —O—(CO)—OR linkage in the carbon dioxide complex of the alkyltin alkoxide,
in the relationship Z:($CO_2$)$_x$:(OR)$_y$, a molar proportion represented by Z is 1, a molar proportion represented by x is in a range of from 0.1 to 2, and a molar proportion represented by y is in a range of from 0.5 to 2;
transferring the liquid mixture into a carbonate-producing reactor;
obtaining a reaction liquid containing a carbonate from the mixture under a presence of carbon dioxide; and
obtaining the carbonate by separating the carbonate from the reaction liquid.

20. The method according to claim 19, wherein the gaseous carbon dioxide is reacted with the alkyltin alkoxide at a temperature in a range of from −40° C. to 80° C.

21. The carbonate production process according to claim 19, further comprising:
separating out carbon dioxide as a gaseous component from the reaction liquid; and recycling the separated out gaseous carbon dioxide in the step of obtaining the liquid mixture.

22. The carbonate production process according to claim 21, further comprising:

separating out the carbonate from the reaction liquid from which the carbon dioxide has been separated out, so as to obtain a residual liquid;

reacting the residual liquid with an alcohol, so as to obtain the alkyltin alkoxide composition; and recycling the alkyltin alkoxide composition into the step of obtaining the liquid mixture.

23. The carbonate production process according to claim 22, wherein the alcohol is an alcohol represented by following formula (3):

$$R^{11}OH \tag{3}$$

wherein $R^{11}$ has the same definition as R in the OR groups in the liquid mixture.

* * * * *